(12) United States Patent
Grant et al.

(10) Patent No.: US 12,016,542 B2
(45) Date of Patent: Jun. 25, 2024

(54) IMPLANTABLE DEVICES, SYSTEMS AND METHODS FOR CLOSING APERTURE

(71) Applicant: Vivasure Medical Limited, Galway (IE)

(72) Inventors: Peter Grant, Galway (IE); Mark McGoldrick, Athlone (IE); Gerard Brett, Claregalway (IE)

(73) Assignee: Vivasure Medical Limited, Galway (IE)

( * ) Notice: Subject to any disclaimer, the term of this patent is extended or adjusted under 35 U.S.C. 154(b) by 58 days.

(21) Appl. No.: 17/673,240

(22) Filed: Feb. 16, 2022

(65) Prior Publication Data
US 2022/0257225 A1 Aug. 18, 2022

Related U.S. Application Data

(60) Provisional application No. 63/150,378, filed on Feb. 17, 2021.

(51) Int. Cl.
*A61B 17/00* (2006.01)

(52) U.S. Cl.
CPC .............. *A61B 17/0057* (2013.01); *A61B 2017/00659* (2013.01); *A61B 2017/00672* (2013.01)

(58) Field of Classification Search
CPC ...... A61B 17/0057; A61B 2017/00004; A61B 2017/00646; A61B 2017/00659; A61B 2017/00672
See application file for complete search history.

(56) References Cited

U.S. PATENT DOCUMENTS

| | | |
|---|---|---|
| 2013/0274795 A1 | 10/2013 | Grant et al. |
| 2014/0018847 A1 | 1/2014 | Grant et al. |
| 2014/0180314 A1 | 6/2014 | Asfora |
| 2016/0166241 A1* | 6/2016 | McGoldrick .......... B05D 3/002 606/213 |
| 2016/0174953 A1 | 6/2016 | Grant et al. |
| 2017/0333014 A1 | 11/2017 | Grant et al. |
| 2018/0325505 A1 | 11/2018 | Phillips |
| 2019/0021710 A1 | 1/2019 | McGoldrick et al. |

FOREIGN PATENT DOCUMENTS

| | | |
|---|---|---|
| WO | WO-2016/096932 A1 | 6/2016 |
| WO | WO-2020/141122 A1 | 7/2020 |

OTHER PUBLICATIONS

International Search Report, International Application No. PCT/EP2022/053810, dated Jun. 13, 2022, 8 pages.
Written Opinion, International Application No. PCT/EP2022/053810, dated Jun. 13, 2022, 8 pages.

* cited by examiner

*Primary Examiner* — Mohamed G Gabr
(74) *Attorney, Agent, or Firm* — Choate, Hall & Stewart LLP; Peter A. Flynn; Volodymyr Koman

(57) ABSTRACT

The disclosed technology provides an implantable device for sealing an aperture in a tissue of a body lumen. In some embodiments, the implantable device comprises a flexible sealable member having an elongated shape so that a longitudinal dimension of the flexible sealable member is greater than a lateral dimension of the flexible sealable member.

12 Claims, 54 Drawing Sheets

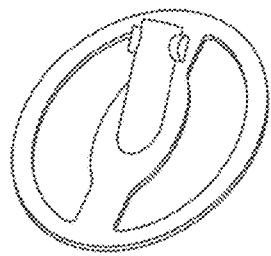 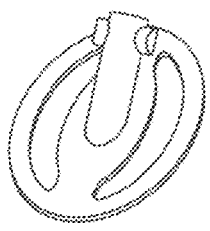 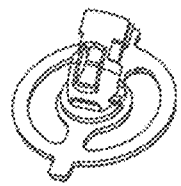 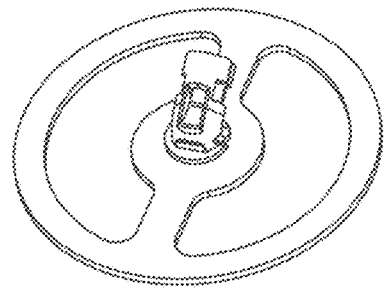
FIG. 18B      FIG. 18C      FIG. 18D      FIG. 18E
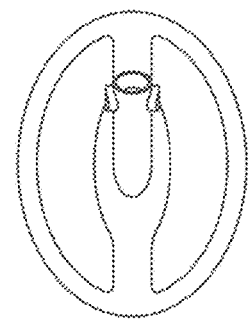 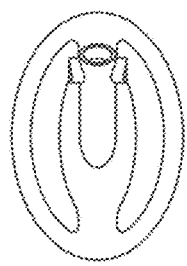 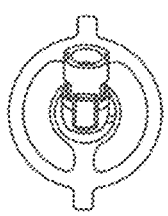 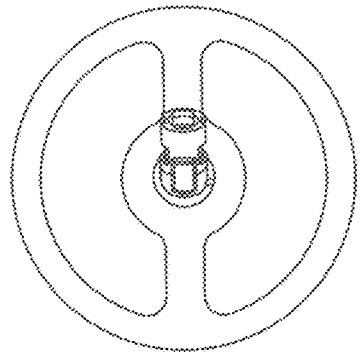
FIG. 18F      FIG. 18G      FIG. 18H      FIG. 18I

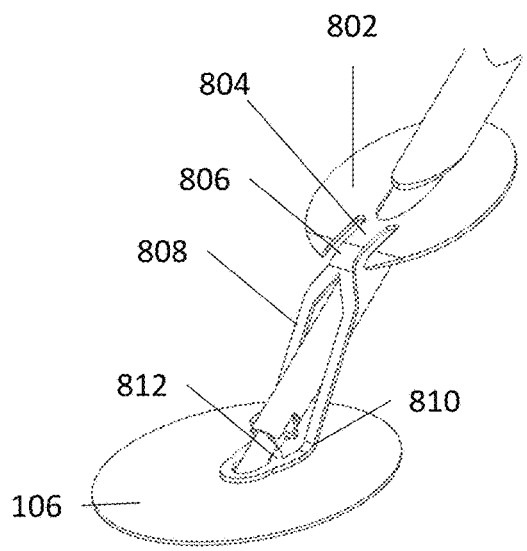
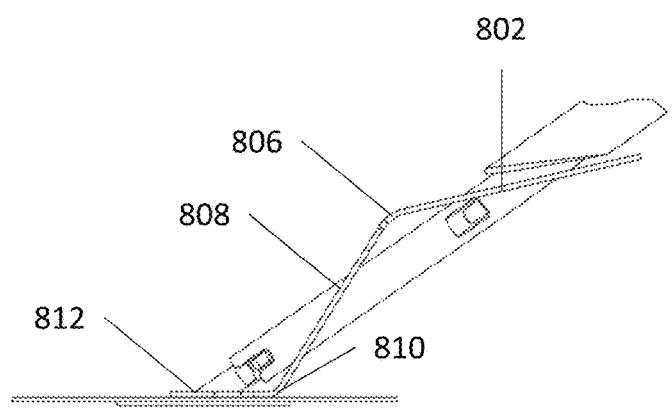
FIG. 34C  FIG. 34D
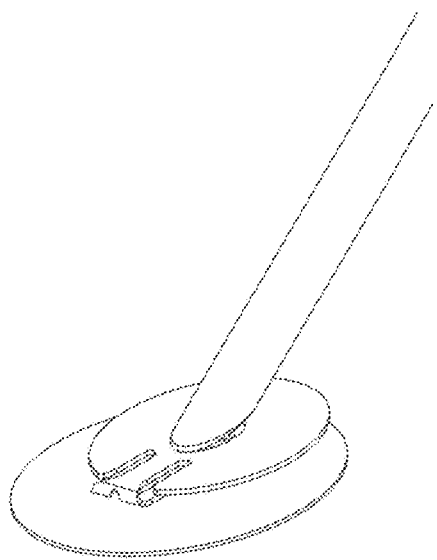
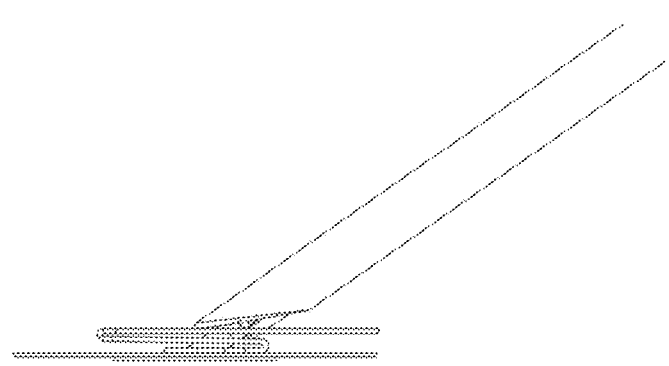
FIG. 34E  FIG. 34F

IMPLANTABLE DEVICES, SYSTEMS AND METHODS FOR CLOSING APERTURE

CROSS-REFERENCE TO RELATED APPLICATIONS

This application claims the benefit of priority to U.S. Provisional Patent Application No. 63/150,378, filed Feb. 17, 2021, which is incorporated by reference herein, in its entirety.

BACKGROUND

During a surgical or endoscopic operation on a body lumen, e.g., a blood vessel, an aperture is formed (e.g., from an arteriotomy) in the tissue of the lumen. Following the procedure, the aperture has to be closed in order for the lumen to heal. One relatively new type of closure apparatus has a flexible disc that is delivered into the body lumen to seal the aperture. The disc maintains the tissue in apposition until the lumen is healed, allowing the wound to heal from the inside of the lumen. The disc may operate in conjunction with a rigid core, which prevents the disc from dislodging from the sealing position.

In certain patient groups, the area surrounding the tissue within the body lumen is diseased and/or has accumulation (e.g., plaque or calcified lesions on the tissue wall). Due to the irregular surface topology of such areas, the effectiveness of the seal made by certain closure apparatuses is reduced, as channels are formed between the disc and the tissue surface.

There are benefits of improving the seal formed by a closure apparatus when closing an aperture formed in the tissue of the body lumen.

SUMMARY

The present disclosure provides an implantable closure device having a flexible sealable member and a support member. In certain embodiments, the present disclosure relates to an implantable device to improve a seal formed between the flexible sealable member and the tissue surface of the body lumen during closure of an aperture in the body lumen. In certain embodiments, the flexible sealable member has an elongated shape so that a longitudinal dimension of the flexible sealable member is greater than a lateral dimension of the flexible sealable member.

Among other things, the present disclosure identifies the source of at least one problem from prior strategies of implantable devices. In particular, certain implantable devices do not always provide consistent sealing in larger arteriotomies (e.g., outer dimeter larger than 20 F). In such cases, closures require longer time to hemostasis (e.g., more than 5 minutes), and therefore increased total procedure time. New implantable device designs described herein offer improvements on sealing ability (e.g., increased sealing consistency, reduced time to hemostasis).

The present disclosure provides insights regarding why the inconsistent sealing may occur. First, the implantable device may be too small for the target arteriotomy. Second, the implantable device may be located incorrectly relative to the arteriotomy. For example, if the center of the implantable device locates front or back of the arteriotomy, as shown in FIGS. 1 and 2, the coverage of the implantable device for the arteriotomy may be insufficient. Especially with large dissections, the actual positioning may make sealing and therefore hemostasis challenging. Additionally, as the deployment process of the implantable device typically involves pulling the implantable device backward (e.g., as shown in FIGS. 3 and 4), the deployment process may stretch the arteriotomy in the longitudinal axis of the vessel. The stretching in combination of the improper positioning (e.g., at the back of the arteriotomy) may originate inconsistent sealing. Third, when a patient receives antiplatelet therapy (APT) and/or anticoagulation therapy (ACT), the biological sealing processes takes longer. In such cases, higher compression (e.g., longer compression time and/or higher compression force, etc.) may be required.

However, increasing the size of the implantable devices does not necessarily solve this problem. For example, it requires a larger introducer to position a larger implantable device, potentially causing significant levels of damage at the arteriotomy site. Embodiments of the present disclosure include new designs that provide consistent sealing results while retaining the advantages of certain existing implantable devices.

In one aspect, the present disclosure provides a system for sealing an aperture in a tissue of a body lumen of a subject, which comprises (1) an implantable device comprising a flexible (e.g., rollable) sealable member that (a) is positionable against an internal surface of the tissue adjacent the aperture in the tissue when the implantable device is in a sealing position, (b) comprises a flexible substrate and a mesh layer disposed on (e.g., in contact with) the flexible substrate, and (c) has an elongated shape so that a longitudinal dimension of the flexible sealable member is greater than a lateral dimension of the flexible sealable member (e.g., wherein the flexible sealable member is oval in shape) (e.g., wherein the longitudinal dimension is at least 10, 20, 30, 40 or 50% greater than the lateral dimension); and (ii) a delivery device for delivering the implantable device into the subject for positioning of the flexible sealable member against the internal surface of the tissue adjacent the aperture.

In some embodiments, an average thickness of the flexible sealable member is greater than 100 μm (e.g., within a range of 100 μm to 500 μm, 200 μm to 400 μm, 200 μm to 300 μm, 200 μm to 280 μm or 200 μm to 250 μm).

In some embodiments, the aperture is located in a blood vessel, and a longitudinal axis of the flexible sealable member is aligned with (e.g., parallel to) a longitudinal axis of the blood vessel.

In some embodiments, the longitudinal dimension of the flexible sealable member is within a range of about 6 to about 10 mm and the lateral dimension of the flexible sealable member is within a range of about 4 mm to about 8 mm (e.g., wherein an outer diameter of the aperture is about 10 F).

In some embodiments, the longitudinal dimension of the flexible sealable member is within a range of about 10 to about 14 mm and the lateral dimension of the flexible sealable member is within a range of about 7 mm to about 11 mm (e.g., wherein an outer diameter of the aperture is about 15 F).

In some embodiments, the longitudinal dimension of the flexible sealable member is within a range of about 13 to about 17 mm and the lateral dimension of the flexible sealable member is within a range of about 10 mm to about 14 mm (e.g., wherein an outer diameter of the aperture is about 20 F).

In some embodiments, the longitudinal dimension of the flexible sealable member is within a range of about 18 to about 22 mm and the lateral dimension of the flexible sealable member is within a range of about 13 mm to about 17 mm (e.g., wherein an outer diameter of the aperture is about 26 F).

In some embodiments, the longitudinal dimension of the flexible sealable member is within a range of about 21 to about 25 mm and the lateral dimension of the flexible sealable member is within a range of about 15 mm to about 19 mm (e.g., wherein an outer diameter of the aperture is about 30 F).

In some embodiments, the longitudinal dimension of the flexible sealable member is within a range of about 25 to about 29 mm and the lateral dimension of the flexible sealable member is within a range of about 18 mm to about 22 mm (e.g., wherein an outer diameter of the aperture is about 35 F).

In some embodiments, an average thickness of the flexible substrate is within a range of 100 μm to 500 μm, 150 μm to 300 μm, 150 μm to 250 μm, or 190 μm to 220 μm.

In some embodiments, an average thickness of the mesh layer is within a range of 5 μm to 200 μm, 20 μm to 100 μm, or 20 μm to 80 μm.

In some embodiments, the mesh layer is in contact with the aperture when in the sealing position.

In some embodiments, the implantable device further comprises a support member.

In some embodiments, the support member comprises a base and a column, the column is disposed in and through the aperture, and the base is disposed in the body lumen to retain the sealable member against the interior surface of the tissue of the body lumen when the device is in the sealing position.

In some embodiments, the delivery system contains the implantable device, and the flexible sealable member is in a rolled conformation therein.

In some embodiments, the mesh layer comprises a plurality of electrospun fibers (e.g., facilitates tissue adhesion to the flexible sealable member by promoting platelet aggregation, or blood clotting with fibrin reinforcement of a platelet plug, etc. in the sealing position).

In some embodiments, the mesh layer comprises a synthetic agent and/or a biological agent.

In some embodiments, the implantable device comprises at least one material selected from the group consisting of polydioxanone, poly-L-lactide, poly-D-lactide, poly-DL-lactide, polyglycolide, ε-caprolactone, polyethylene glycol, and copolymers thereof.

In some embodiments, the implantable device comprises a locator positionable near an exterior surface of the tissue adjacent to the aperture when the device is in the sealing position. In some embodiments, the locator is moveable to be positioned near the exterior surface of the tissue adjacent to the aperture such that a portion of the tissue is disposed between the locator and the sealable member when the device is in the sealing position (e.g., wherein the column comprises an engagement portion to secure the locator to the support member).

In some embodiments, the mesh layer comprises a plurality of fibers each having a diameter in a range from 0.3 μm to 8 μm.

In some embodiments, the plurality of fibers makes up from 1 volume % to 35 volume % or 5 volume % to 25 volume % of the mesh layer.

In some embodiments, the system includes a closure pin disposed within the column for sealing the guidewire lumen after the guidewire is removed from the guidewire lumen. The closure pin includes an angled tip, a substantially circular pin head, a pair of first and second distally extending arms, a rupture portion, an offset bore, an angled pin, a slidable rod, and/or an L-shaped closure pin.

In some embodiments, the column includes an internal taper, a gradual tapered portion, a ramp portion, a sleeve portion, an angled surface, and/or a partial bore.

In some embodiments, the system includes a closure pin disposed within the column for sealing the guidewire lumen after the guidewire is removed from the guidewire lumen. Distally pushing the closure pin into the column causes the closure pin to seal the guidewire lumen.

In another aspect, the present disclosure provides an implantable device for sealing an aperture in a tissue of a body lumen of a subject. In some embodiments, the implantable device comprises a flexible (e.g., rollable) sealable member that (i) is positionable against an internal surface of the tissue adjacent the aperture in the tissue when the implantable device is in a sealing position, (ii) comprises a flexible substrate and a mesh layer disposed on (e.g., in contact with) the flexible substrate, and (iii) has an elongated shape so that a longitudinal dimension of the flexible sealable member is greater than a lateral dimension of the flexible sealable member (e.g., wherein the flexible sealable member is oval in shape).

In another aspect, the present disclosure provides a method for sealing an aperture in a tissue of a body lumen, the method comprising (i) deploying a flexible sealable member of an implantable device (e.g., causing a flexible sealable member to unfold) from a delivery state to a sealable state within the body lumen, wherein the delivery state of the sealable member has a first flex profile so as to fit through the aperture, wherein the sealable state of the sealable member has a second curved profile so as to form a tamponade of the aperture when the sealable member is engaged against an interior luminal surface of the tissue adjacent the aperture when the device is in a sealing position; and (ii) positioning the sealable member against the interior luminal surface of the tissue adjacent the aperture to form the tamponade at the sealing position over the aperture, wherein the flexible sealable member comprises a flexible substrate, and a mesh layer disposed on (e.g., in contact with) the flexible substrate (e.g., such that the mesh layer remains attached to the flexible substrate to bend as a single structure with the flexible substrate); and the flexible sealable member has an elongated shape so that a longitudinal dimension of the flexible sealable member is greater than a lateral dimension of the flexible sealable member (e.g., wherein the flexible sealable member is oval in shape).

In another aspect, the present disclosure provides an implantable device for sealing an aperture in a tissue of a body lumen, the implantable device comprising (i) a flexible sealable member positionable against an interior surface of the tissue adjacent the aperture in the tissue when the implantable device is in a sealing position; (ii) a support member comprising a base and a column, wherein the base of the support member comprises a support surface to support the flexible sealable member against the interior surface of the tissue when the implantable device is in the sealing position and the column extends through the sealing member and the aperture and comprises an engagement mechanism; and (iii) a locator coupled to the support member via the engagement mechanism and positionable against an exterior surface of the tissue adjacent the aperture when the implantable device is in the sealing position, so that at least a portion of the tissue is disposed between the locator and the flexible sealable member, wherein the locator comprises a first prong and a second prong.

In some embodiments, the locator further comprises a back portion connecting the first prong and the second prong.

In some embodiments, each of the first prong and the second prong comprises a front angled face and a back angled face.

In some embodiments, an angle between the front angled face and the back angled face of the first prong and/or the second prong is within a range of about 90 degrees to 175 degrees.

In some embodiments, an angle between the front angled face of the first prong and/or the second prong and the flexible sealable member (e.g., when the implantable device is in the sealing position) is within a range of about 5 degrees to 45 degrees.

In some embodiments, an angle between the back angled face of the first prong and/or the second prong and the flexible sealable member (e.g., when the implantable device is in the sealing position) is within a range of about 5 degrees to 45 degrees.

In some embodiments, an angle between the first prong and the second prong is within a range of 90 degrees to about 175 degrees.

In some embodiments, the first prong and the second prong are shaped substantially identical.

In some embodiments, the first prong and the second prong are symmetric from the perspective of a centerline of the column.

In some embodiments, the locator further comprises a locker, and when the implantable device is in the sealing position, the locker connects the locator to the column.

In another aspect, the present disclosure provides an implantable device for sealing an aperture in a tissue of a body lumen, the implantable device comprising: (i) a flexible sealable member positionable against an interior surface of the tissue adjacent the aperture in the tissue when the implantable device is in a sealing position; (ii) a support member comprising a base and a column, wherein the base of the support member comprises a support surface to support the flexible sealable member against the interior surface of the tissue when the implantable device is in the sealing position and the column extends through the flexible sealing member and the aperture; and (iii) a locator positionable against an exterior surface of the tissue adjacent the aperture when the device is in the sealing position, so that at least a portion of the tissue is disposed between the locator and the flexible sealable member, wherein the locator comprises a flat disc connected to a foldable connector attached to the flexible sealing member.

In some embodiments, the implantable device is in the sealing position, the foldable connector are folded twice.

In some embodiments, the implantable device is in the sealing position, the flat disc and foldable connector are disposed between the column (e.g., a tab on the column) and the flexible sealable member.

In some embodiments, the lateral dimension of the flat disc is about 50 to 90% of the lateral dimension of the flexible sealable member.

In some embodiments, the folding connector comprises a top portion, a middle portion, and bottom portion.

In some embodiments, the implantable device is in the sealing position, the middle portion is on the bottom portion, the top portion and the flat disc is on the middle portion.

In some embodiments, the folding connector comprises a first folding position, and the top portion and the middle portion are connected via the first folding position.

In some embodiments, the folding connector comprises a second folding position, and the middle portion and the bottom portion are connected via the second folding position.

In some embodiments, a distance between the flexible sealing member and a tap in the column is substantially similar to or slightly larger than a total thickness of the flat disc, the middle portion, the bottom portion and gaps therebetween.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable and/or bioabsorbable.

As used herein, "bioabsorbable" materials are those that, when introduced into cells, are broken down by cellular machinery (e.g., enzymatic degradation) or by hydrolysis into components that cells can either reuse, reabsorb, or dispose of without significant toxic effects on the cells. In certain embodiments, components generated by breakdown of a bioabsorbable material do not induce inflammation and/or other adverse effects in vivo. In some embodiments, bioabsorbable materials are enzymatically broken down. Alternatively or additionally, in some embodiments, bioabsorbable materials are broken down by hydrolysis. In some embodiments, bioabsorbable polymeric materials break down into their component polymers and/or monomers. In some embodiments, breakdown of bioabsorbable materials (including, for example, bioabsorbable polymeric materials) includes hydrolysis of ester bonds. In some embodiments, breakdown of materials (including, for example, bioabsorbable polymeric materials) includes cleavage of urethane linkages.

As used herein, "implant" is an object that is placed within a subject during a medical operation. The object may be biodegradable and/or bioabsorbable.

As used herein, "mesh" materials are those that, when introduced into a blood vessel, promote platelet capture (e.g., whereby the captured platelets encourages localized platelet activation, e.g., due to the contact with the collagen from the exposed wound, at the wound surface).

The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

The term "sample" refers to a volume or mass obtained, provided, and/or subjected to analysis. In some embodiments, a sample is or comprises a tissue sample, cell sample, a fluid sample, and the like. In some embodiments, a sample is taken from a subject (e.g., a human or animal subject). Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

As used herein, the term "substantially", and grammatical equivalents, refer to the qualitative condition of exhibiting at least a majority and total or near-total extent or degree of a characteristic or property of interest. One of ordinary skill in the art will understand that material and chemical phenomena rarely, if ever, go to completion and/or proceed to completeness or achieve or avoid an absolute result.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

BRIEF DESCRIPTION OF THE DRAWING

The Drawing, which is comprised of at least the following Figures, is for illustration purposes only, not for limitation.

FIG. 18B is a diagram showing a view of support member(s) of the implantable device, according to the present embodiments.

FIG. 18C is a diagram showing a view of support member(s) of the implantable device, according to the present embodiments.

FIG. 18D is a diagram showing a view of support member(s) of the implantable device, according to the present embodiments.

FIG. 18E is a diagram showing a view of support member(s) of the implantable device, according to the present embodiments.

FIG. 18F is a diagram showing a view of support member(s) of the implantable device, according to the present embodiments.

FIG. 18G is a diagram showing a view of support member(s) of the implantable device, according to the present embodiments.

FIG. 18H is a diagram showing a view of support member(s) of the implantable device, according to the present embodiments.

FIG. 18I is a diagram showing a view of support member(s) of the implantable device, according to the present embodiments.

FIG. 34C illustrates a view of the alternative locator of FIG. 34A, engaging with a delivery device in accordance with one or more embodiments of the invention.

FIG. 34D illustrates a view of the alternative locator of FIG. 34A, engaging with a delivery device in accordance with one or more embodiments of the invention.

FIG. 34E illustrates a view of the alternative locator of FIG. 34A, engaging with a delivery device in accordance with one or more embodiments of the invention.

FIG. 34F illustrates a view of the alternative locator of FIG. 34A, engaging with a delivery device in accordance with one or more embodiments of the invention.

FIG. 86 illustrates an image of a base and column used for a closure device, according to aspects of the present embodiments.

FIG. 87 illustrates an image of a scaffold used for a closure device, according to aspects of the present embodiments.

FIG. 88 illustrates an image of a closure device, according to aspects of the present embodiments.

FIG. 89 illustrates an image of a closure device, according to aspects of the present embodiments.

FIG. 90 illustrates an image of a closure device, according to aspects of the present embodiments.

FIG. 91 illustrates an image of a closure device, according to aspects of the present embodiments.

FIG. 92 illustrates an image of a closure device, according to aspects of the present embodiments.

DETAILED DESCRIPTION OF CERTAIN EMBODIMENTS

The following description is for illustration and exemplification of the present disclosure only and is not intended to limit the present disclosure to the specific embodiments described herein. Unless defined otherwise, technical and scientific terms have the same meaning as commonly understood by one of ordinary skill in the art to which this disclosure belongs. All references cited herein, including patent applications and publications, are incorporated by reference in their entirety.

As described herein, example embodiments of the present invention provide surgical closure systems, devices, and methods. As such, provided systems, devices, and methods are useful for closing a perforation (e.g., a hole, puncture, tear, rip, or cut, etc.) in any hollow vessel associated with a mammalian surgical procedure. One of ordinary skill in the art will appreciate that the systems, devices, and methods are useful for closing a perforation in any lumen of a mammal, including, for example, the gastrointestinal tract (e.g. the stomach, intestines, colon, etc.), heart, peritoneal cavity, esophagus, vagina, rectum, trachea, bronchi, or a blood vessel.

Implantable Device

Figure 5:
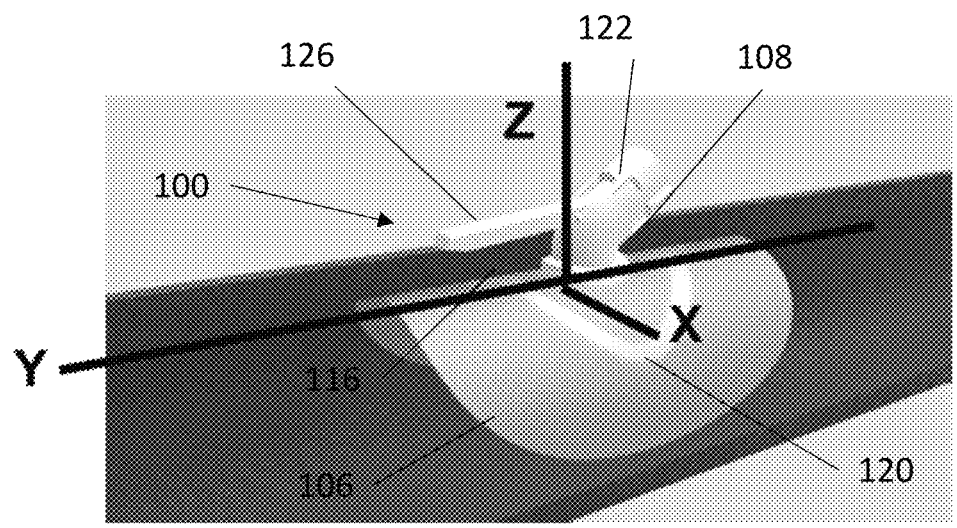
FIG. 5 is a diagram showing a perspective view of an exemplary implantable device deployed at a sealing position in a body lumen.
Figure 6:
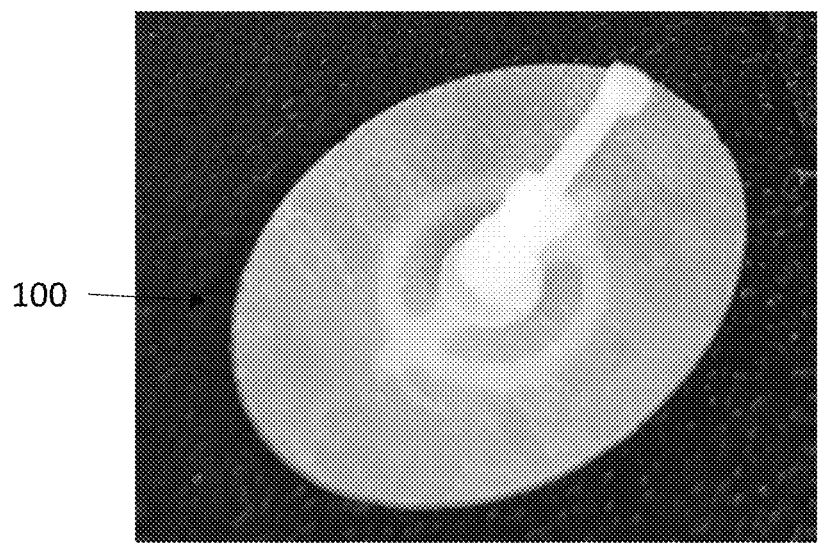
FIG. 6 is an image of an exemplary implantable device having an elongated shaped flexible sealable member.
Figure 7:
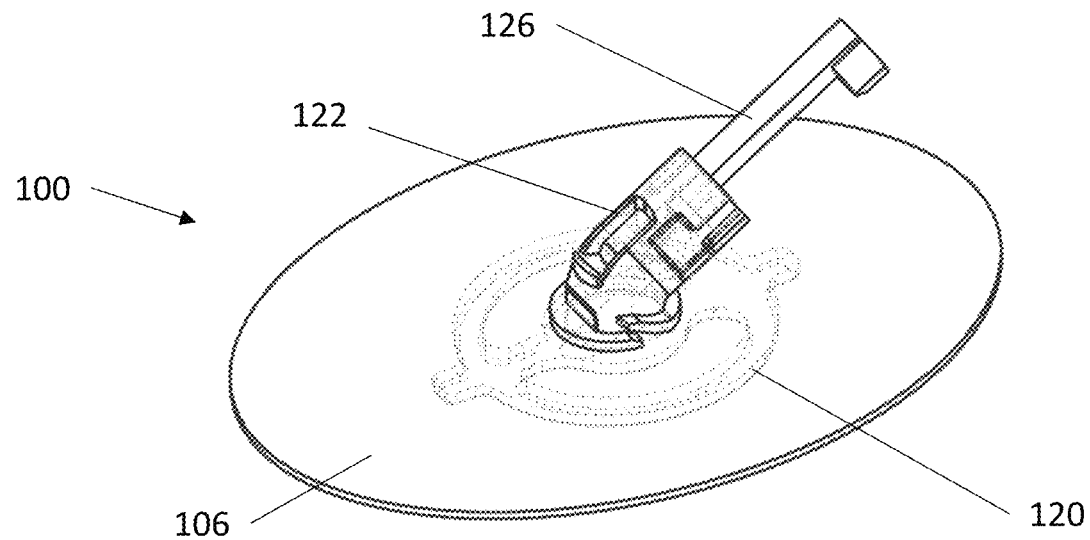
FIG. 7 is a diagram showing a view of an exemplary implantable device with a flexible sealable member, a support member and a locator.
Figure 8:
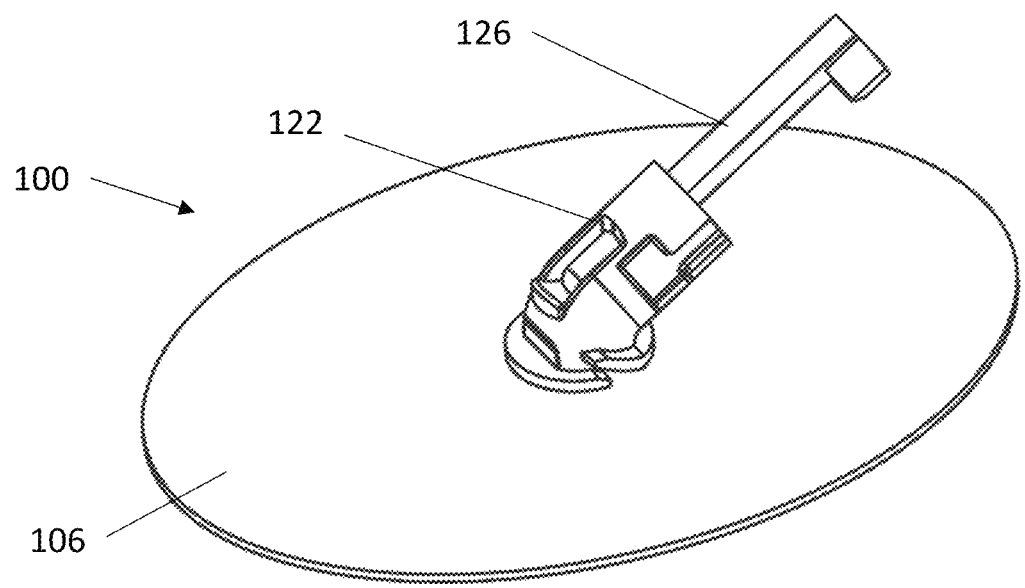
FIG. 8 is a diagram showing a view of an exemplary implantable device with a flexible sealable member, a support member and a locator.
Figure 9:
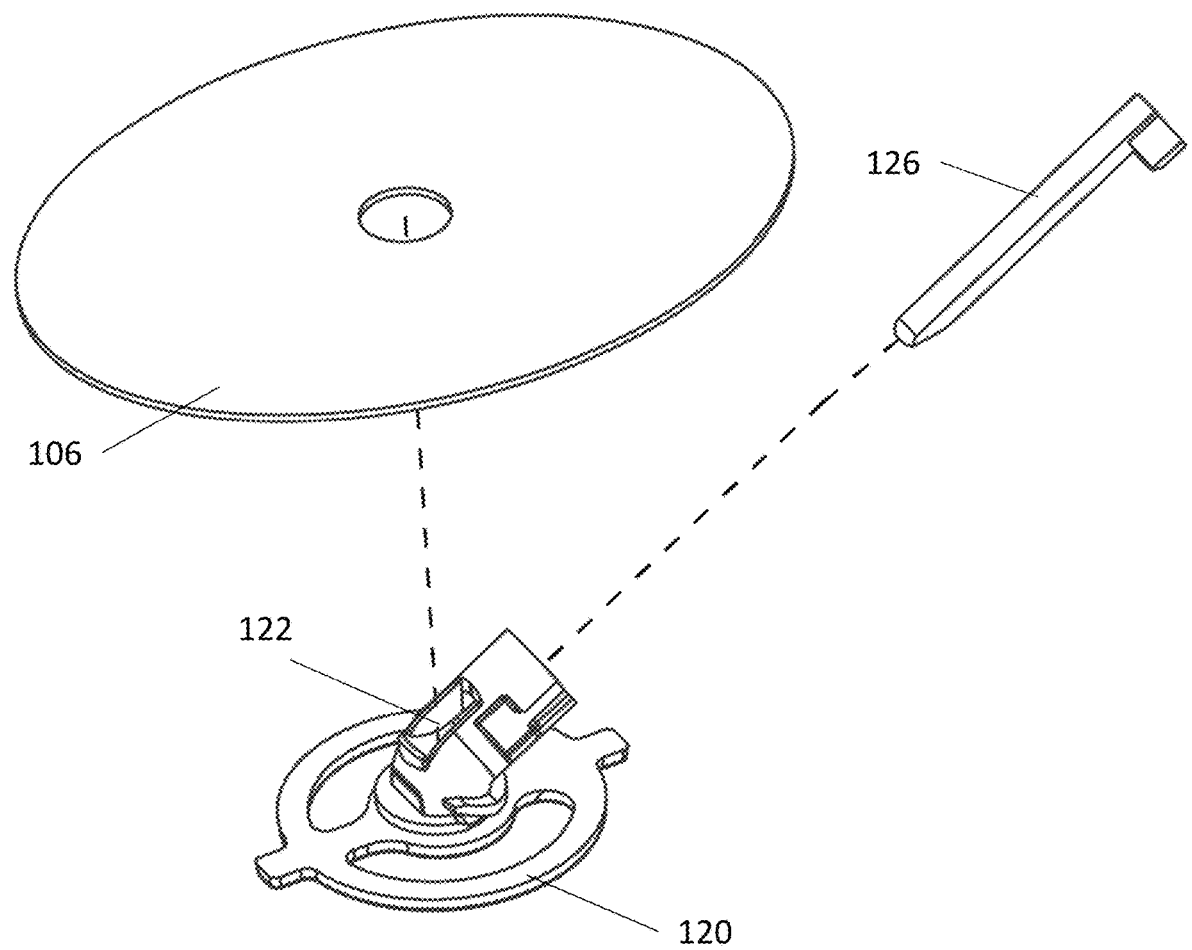
FIG. 9 is a diagram showing a view of an exemplary implantable device with a flexible sealable member, a support member and a locator.

FIG. 5 is a diagram showing an exemplary implantable device 100 deployed at a sealing position in a body lumen. The implantable device 100 includes a flexible sealable member 106 positionable against an interior surface 116 of a tissue adjacent an aperture 108. In some embodiments, the implantable device 100 form a tamponade at the aperture 108. Although flat or slightly curved when in a relaxed state, the flexible sealable member 106 flexibly curves to conform to the interior surface 116 of the lumen to which it engages, in the deployed state.

In some embodiments, the implantable device 100 includes a support member 118 comprising a base 120 and a column 122, as shown in FIGS. 5-12. The base 120 supports the flexible sealable member 106 during the delivery and deployment of the flexible sealable member 106 in the body lumen by retaining and/or holding the flexible sealable member 106 against the interior surface 116 of the tissue when the implantable device 100 is in the sealing position. In some embodiments, the base 120 exerts a force to bias the flexible sealable member 106 against the tissue.

In some embodiments, the column 122 of the support member 118 has an engagement portion to secure a locator 126 to the support member 118. In some embodiments, the locator 126 is maintained at a location relative to the exterior surface of the tissue when the closure device 100 is in the sealing position.

Flexible Sealable Member

Figure 12:
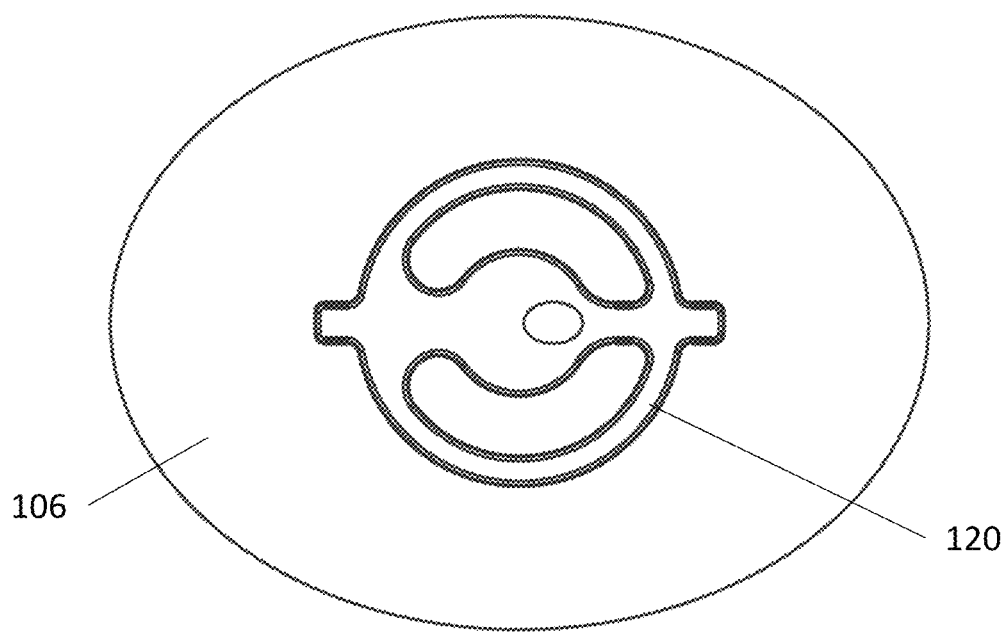
FIG. 12 is a diagram showing a bottom view of an exemplary implantable device and its elongated shaped flexible sealable member.
Figure 13:
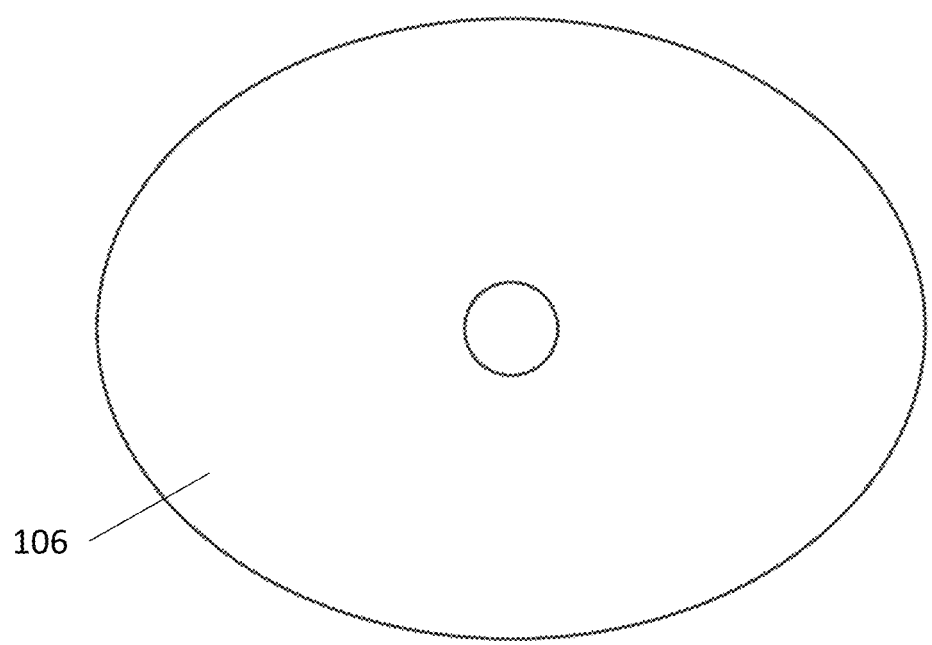
FIG. 13 is a diagram showing a bottom view of an exemplary implantable device and its elongated shaped flexible sealable member.

In some embodiments, the flexible sealable member 106 has an elongated shape as shown in FIGS. 12-13. In some embodiments, a longitudinal dimension of the flexible sealable member 106 is greater than a lateral dimension of the flexible sealable member 106. In some embodiments, the flexible sealable member 106 is oval in shape.

In some embodiments, the aperture is located in a blood vessel, and a longitudinal axis of the flexible sealable member 106 is aligned with (e.g., parallel to) a longitudinal axis of the blood vessel, as shown in FIG. 5. In some embodiments, the longitudinal dimension is at least about 5% greater than the lateral dimension. In some embodiments, the longitudinal dimension is at least about 10% greater than the lateral dimension. In some embodiments, the longitudinal dimension is at least about 15% greater than the lateral dimension. In some embodiments, the longitudinal dimension is at least about 20% greater than the lateral dimension. In some embodiments, the longitudinal dimension is at least about 25% greater than the lateral dimension. In some embodiments, the longitudinal dimension is at least about 30% greater than the lateral dimension. In some embodiments, the longitudinal dimension is at least about 35% greater than the lateral dimension. In some embodiments, the longitudinal dimension is at least about 40% greater than the lateral dimension. In some embodiments, the longitudinal dimension is at least about 45% greater than the lateral dimension. In some embodiments, the longitudinal dimension is at least about 50% greater than the lateral dimension.

Without wishing to be bound by any particular theory, it is contemplated that the elongated shape of the flexible sealable member 106 alleviates inconsistent sealing. For example, the elongated shape is useful when the aperture has a large diameter and a circular shape having the same surface area is too small for the aperture. As the elongated shape has an increased measurement in one direction (e.g., longitudinal direction, y-axis in FIG. 5) relative to the circular shape, the elongated shape can cover the aperture more than the circular shape at least in one direction, without requiring a larger delivery device that can cause significant levels of damage at the arteriotomy site.

Figure 1:
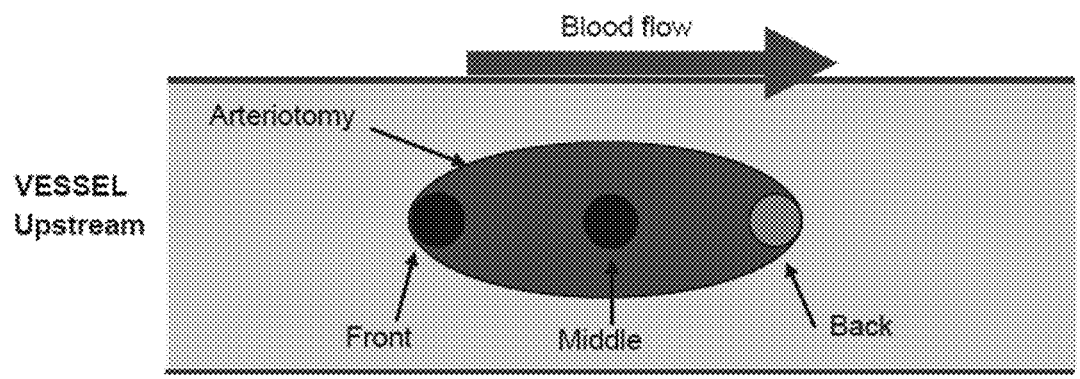
FIG. 1 illustrates three possible positions of an implantable device relative to an arteriotomy.
Figure 2:
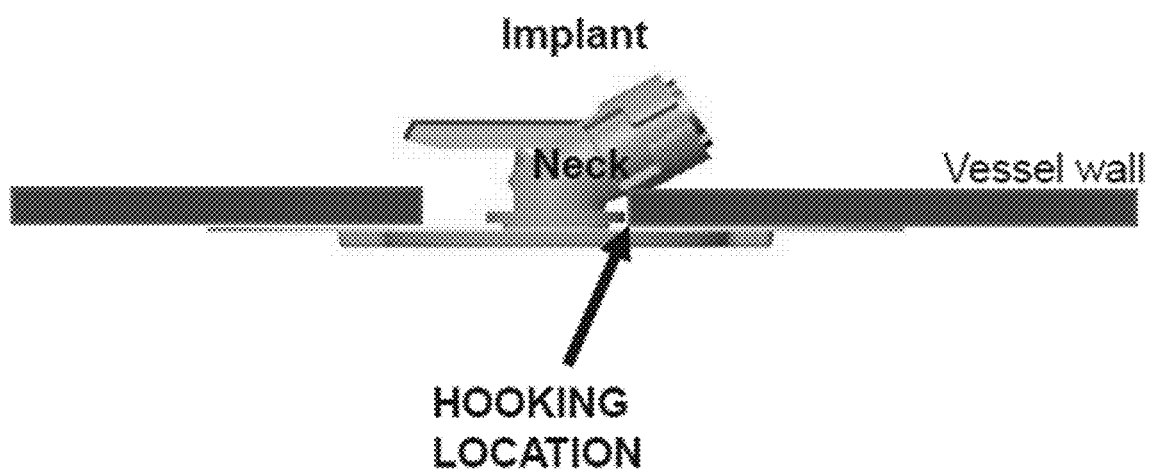
FIG. 2 shows an implantable device positioned back of the arteriotomy.
Figure 3:
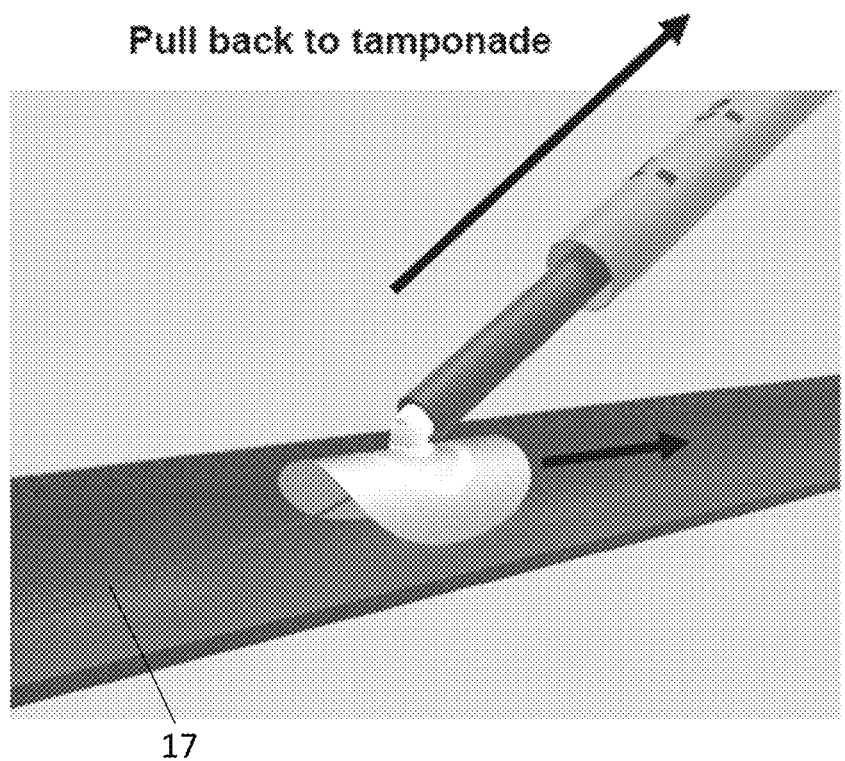
FIG. 3 depicts directions of force exerted on the implantable device during a deployment procedure. Forces may be applied to an arteriotomy site and contribute additional damages to the arteriotomy as a result of the advancement and retraction of this large introducer system.
Figure 4:
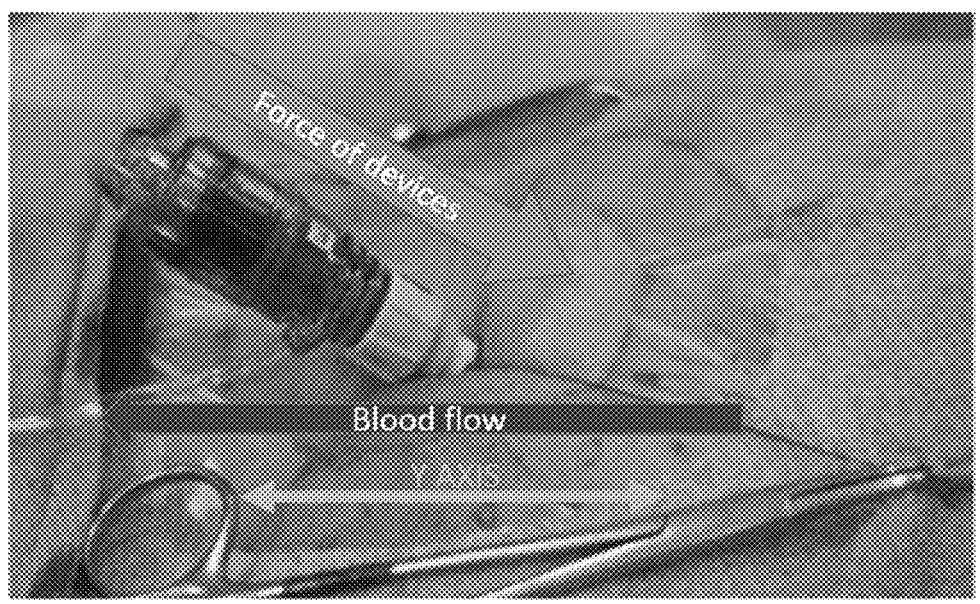
FIG. 4 depicts directions of force exerted on the implantable device during a deployment procedure. Forces may be applied to an arteriotomy site and contribute additional damages to the arteriotomy as a result of the advancement and retraction of this large introducer system.

In some embodiments, the elongated shape is advantageous over the circular shape having the same surface area, when the implantable device 100 tends to be located incorrectly relative to the arteriotomy 108 or the deployment process of the implantable device 100 stretches the arteriotomy 108. For example, even the implantable device 100 is positioned at the back of the arteriotomy 108 (e.g., as shown in FIGS. 1 and 2, e.g., due to pulling as shown in FIGS. 3 and 4), the elongated shape still can provide necessary coverage of the arteriotomy 108 due to its increased dimension.

In some embodiments, the flexible sealable member 106 is characterized in that it requires greater than about 5, 6, 7, 8, 9, 10, 11, 12, 13, 14, 15, 16, 17, 18, 19, or 20 N to be deformed and fitted in a vessel having an inner diameter of 8 mm (e.g., when the flexible sealable member has dimensions of about 20 mm, 15 mm and 0.230 mm).

In some embodiments, the average thickness of the flexible sealable member 106 is greater than about 100 μm. In some embodiments, the average thickness of the flexible sealable member 106 is greater than about 200 μm. In some embodiments, the average thickness of the flexible sealable member 106 is within a range of about 100 μm to about 500 μm, about 200 μm to about 400 μm, about 200 μm to about 300 μm, about 200 μm to about 280 μm, or about 200 μm to about 280 μm. In some embodiments, the flexible sealable member 106 described in the present disclosure has an average thickness greater than existing devices (e.g., about 120 μm).

Without wishing to be bound by any particular theory, it is contemplated that the increased thickness of the flexible sealable member 106 alleviates inconsistent sealing. For example, the increased thickness provides increased stiffness, so that the flexible sealable member exerts increased compressive force to the internal surface of the aperture.

In some embodiments, the flexible sealable member 106 includes a flexible substrate 104 and a mesh layer 102 disposed on the flexible substrate. In some embodiments, the flexible substrate 104 is in contact with the mesh layer 102. In some embodiments, the thickness of the flexible substrate 104 is within a range of about 100 µm to about 500 µm, about 150 µm to about 300 µm, about 150 µm to about 250 µm, or about 190 µm to about 220 µm. In some embodiments, the average thickness of the mesh layer 102 is within a range of 5 µm to 200 µm, 20 µm to 100 µm, or 20 µm to 80 µm.

Figure 43:
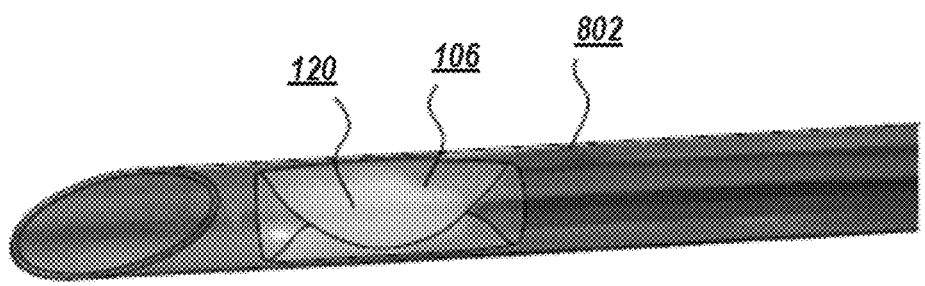
FIG. 43 is a diagram of the sealable member comprising the mesh layer and substrate folded in a delivery cannula of a closure device delivery system.
Figure 44:
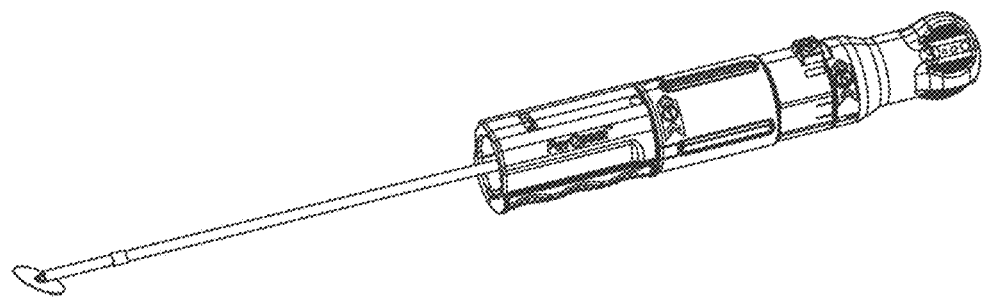
FIG. 44 illustrates an image of an exemplary embodiment of the delivery system.
Figure 45:
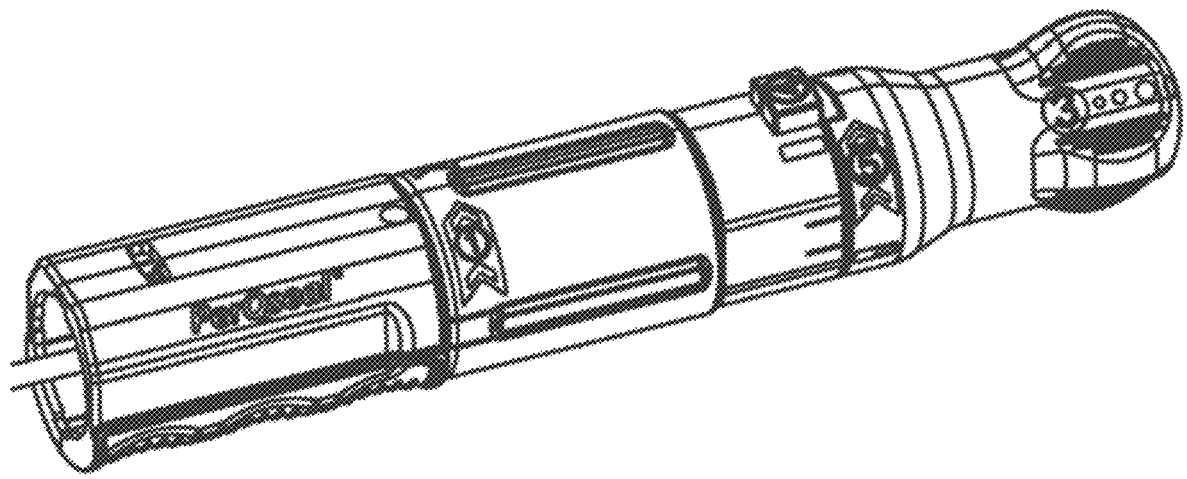
FIG. 45 illustrates an image of an exemplary embodiment of the delivery system.

The thickness of the mesh layer 102 and the substrate 104 is such that the flexible sealable member 106 can bend, in some embodiments, to conform to the interior surface of the blood vessel while sufficiently rigid to maintain the tamponade at the aperture 108 when the device 100 is in the sealing position. In some embodiments, the mesh layer 102 and flexible substrate 104 can roll, e.g., such that the tips of the flexible sealable member 106 touch each other, or bend beyond the curvature required to conform to the interior surface of the blood vessel, allowing the flexible sealable member 106 to fit within a delivery cannula to be deployed into the body lumen (e.g., as shown in FIG. 43).

In some embodiments, longitudinal and lateral dimensions of the flexible sealable member 106 is selected based on the size of the aperture to be sealed and/or the size of the blood vessel/hollow vessel.

In some embodiments, the longitudinal dimension of the flexible sealable member 106 is within a range of about 4 mm to about 12 mm, 4 mm to about 11 mm, 4 mm to about 10 mm, 5 mm to about 12 mm, 5 mm to about 11 mm, about 5 mm to about 10 mm, about 6 mm to about 11 mm, about 6 mm to about 10 mm, about 7 mm to about 11 mm, about 8 mm to about 12 mm, about 5 mm to about 9 mm, or about 4 mm to about 8 mm (e.g., when an outer diameter of the aperture is about 10 F (i.e., 3.3 mm)). In some embodiments, the lateral dimension of the flexible sealable member 106 is within a range of about 2 mm to about 10 mm, 2 mm to about 9 mm, 2 mm to about 8 mm, 3 mm to about 10 mm, 3 mm to about 9 mm, 3 mm to about 8 mm, 4 mm to about 10 mm, 4 mm to about 9 mm, 4 mm to about 8 mm, 5 mm to about 9 mm, 6 mm to about 10 mm, 3 mm to about 7 mm, or 2 mm to about 6 mm (e.g., when an outer diameter of the aperture is about 10 F (i.e., 3.3 mm)).

In some embodiments, the longitudinal dimension of the flexible sealable member 106 is within a range of about 8 mm to about 16 mm, about 8 mm to about 15 mm, about 8 mm to about 14 mm, 9 mm to about 16 mm, about 9 mm to about 15 mm, about 9 mm to about 14 mm, 10 mm to about 16 mm, about 10 mm to about 15 mm, about 10 mm to about 14 mm, about 11 mm to about 15 mm, about 12 mm to about 16 mm, about 9 mm to about 13 mm, or about 8 mm to about 12 mm (e.g., when an outer diameter of the aperture is about 15 F (i.e., 5 mm)). In some embodiments, the lateral dimension of the flexible sealable member 106 is within a range of about 5 mm to about 13 mm, about 5 mm to about 12 mm, about 5 mm to about 11 mm, about 6 mm to about 13 mm, about 6 mm to about 12 mm, about 6 mm to about 11 mm, about 7 mm to about 13 mm, about 7 mm to about 12 mm, about 7 mm to about 11 mm, about 8 mm to about 12 mm, about 9 mm to about 13 mm, about 6 mm to about 10 mm, or about 5 mm to about 9 mm (e.g., when an outer diameter of the aperture is about 15 F (i.e., 5 mm)).

In some embodiments, the longitudinal dimension of the flexible sealable member 106 is within a range of about 11 mm to 19 mm, about 11 mm to about 18 mm, about 11 mm to 17 mm, 12 mm to 19 mm, about 12 mm to 18 mm, about 12 mm to 17 mm, 13 mm to 19 mm, about 13 mm to 18 mm, about 13 mm to 17 mm, about 14 mm to 18 mm, about 15 mm to 19 mm, about 12 mm to 16 mm, or about 11 mm to 15 mm (e.g., when an outer diameter of the aperture is about 20 F (i.e., 6.7 mm)). In some embodiments, the lateral dimension of the flexible sealable member 106 is within a range of about 8 mm to about 16 mm, about 8 mm to about 15 mm, about 8 mm to about 14 mm, 9 mm to about 16 mm, about 9 mm to about 15 mm, about 9 mm to about 14 mm, 10 mm to about 16 mm, about 10 mm to about 15 mm, about 10 mm to about 14 mm, about 11 mm to about 15 mm, about 12 mm to about 16 mm, about 9 mm to about 13 mm, or about 8 mm to about 12 mm (e.g., when an outer diameter of the aperture is about 20 F (i.e., 6.7 mm)).

In some embodiments, the longitudinal dimension of the flexible sealable member 106 is within a range of about 16 mm about 24 mm, about 16 mm about 23 mm, about 16 mm about 22 mm, about 17 mm about 24 mm, about 17 mm about 23 mm, about 17 mm about 22 mm, about 18 mm about 24 mm, about 18 mm about 23 mm, or about 18 mm to about 22 mm (e.g., when an outer diameter of the aperture is about 26 F (i.e., 8.7 mm)). In some embodiments, the lateral dimension of the flexible sealable member 106 is within a range of about 11 mm to about 19 mm, about 11 mm to about 18 mm, about 11 mm to about 17 mm, about 12 mm to about 19 mm, about 12 mm to about 18 mm, about 12 mm to about 17 mm, about 13 mm to about 19 mm, about 13 mm to about 18 mm, or about 13 mm to about 17 mm (e.g., when an outer diameter of the aperture is about 26 F (i.e., 8.7 mm)).

In some embodiments, the longitudinal dimension of the flexible sealable member 106 is within a range of about 19 mm to about 27 mm, about 19 mm to about 26 mm, about 19 mm to about 25 mm, about 20 mm to about 27 mm, about 20 mm to about 26 mm, about 20 mm to about 25 mm, about 21 mm to about 27 mm, about 21 mm to about 26 mm, about 21 mm to about 25 mm, about 22 mm to about 26 mm, about 23 mm to about 27 mm, about 20 mm to about 24 mm, or about 19 mm to about 23 mm (e.g., when an outer diameter of the aperture is about 30 F (i.e., 10 mm)). In some embodiments, the lateral dimension of the flexible sealable member 106 is within a range of about 13 mm to about 21 mm, about 13 mm to about 20 mm, about 13 mm to about 19 mm, about 14 mm to about 21 mm, about 14 mm to about 20 mm, about 14 mm to about 19 mm, about 15 mm to about 21 mm, about 15 mm to about 20 mm, about 15 mm to about 19 mm, about 16 mm to about 20 mm, about 17 mm to about 21 mm, about 14 mm to about 18 mm, or about 13 mm to about 17 mm, (e.g., when an outer diameter of the aperture is about 30 F (i.e., 10 mm)).

In some embodiments, the longitudinal dimension of the flexible sealable member 106 is within a range of about 23 mm to about 31 mm, about 23 mm to about 30 mm, about 23 mm to about 29 mm, 24 mm to about 31 mm, about 24 mm to about 30 mm, about 24 mm to about 29 mm, 25 mm to about 31 mm, about 25 mm to about 30 mm, about 25 mm to about 29 mm, about 26 mm to about 30 mm, about 27 mm to about 31 mm, about 24 mm to about 28 mm, or about 23 mm to about 27 mm (e.g., when an outer diameter of the aperture is about 35 F (i.e., 11.7 mm)). In some embodiments, the lateral dimension of the flexible sealable member 106 is within a range of about 16 mm to about 24 mm, 16 mm to about 23 mm, 16 mm to about 22 mm, 17 mm to about 24 mm, 17 mm to about 23 mm, 17 mm to about 22 mm, 18 mm to about 24 mm, 18 mm to about 23 mm, 18 mm to about 22 mm, 19 mm to about 23 mm, 20 mm to about 24 mm, 17 mm to about 21 mm, or 16 mm to about 20 mm (e.g., when an outer diameter of the aperture is about 35 F (i.e., 11.7 mm)).

In some embodiments, the mesh layer 102 is formed by a bioabsorbable or biodegradable polymer that is electrospun onto the flexible substrate 104. The electrospinning process creates and/or forms a textured surface 114, by the mesh layer 102, for contacting the interior surface 116 of the 110 tissue.

Electrospinning employs, in some embodiments, electrical force to draw very fine fibers (e.g., micro or nano-scale) of polymers, ceramics, metals, carbon and/or composite materials from a liquid and/or a solution/melt. Electrospinning typically generates a jet in a high-voltage field to produce elongated fibers. A high-voltage electrical field is applied between a capillary where a suitable solution or melt is stored and a collection screen on which an electrically charged jet solidifies. For example, one electrode from a high-voltage source may be contacted with the solution/melt (e.g., needle, capillary) and the other attached to the collection screen. When a voltage is applied to a droplet of the solution/melt, the droplet is stretched into a jet due to electrostatic repulsion and surface tension. The jet is whipped by electrostatic repulsion until it is deposited on the collection screen. Electrospinning can be adjusted to produce continuous liquid jets by controlling parameters (e.g., molecular weight, viscosity, conductivity, surface tension, and electric potential, flow rate, concentration, distance between capillary and collection screen, temperature, needle gauge, etc.). The method beneficially ensures, among other benefits as described herein (e.g., combined with secondary processing (e.g., reduced pressure processing), that no solvent made from the manufacturing process is carried over into the final product. Other methods of generating very fine fibers may be employed.

The mesh layer 102 and/or the flexible substrate 104 comprise, in some embodiments, at least one material selected from the group consisting of polydioxanone, poly-L-lactide, poly-D-lactide, poly-DL-lactide, polyglycolide, ε-caprolactone, polyethylene glycol, and a copolymer thereof. In some embodiments, the material of the mesh layer 102 and/or flexible substrate 104 is a copolymer of, for example, but not limited to, polydioxanone, poly-L-lactide, poly-D-lactide, poly-DL-lactide, polyglycolide, ε-caprolactone, and polyethylene glycol. In some embodiments, the copolymer includes (a) monomers of polydioxanone, poly-L-lactide, poly-D-lactide, poly-DL-lactide, polyglycolide, ε-caprolactone, or polyethylene glycol, and (b) one or more additional monomers. In some embodiments, the (a) and (b) monomers form a polymer that is bioabsorbable. One of ordinary skill in the art will appreciate that other bioabsorbable and/or biodegradable material may be employed. In some embodiments, the mesh layer 102 and/or the flexible substrate 104 comprise collagen.

A bioabsorbable polymer can have crystalline and amorphous regions and are therefore, in general, semi-crystalline in nature. Degradation of a bioabsorbable polymer, in certain embodiments, initiates in the amorphous regions, with the crystalline regions degrading at a slower rate relative to the amorphous regions. Without wishing to be tied to a particular theory, and for illustrative purposes only, degradation of a polymer such as polydioxanone (PDO) occurs along the polymer back bone by hydrolysis of the ester bonds. This non-specific ester bond scission may occur randomly along the polymer chain with water penetration initially breaking the chemical bonds and converting the long polymer chains into natural monomeric acids found in the body, such as lactic acid. Such monomeric acids are then phagocytized by the enzymatic action of special types of mononuclear and multinuclear white blood cells. The polymer is, thus, degraded into non-toxic, low molecular weight residues that are capable of being eliminated from the body by normal metabolic pathways, e.g., via exhalation and/or excretion. Such a pathway thereby enables reference to the breakdown of such polymers in-vivo through terminology such as absorbable, bioabsorbable, degradation, biodegradation, resorbtion, bioresorbtion, among others.

Figure 14:
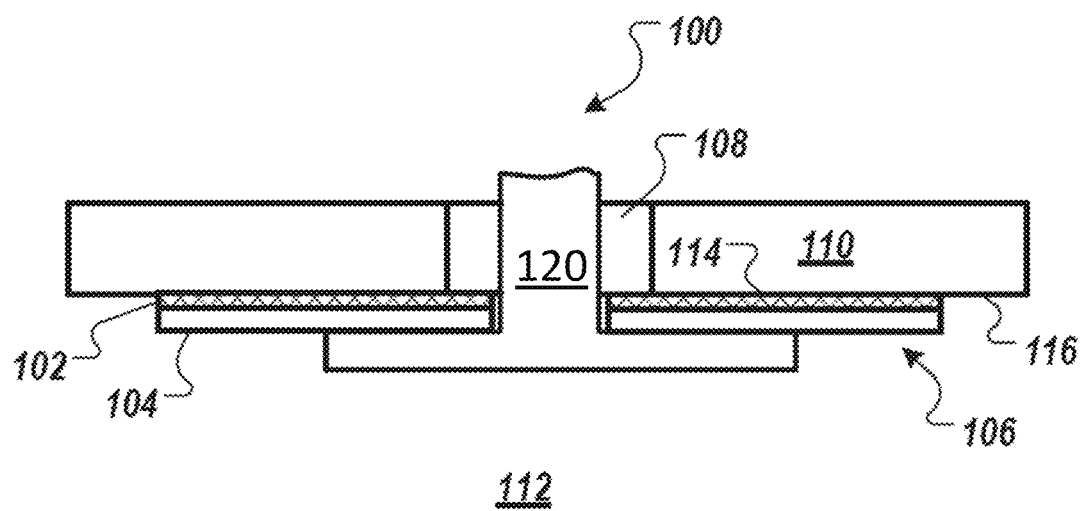
FIG. 14 is a diagram of an exemplary implantable device with a material system comprising a mesh layer and a substrate that, collectively, form a sealable member for closing an aperture in a body lumen, according to an illustrative embodiment.
Figure 15:
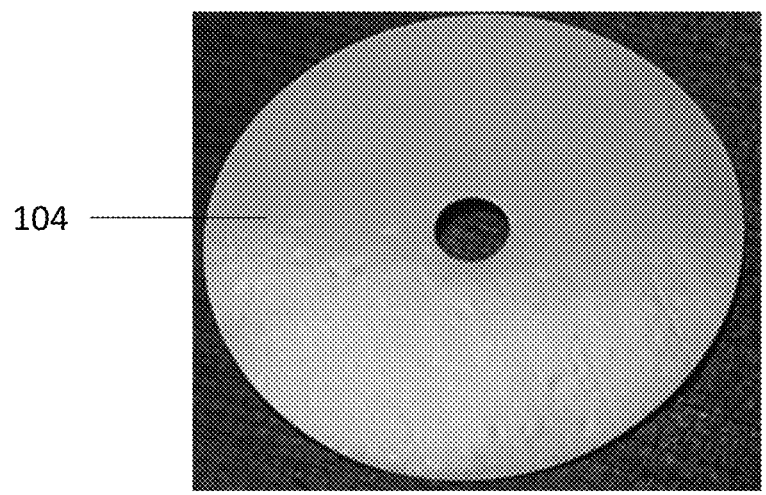
FIG. 15 is an image of the flexible substrate side of the sealable member.
Figure 16:
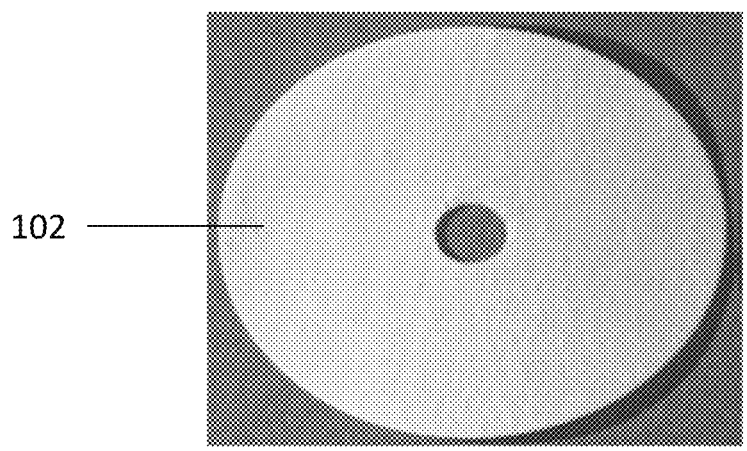
FIG. 16 is an image of the mesh (e.g., electrospun) side of the sealable member.
Figure 17:
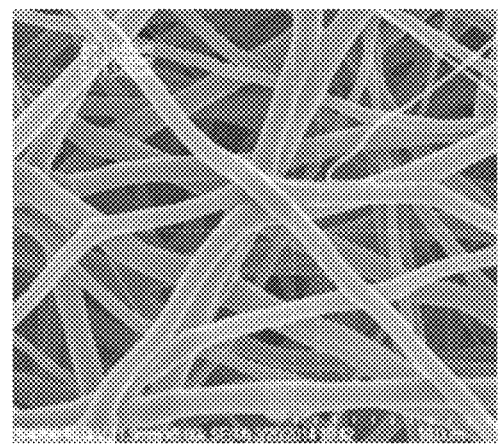
FIG. 17 is a Scanning Electron Microscope (SEM) image of the electrospun side of the sealable member under magnification.

Without wishing to be bounded to a particular theory, from the mesh layer 102, the electrospun side 114 of the flexible sealable member 106 has a larger (textured) surface area compared to an untreated smooth surface of the flexible substrate 104, on the other side of the flexible sealable member 106. This large surface area promotes platelet capture due to the pore size in the textured surface (e.g., whereby the captured platelet encourages localized platelet activation, e.g., due to contact with the collagen from the exposed wound, at the wound surface). During closing of the hole in the blood vessel 110, the flexible sealable member 106 is appositioned against the tissue at the hole 108 such that the textured flexible sealable member 106 surface 114 is positioned against the inner lumen of the vessel tissue. The textured surface 114 facilitates a faster and more secure adherence of the flexible sealable member 106 to the surrounding edges at the puncture site. The electrospun surface 114 of the flexible sealable member 106 promotes a faster hemostatic seal between the flexible sealable member 106 and the vessel inner luminal surface 116. The nature of the flexible sealable member 106 means it has a significant capability, beyond the state of the art, to provide sealing across a wide variety of blood vessel inner lumen surface topography. This topography can be in various states of disrepair due to disease and systemic diseases (e.g., diabetes). The electrospun surface 114 facilitates cellular adhesion, thereby acting as a "biological glue" and would aid encapsulation of the implant 100 in the vessel 110. As shown in FIG. 14, the base member 120 holds the flexible substrate 104 and mesh layer 102 (with electrospun surface 114) sandwiched to the inner wall of the blood vessel 110 thereby fluidly closing an interior of the blood vessel 112 from an exterior of the blood vessel.

In some embodiments, the mesh layer comprises a plurality of fibers each having a diameter in a range from 0.1 μm to 10 μm. In some embodiments, the mesh layer comprises a plurality of fibers each having a diameter in a range from 0.1 μm to 8 μm. In some embodiments, the mesh layer comprises a plurality of fibers each having a diameter in a range from 0.1 μm to 5 μm. In some embodiments, the mesh layer comprises a plurality of fibers each having a diameter in a range from 0.3 μm to 10 μm. In some embodiments, the mesh layer comprises a plurality of fibers each having a diameter in a range from 0.3 μm to 8 μm. In some embodiments, the mesh layer comprises a plurality of fibers each having a diameter in a range from 0.3 μm to 5 μm.

In some embodiments, the plurality of fibers makes up from 1% to 50% of the mesh layer volume. In some embodiments, the plurality of fibers makes up from 1% to 45% of the mesh layer volume. In some embodiments, the plurality of fibers makes up from 1% to 40% of the mesh layer volume. In some embodiments, the plurality of fibers makes up from 1% to 35% of the mesh layer volume. In some embodiments, the plurality of fibers makes up from 1% to 30% of the mesh layer volume. In some embodiments, the plurality of fibers makes up from 1% to 25% of the mesh layer volume. In some embodiments, the plurality of fibers makes up from 5% to 50% of the mesh layer volume. In some embodiments, the plurality of fibers makes up from 5% to 45% of the mesh layer volume. In some embodiments, the plurality of fibers makes up from 5% to 40% of the mesh layer volume. In some embodiments, the plurality of fibers makes up from 5% to 35% of the mesh layer volume. In some embodiments, the plurality of fibers makes up from 5% to 30% of the mesh layer volume. In some embodiments, the plurality of fibers makes up from 5% to 25% of the mesh layer volume.

In some embodiments, the mesh layer comprises a synthetic agent and/or a biological agent. In some embodiments, the mesh layer comprises collagen, sodium alginate, fibrin, or combinations thereof.

Other examples of the flexible sealable member (also referred to as a "flexible wing") are described in U.S. Patent Application Publication Nos. 2014/0018847 and 2016/0166241, the contents of which are incorporated by reference herein in their entirety.

Support Member

Figure 10:
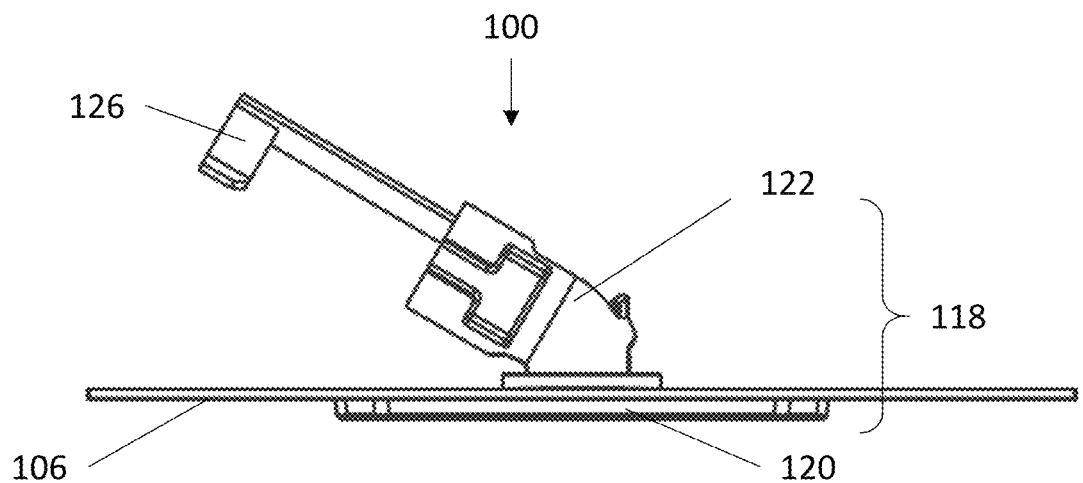
FIG. 10 is a diagram showing a view of an exemplary implantable device with a flexible sealable member, a support member and a locator.
Figure 11:
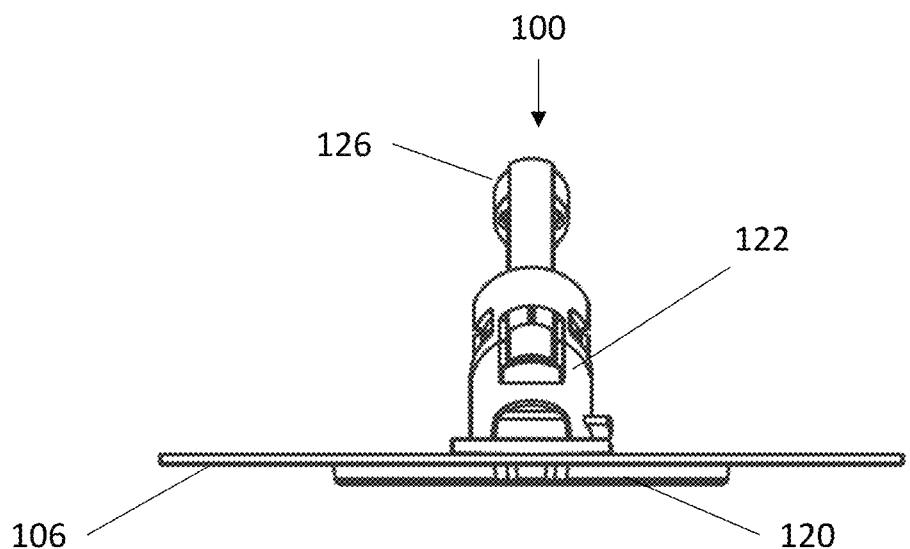
FIG. 11 is a diagram showing a view of an exemplary implantable device with a flexible sealable member, a support member and a locator.

In some embodiments, the support member 118 comprises a base 120 and a column 122. In some embodiments, the column 122 is disposed in and through the aperture, and the base 120 is disposed in the body lumen to retain the sealable member against the interior surface of the tissue of the body lumen when the device is in the sealing position. FIGS. 10 and 11 are diagrams of the flexible sealable member 106 and the base 120 of the support member 118 in a relaxed position, according to an illustrative embodiment. In some embodiments, the flexible sealable member 106 has a hole (e.g., located at or near the center of the member) sized to accept the column 122.

In some embodiments, once implanted in the body lumen, the base 120 presses against the interior shape of the lumen by hydraulic pressure exerted by fluids in the body lumen (e.g., by hemodynamic hydraulic forces exerted by blood in a blood vessel). In doing so, the base 120 improves the seal formed by the sealable member 106 over the aperture 108, thus, providing a faster and more secure closure of the aperture 108. The base 120 connects to the column 122, which is disposed, when the device is in the sealing position, in and through the aperture 108. In certain embodiments, a locator 126 (see FIGS. 10-11) maintains the column 122 in position at the sealing position once the device 100 is deployed, whereby the locator 126 prevents the dislodgement of the sealable member 106 from the sealing position, e.g., due to impact near the aperture or movement of the patient.

In some embodiments, once implanted in the body lumen, the base 120 bends against the interior shape of the lumen so as to compress the peripheral portions of the flexible sealable member 106 against the interior surface of the tissue 116. Hydraulic pressure, as discussed above, may contribute to the bending of the base 120 in such embodiments. The base 120, in these embodiments, also improves the seal formed by the flexible sealable member 106 over the aperture 108, thus, providing a faster and more secure closure of the aperture 108. The support member 118 may also include a locator 126 to prevent the dislodgement of the flexible sealable member 106 from the sealing position, e.g., due to impact near the aperture or movement of the patient.

In certain embodiments, the thickness of the support member 118 and the flexible sealable member 106 are selected such that the members 106, 118 are bendable to be loaded into a cannula while having sufficient rigidity to form and maintain a tamponade at the aperture when the device 100 is in the sealing position. In some embodiments, the thickness of the support member 118 is selected such that at least a portion of the support member 118 is rigid. In some embodiments, the base 120 of the support member 118 is sufficiently flexible to roll into a delivery funnel used for delivering the implant into the body lumen.

In certain embodiments, the base 120 of the support member 118 has a uniform thickness between about 0.1 mm and about 1.5 mm, including 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.10, 1.15, 1.20, 1.25, 1.30, 1.35, 1.40, 1.45, and 1.5 mm. In other embodiments, the thickness is varying.

FIGS. 12 and 18 diagrams showing a bottom view of a support member 118, according to an illustrative embodiment. The base 120 of the support member 118 includes (i) a central portion 302 that connects to column 122 and (ii) one or more lateral support portions 306 extending from the central portion 302. The lateral support portions 306 have support surfaces that retain and/or hold the peripheral portions of the sealable member 106 against the interior surface 108 of the tissue 110. In certain embodiments, the lateral support portion 306 retains and/or holds the peripheral portions and exerts a force that biases the sealable member 106 against the tissue. In certain embodiments, the force is compressive. The lateral support portions 306 in conjunction with the sealable member 106 increase the rigidity of the closure device 100 at regions of contact with the tissue 110, while allowing the closure device 100 to bend during the deployment and during the delivery. The increased rigidity reduces the risk that of inadvertent dislodgment of the closure device 100 after it has been deployed in the body lumen 104, e.g., due to an impact near the closure device or movements of the patient or of inadvertent pull-out of the device 100 (e.g., through the aperture) during its deployment into the body lumen 104.

In some embodiments, the central portion 302 forms a rigid core to which the lateral support portions 306 flexibly connect. In some embodiments, the central portion 302 and the lateral support portions 306 form a single unitary body.

In some embodiments, the lateral support portions 306 forms a gap 320 with respect to the central portion 302.

Still referring to FIGS. 12 and 18, the central portion 302 of the base 120 includes an anterior support portion 310 and a posterior support portion 312. The contact surfaces of both the anterior and posterior support portions 310, 312 contact and/or press against the anterior and posterior portions of the sealable member 106. The lateral support portions 306 extend from at least one of the anterior support portion 310 and the posterior support portion 312. As shown, the posterior support portion 312, in some embodiments, is disposed proximally to the column 122 of the support member 118, and the anterior support portion 312 is disposed distally to the column 122.

In some embodiments, the support member 118 may be shaped to provide more rigidity to peripheral portions of the flexible sealable member 106 along a direction to which the flexible sealable member 106 is pulled during the deployment of the closure device 100. The directionally-induced rigidity ameliorates the risk of an accidental pull-out of the flexible sealable member 106 from the lumen during deployment. For example, increased rigidity is employed at a specific part of the base 120 that, preferably, corresponds to the direction of the column 122. In certain embodiments, the base 120 provides more resistance, for example, at region 312, making the portion of the flexible sealable member 106 corresponding to such region subject to less bending. Thus, greater force may be applied to that region of the flexible sealable member 106 before the flexible sealable member 106 would pull through the aperture 108. This reduces the risk that the implant can dislodge from its deployed position due to, for example, movements by the patient and/or impact to the nearby area. The greater force also gives the surgeon a better tactile feel of the flexible sealable member 106 during the deployment and creates better apposition of the flexible sealable member 106 against the inner lumen of the body lumen. Thus, a faster and more effective seal can be created.

Figure 18A:
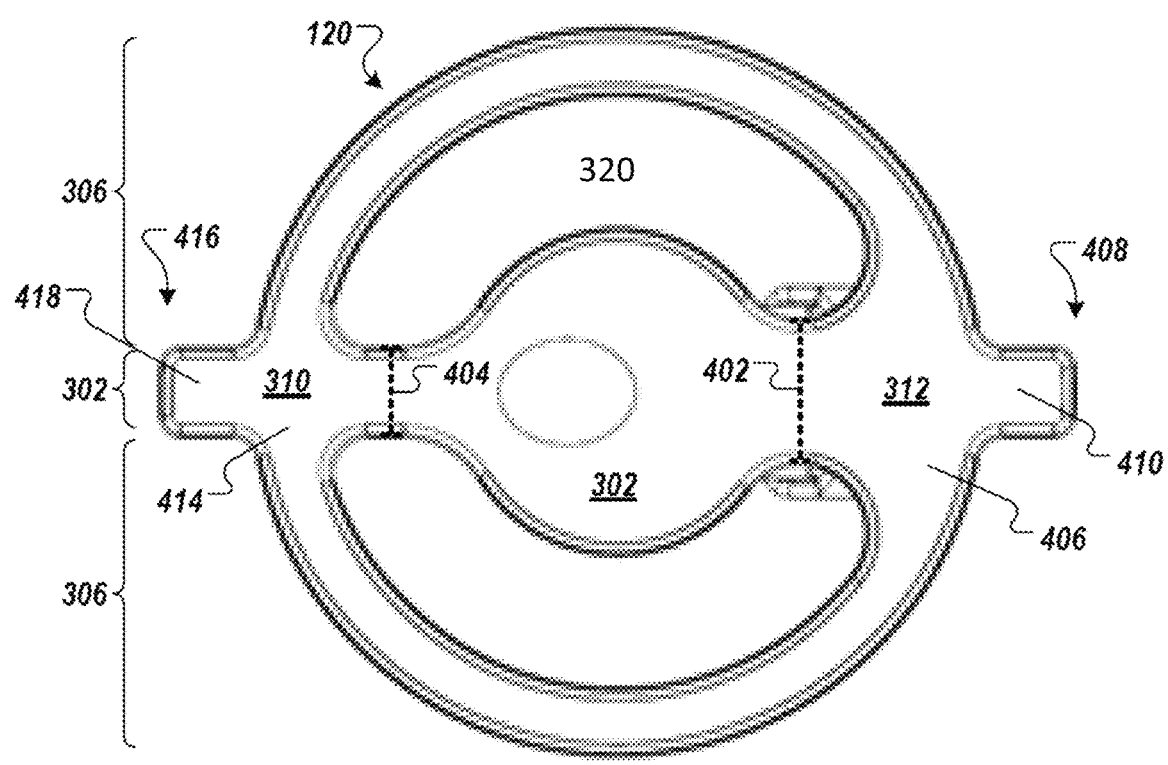
FIG. 18A is a diagram showing a bottom view of a support member of the closure device with directionally-induced rigidity, according to an illustrative embodiment.

As shown in FIG. 18A, in some embodiments, the posterior support portion 312 is disposed proximally to the column 122 of the support member 118 and has first maximum cross-sectional area 402. The anterior support portion 310 is disposed distally to the column 122 of the support member 118 and has a second maximum cross-sectional area 404. The first maximum cross-sectional area 402, in certain embodiments, is larger than the second maximum cross-sectional area 404 such that the posterior support portion 312 (and/or adjacent portions of the lateral support member) is more rigid than the anterior support portion 310.

In certain embodiments, the base 120 of the support member 118 has a varying cross-sectional thickness along the direction between the anterior support portion 310 and the posterior support portion 312. The varying thickness along this direction may provide greater rigidity at the posterior support portion 312 of the base 120 than the anterior support portion 310.

Referring still to FIG. 18A, in certain embodiments, the lateral support portions 306 extend from the posterior support portion 312 at a location 406 between (i) a posterior end 408 of the posterior support portion 312 and (ii) the central portion 302, thereby forming a region 410. The region 410 can be characterized as a tab 410 that extends from a perimeter defined by the lateral support portions 306 around the central portion 302. The tab 410 provides additional surface area to the posterior region of the flexible sealable member 106. The base 120 may include a similar tab 418 at an anterior end 416 distally located from a region 414 where the lateral support portions 306 meet the anterior support portion 310.

In some embodiments, the dimensions of the base 120 may be varied depending on the size of the flexible sealable member 106, e.g., as shown in FIGS. 18B-18I. In some embodiments, the longitudinal dimension of the base 120 may be longer than the lateral dimension of the base 120.

In some embodiments, the support member 118 comprises at least one material selected from the group consisting of polydioxanone, poly-L-lactide, poly-D-lactide, poly-DL-lactide, polyglycolide, ε-caprolactone, polyethylene glycol, and a copolymer thereof. In some embodiments, the material of the support member 118 is a copolymer of polydioxanone, poly-L-lactide, poly-D-lactide, poly-DL-lactide, polyglycolide, ε-caprolactone, and polyethylene glycol. In some embodiments, the copolymer includes (a) monomers of polydioxanone, poly-L-lactide, poly-D-lactide, poly-DL-lactide, polyglycolide, ε-caprolactone, or polyethylene glycol, and (b) one or more additional monomers. In some embodiments, the (a) and (b) monomers form a polymer that is bioabsorbable. One of ordinary skill in the art will appreciate that other suitable biodegradable material may be employed.

In some embodiments, the support member 118 comprises a threaded portion.

The threaded portion provides a region for the flexible sealable member 106 to load onto the support member 118. Without having to distort and/or deform the flexible sealable member 106 during assembly of the flexible sealable member 106 onto the support member 118, the risk of damage to the flexible sealable member 106 during manufacturing is reduced. The threaded portion may include a protrusion that encircles the body of the column 122. In some embodiments, the protrusion includes a gap. In some embodiments, the protrusion has a greater diameter than that of the column 122.

In some embodiments, the support member 118 may include a locator 126 to prevent the dislodgement of the flexible sealable member 106 from the sealing position, when hydraulic pressure of a blood vessel is relatively low. The locator 126 may provide a means to compress the implant into a vessel (e.g., by an operator). In some embodiments, the column 122 of the support member 118 has an engagement portion 124 to secure the locator 126 (e.g., an insertable or engagable pin or cage) to the support member 118.

Other examples of the support member are described in U.S. Patent Application Publication Nos. 2013/0274795, and 2016/0174953, the contents of which are incorporated by reference herein in their entirety.

Locator

In some embodiments, the locator 126 is maintained at a location relative to the exterior surface of the tissue when the closure device 100 is in the sealing position. In some embodiments, the locator 126 compresses against the exterior surface of the tissue when the closure device 100 is in the sealing position. In some embodiments, the locator 126 is moveable, from a stowed state to a deployed state, to engage exterior surface of the tissue adjacent the aperture such that a portion of the tissue is disposed between the locator 126 and the flexible sealable member 106 when the closure device 100 is in the sealing position. In certain embodiments, the engagement portion comprises a cavity in the column 122 to allow an extra-luminal pin (as the locator 126) to be inserted therethrough.

In some embodiments, the locator 126 may be an extra-luminal pin, as shown in FIGS. 7-11. In some embodiments, the extra-luminal pin prevents the implant being pushed off the luminal surface by application of extracorporeal pressure above the implantation site or due to patient movements. In some embodiments, the extra-luminal pin is deflected parallel to a blood vessel as it is advanced, as illustrated, e.g., in FIGS. 2 and 5. This deformation of the extra-luminal pin 80 helps secure it in its post deployment position.

In some embodiments, the locator may also be used to occlude the guidewire hole within the support member 118 when deployed. When deployed, an enlarged proximal portion of the locator may block a guidewire channel. In its proximal or retracted position, the locator may allow the guidewire 17 (shown in FIG. 3) to pass through the channel. When the locator is moved into its distal or deployed position, the channel does not align with the channel in the support member 118, thereby blocking the guidewire 17.

Figure 19A:
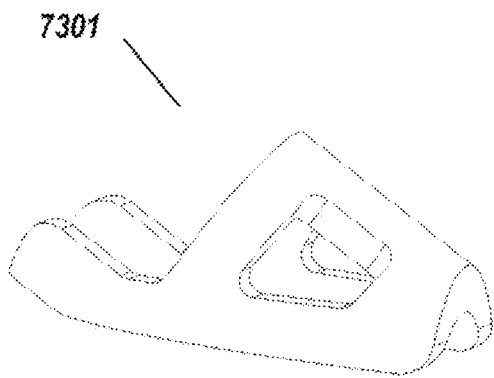
FIG. 19A is a diagram showing a perspective view of an exemplary extra-arterial locator.
Figure 19B:
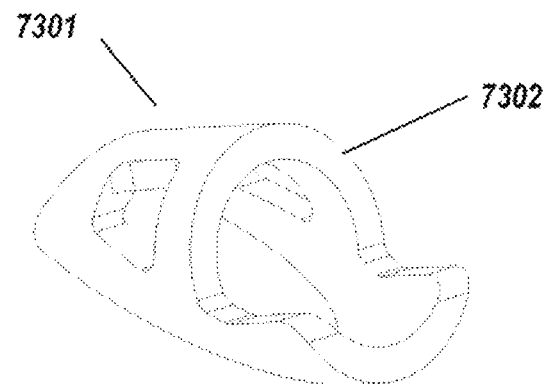
FIG. 19B is a diagram showing a perspective view of an exemplary extra-arterial locator.

In certain embodiments, the locator is a shoe 7301 as shown in FIGS. 19A and 19B. In certain embodiments, the locator has a caged structure and/or comprises one or more concave structural elements. In certain embodiments, the radius (e.g., inner radius) of a concave structural element corresponds to a radius of a surface of the column 122 or the support member 118, e.g., of a cylindrical portion of the column or the support member. In certain embodiments, the shoe comprises one or more engagement elements that can engage with a support member (e.g., an indentation, notch, hole, surface, slot, and/or groove). In certain embodiments, the shoe comprises a shoulder, e.g., shoulder 7302.

Figure 20A:
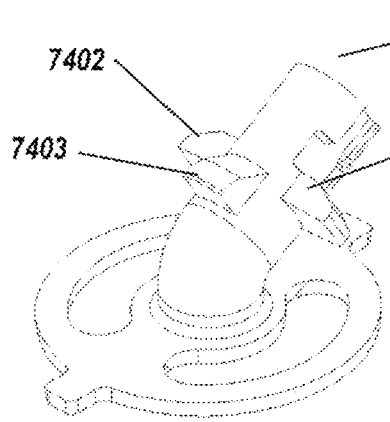
FIG. 20A is a diagram showing a view of a support member of the closure device, according to an illustrative embodiment.
Figure 20B:
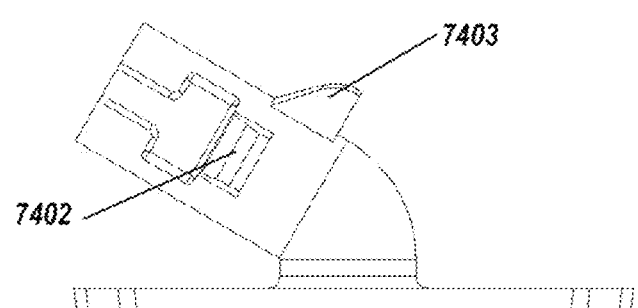
FIG. 20B is a diagram showing a view of a support member of the closure device, according to an illustrative embodiment.
Figure 20C:
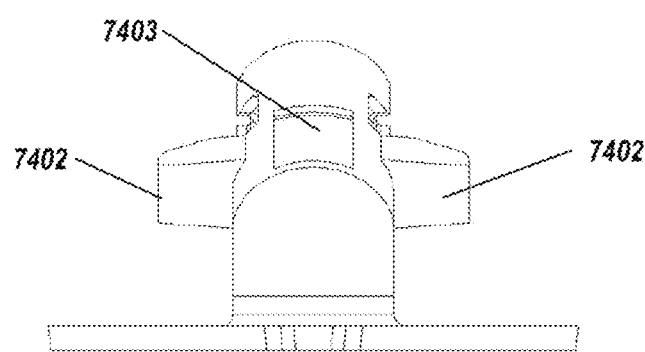
FIG. 20C is a diagram showing a view of a support member of the closure device, according to an illustrative embodiment.

In certain embodiments, a column 122 comprises tabs, e.g., as shown in FIGS. 20A-20C. In certain embodiments, a tabbed column, e.g., tabbed column 7401, comprises one or more locking tabs 7402, and/or one or more centering tabs 7403. In certain embodiments, a tabbed column comprises 1, 2, 3, 4, 5, or more locking tabs. In certain embodiments, a tabbed column comprises 1, 2, 3, 4, 5, or more centering tabs. The locking tabs and/or the centering tabs can be positioned anywhere on the tabbed column. In certain embodiments, the tabbed column comprises one centering tab and two locking tabs. In certain embodiments, the locking tabs are positioned opposite to each other along the circumference of a cylindrical portion of the tabbed column. In certain embodiments, the one or more locking tabs and the one or more centering tabs are aligned. In certain embodiments, a centering tab is a locking tab. In certain embodiments, the locking tabs "lock" with a feature of the cage or shoe (e.g., an engagement element, e.g., an indentation, notch, hole, surface, slot, and/or groove) when the locator is deployed and fully engaged, e.g., the locking tabs snap fit with the locator. In certain embodiments, the locking tabs "lock" in behind the shoulder of the shoe when the locator is deployed and fully engaged, e.g., the locking tabs snap-fit with the locator. In some embodiments, the centering tab or tabs can prevent the shoe biasing to one side of the implant, e.g., by preventing the shoe from rotating around the longitudinal axis of column 122. In certain embodiments, the one or more centering tabs engage an interior surface or interior portion or interior feature of the locator. In certain embodiments, the one or more centering tabs engage the shoulder of the locator. In certain embodiments, the one or more centering tabs can prevent the shoe biasing to one side of the implant, e.g., by reversibly engaging one or more features (e.g., notch, hole, surface, slot, and/or groove) of the locator. In certain embodiments, the one or more centering tabs engage an interior surface, or interior portion, or one or more interior features (e.g., notch, hole, surface, slot, and/or groove) of the cage or shoe. Without wishing to be bound by theory, if the locator were to move from its intended final position, e.g., toward one side of the implant, one or more of the locking tabs could potentially disengage from the cage or shoe releasing the implant.

Figure 21:
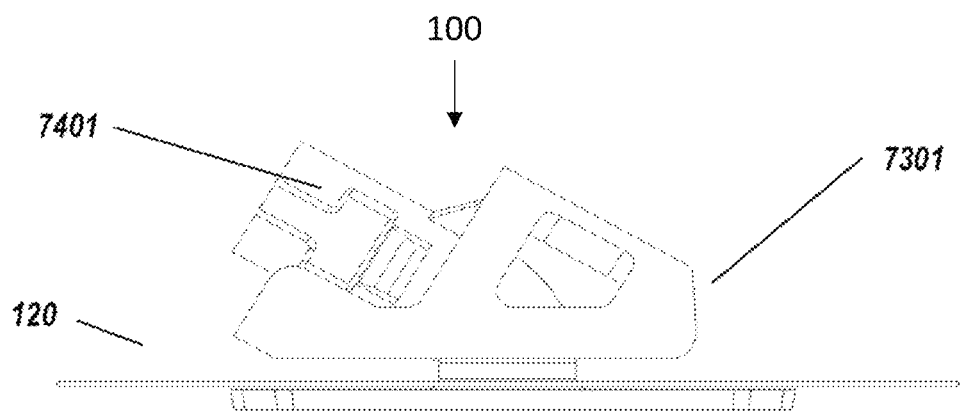
FIG. 21 is a diagram of an exemplary extra-arterial locator engaged with a support member of the closure device, according to an illustrative embodiment.

FIG. 21 depicts the locator 7301 deployed on an exemplary tabbed column 7401 according to an exemplary embodiment. In certain embodiments, the locator can secure a vascular closure device (VCD) implant to a blood vessel and/or help maintain the seal, e.g., of an arteriotomy or a veinotomy, e.g., by compressing the wall of an artery or vein between it and a base 120.

Figure 22A:
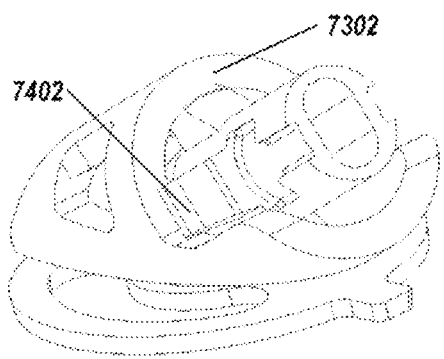
FIG. 22A is a diagram showing a view of a support member of the closure device, according to an illustrative embodiment.
Figure 22B:
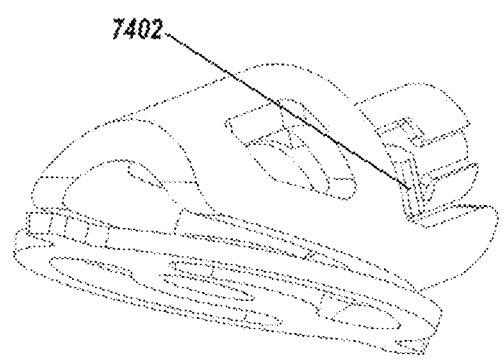
FIG. 22B is a diagram showing a view of a support member of the closure device, according to an illustrative embodiment.
Figure 22C:
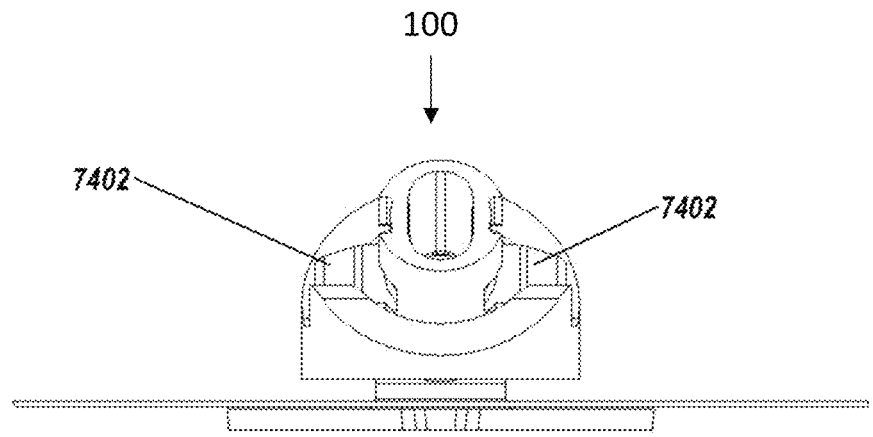
FIG. 22C is a diagram showing a view of a support member of the closure device, according to an illustrative embodiment.

FIGS. 22A-22C depict the locator 7301 engaged with an exemplary tabbed support member 7401 according to an exemplary embodiment. In certain embodiments, one or more locking tabs 7402 engage the shoulder of the locator (e.g., locator 7301). In certain embodiments, two locking tabs 7402 engage the shoulder of the locator as shown. In certain embodiments, a centering tab engages an interior surface or interior portion or one or more interior features (e.g., notch, hole, surface, and/or groove) of the locator.

Figure 23:
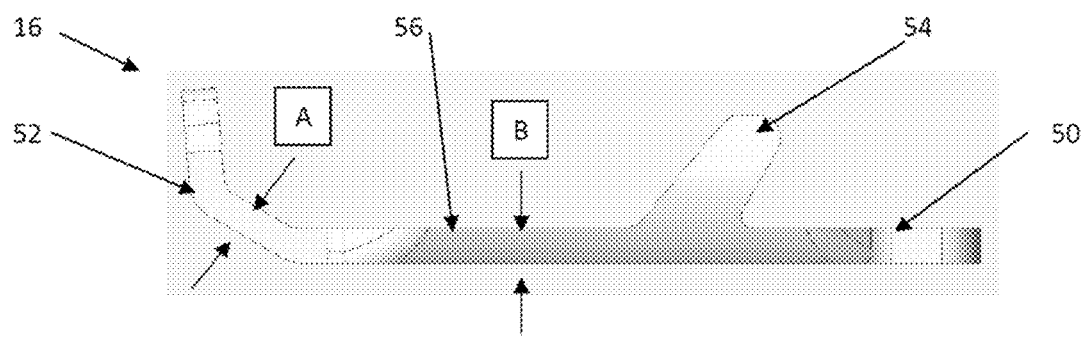
FIG. 23 is a cross-sectional view of a locator for use with a device in accordance with one or more embodiments of the invention.
Figure 24:
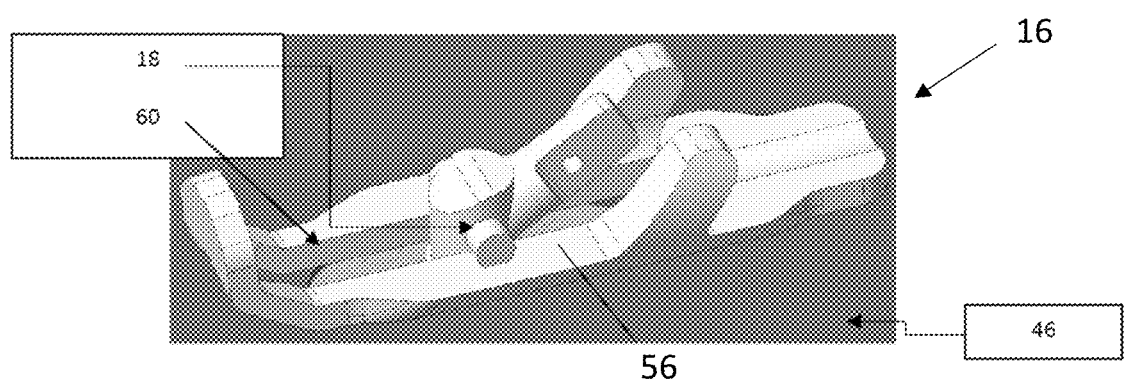
FIG. 24 is a perspective view of an alternative locator for use with a device in accordance with one or more embodiments of the invention.

In some embodiments, the locator 16 has an elongated body as shown in FIGS. 23-31. In some embodiments, the locator is substantially planar, a non-planar distal end 52 disposed at the front of the locator 16, and a guide mechanism 54 that extends upwardly from a top surface 60 of the locator to movably (e.g., slidably) engage the delivery tool. Generally, the front of the locator 16 has an angled face that protrudes out of the vessel puncture site when the sealable member is in contact with the vessel wall. This non-planar portion can include any combination of angled and/or arcuate shapes as necessary to suit a particular application. The purpose of this non-planar face is to ensure that the locator 16 passes over the vessel wall during deployment and is not deployed inside the wall. The locator 16 provides some flexibility so it can flex and bend to allow it to pass over the vessel wall without deforming or causing damage to the vessel tissue during the deployment. The locator 16 may include two longitudinal members 56, one on each side with a space therebetween, the longitudinal members 56 providing structure and allowing space for the support shaft 18 to be inserted therebetween, as shown in FIGS. 23 and 24.

At least a portion (e.g., A in FIG. 23) of the locator distal end 52 has a narrower cross-section than the main portion (e.g., B in FIG. 23) of the elongated body 50. This narrower area provides clearance for the locator 16 to be deployed between the support shaft 18 and the base 120. This clearance is to allow the locator to bend and flex as it advances over the vessel wall. FIG. 24 depicts the locator 16 engaged with the support shaft 18 and in a deployed position. Generally, the device achieves closure by positioning the flexible sealable member 106 against the vessel wall 46 between the locator 16 and the base 120. The locator 16 is held in place by the support shaft 18 and its positioning relative to the vessel wall and the cross-sectional area at location B as shown in FIGS. 23 and 24.

Various alterations can be made to the locator 16 design (e.g., adding ramp or spring-like features) to allow the device 10 to close apertures in vessel walls of various thickness and topography. These alterations increase the range of wall thickness that the device may be used to close in the vessel wall.

Figure 25:
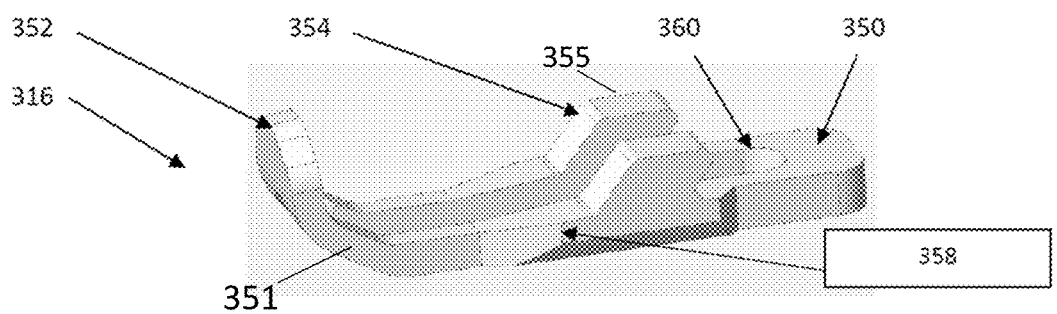
FIG. 25 is a perspective view of another alternative locator for use with a device in accordance with one or more embodiments of the invention.
Figure 26:
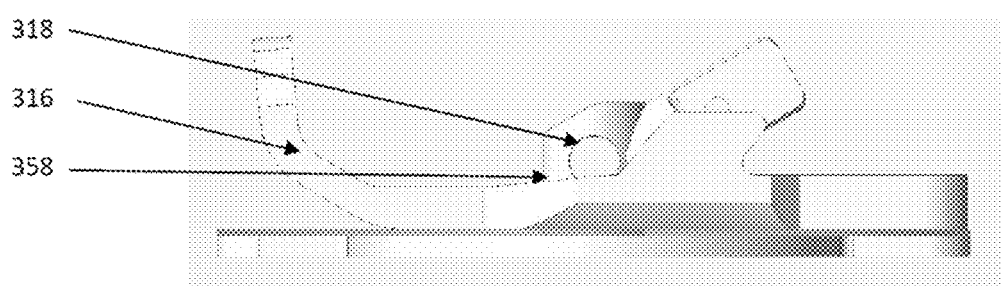
FIG. 26 is a side view of another alternative locator for use with a device in accordance with one or more embodiments of the invention.

FIGS. 25 and 26 depict a locator 316 where a portion of the top surface 360 has a ramped profile (e.g., adjustment mechanism 358) to increase the interference fit with the support shaft 318. In some embodiments, the locator 316 includes a first angled portion 351 extending at an angle from the planar elongated body 350, as well as a second angled portion 352 extending from the first angled portion 351, and at a steeper angle than the angle of the first angled portion 351 (relative to the plane of the planar elongated body 350), as shown in FIG. 25, and also FIGS. 23, 24, and 26. The locator 316 may also include angled guide portion 354 extending upwardly from the plane defined by the planar elongated body 350, the angled guide portion comprising a planar top portion 355 that is substantially parallel (for example, within 5 degrees of parallel) to the planar elongated body 350. FIG. 25 depicts the locator 316 alone, while FIG. 26 depicts the locator 316 engaging the support shaft 318.

Figure 27:
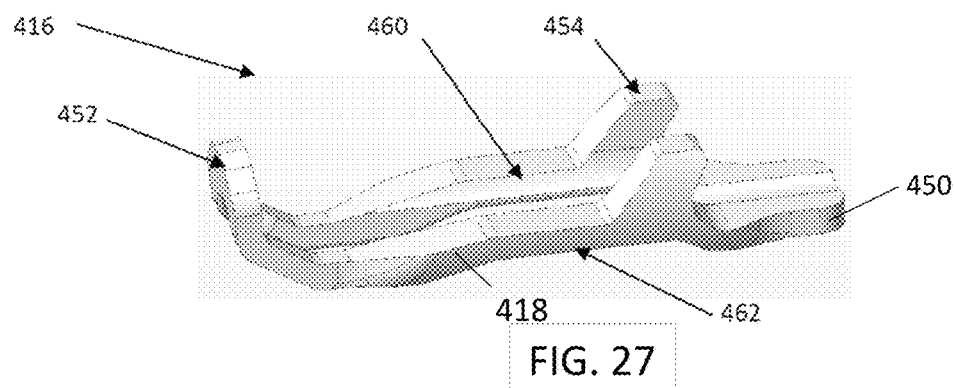
FIG. 27 is a perspective view of another alternative locator for use with a device in accordance with one or more embodiments of the invention.
Figure 28:
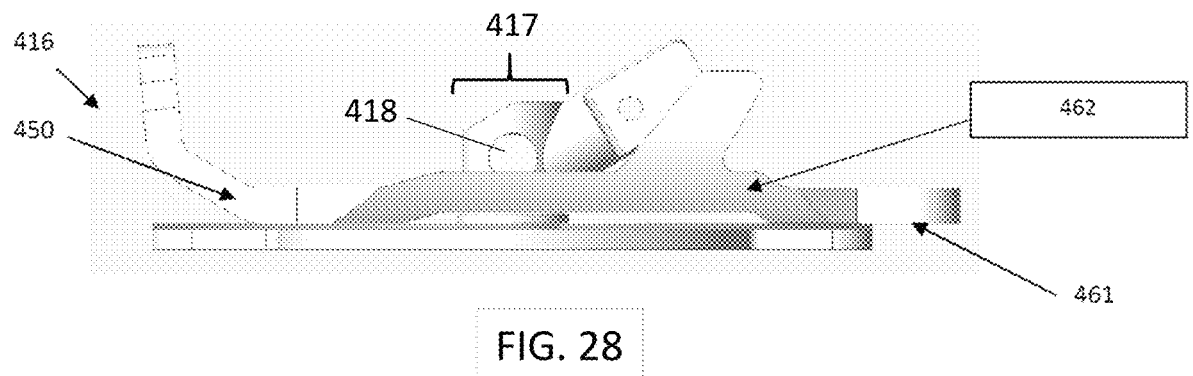
FIG. 28 is a side view of the alternative locator of FIG. 27 engaging with a support member in accordance with one or more embodiments of the invention.
Figure 29:
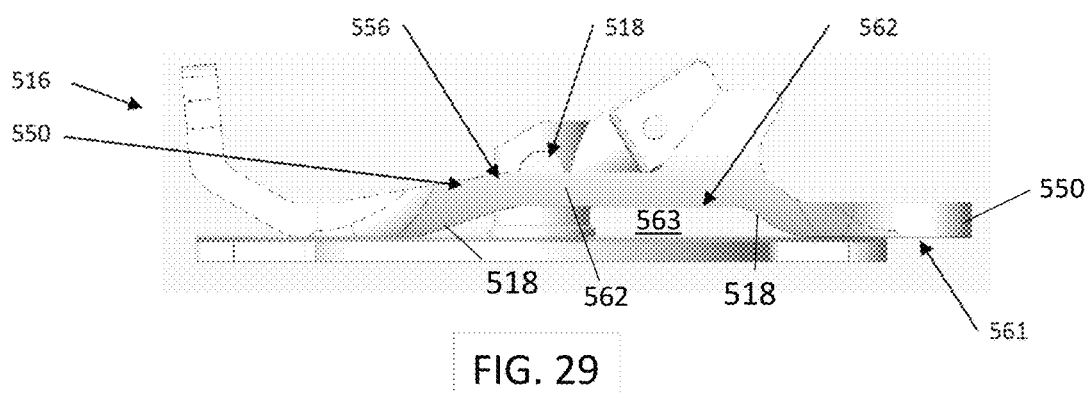
FIG. 29 is a side view of an alternative embodiment of the locator of FIG. 27 engaging with a support member in accordance with one or more embodiments of the invention.

FIGS. 27-29 depict a locator 416, 516 where a portion of the elongated body 450, 550 is non-planar. As shown in the figures, the portion of the elongated body that engages with the support shaft 418, 518 has an arcuate or angled portion (adjustment mechanism 462, 562) that defines a space 563 between a bottom surface 461, 561 of the elongated body and an outer surface of the vessel wall. FIG. 27 depicts the locator 416 alone, while FIG. 28 depicts the locator 416 with a first profile, and FIG. 29 depicts the locator 516 with a second, larger profile. These profiles can include any combination of arcuate and/or angled portions as necessary to suit a particular application and provide a spring force to the device. Specifically, the locator 416, 516 will act like a spring and pull the support member 417 up into the vessel wall via the support shaft 418, 518, as can be seen in FIGS. 28 and 29. FIG. 29 depicts a locator 516 with a more exaggerated spring profile (adjustment mechanism 562 defining a greater space 563 between the longitudinal members 556 and top surface of the vessel) that can provide a greater force and/or be more suitable for vessels with very thin walls. The locator 416 may include an angled guide mechanism 454 and an angled second portion 452, both protruding at an angle from the top surface 460.

Figure 30:
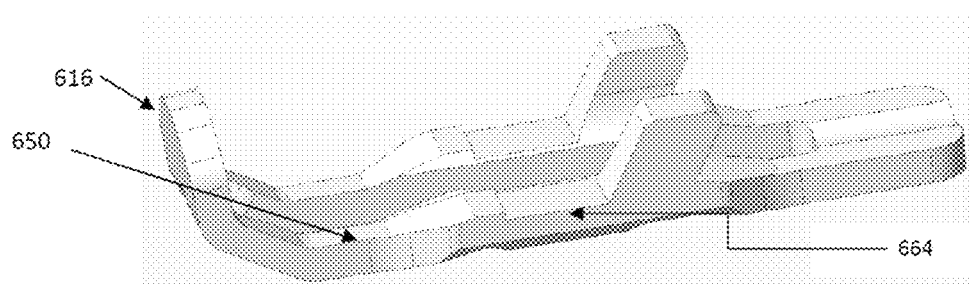
FIG. 30 is a perspective view of another alternative locator for use with a device in accordance with one or more embodiments of the invention.
Figure 31:
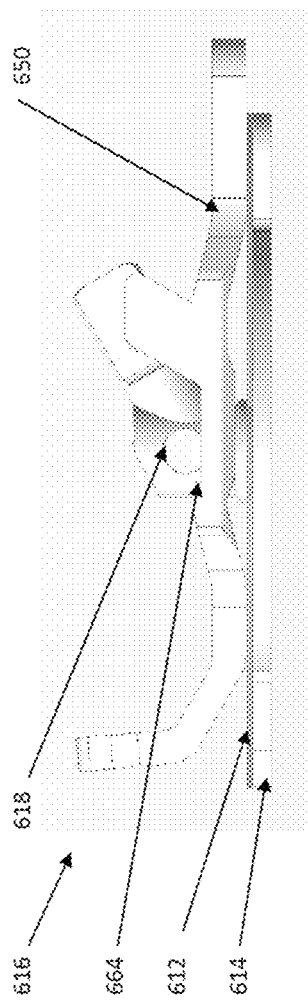
FIG. 31 is a side view of the alternative locator of FIG. 30 engaging with a support member in accordance with one or more embodiments of the invention.

FIGS. 30 and 31 depict a locator 616 where a portion of the elongated body 650 includes a cut-out (locator lock 664) in the top surface 660 of the elongated body 650. The lock 664 is located at a position on the elongated body 650 that substantially corresponds to where the locator 616 interfaces with the support shaft 618. The specific dimensions for the cut-out will vary to suit a particular application. FIG. 30 depicts the locator 616 alone, while FIG. 31 depicts the locator 616 engaged with the support shaft 618. The locator lock 664 can be used with any of the locator designs disclosed herein. As shown in FIG. 31, once deployed with the base member 614 sandwiching the flexible member 612 against the inner wall of the vessel, the support shaft 618 is locked within the cut-out to prevent movement of the locator relative thereto.

Figure 32A:
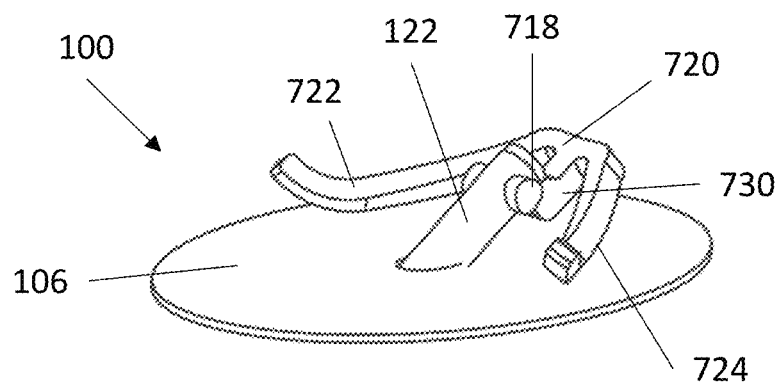
FIG. 32A is a perspective view of another alternative locator in accordance with one or more embodiments of the invention.
Figure 32B:
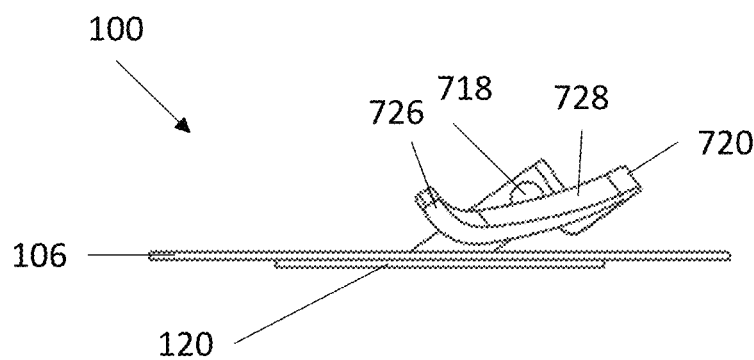
FIG. 32B is a side view of the alternative locator of FIG. 32A.
Figure 32C:
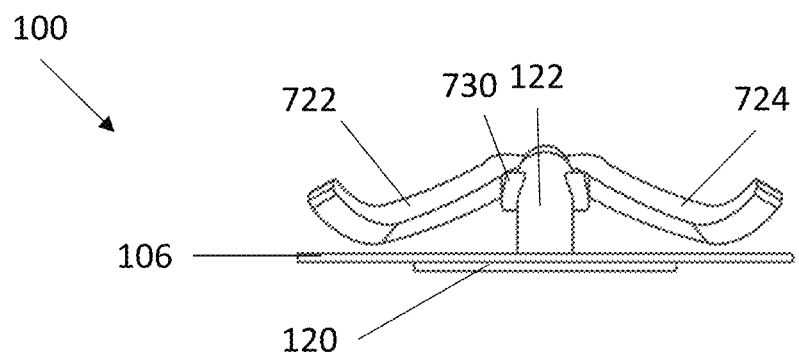
FIG. 32C is a front view of the alternative locator of FIG. 32A.
Figure 33A:
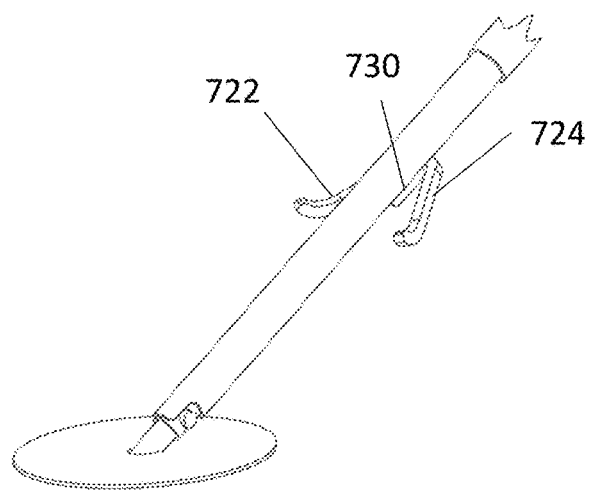
FIG. 33A illustrates a view of the alternative locator of FIG. 32A, engaging with a delivery device in accordance with one or more embodiments of the invention.
Figure 33B:
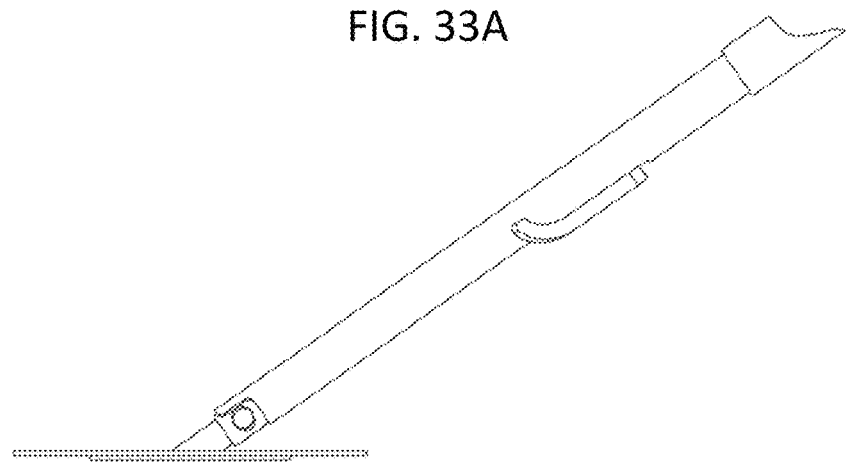
FIG. 33B illustrates a view of the alternative locator of FIG. 32A, engaging with a delivery device in accordance with one or more embodiments of the invention.
Figure 33C:
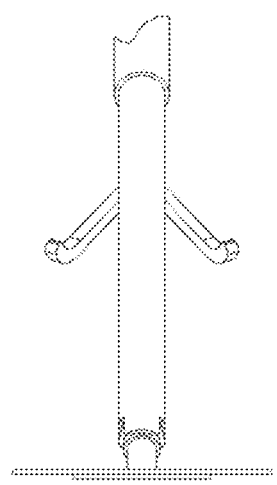
FIG. 33C illustrates a view of the alternative locator of FIG. 32A, engaging with a delivery device in accordance with one or more embodiments of the invention.
Figure 33D:
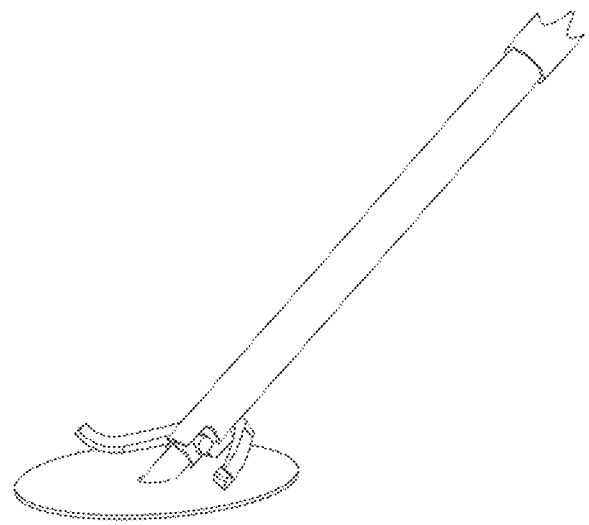
FIG. 33D illustrates a view of the alternative locator of FIG. 32A, engaging with a delivery device in accordance with one or more embodiments of the invention.
Figure 33E:
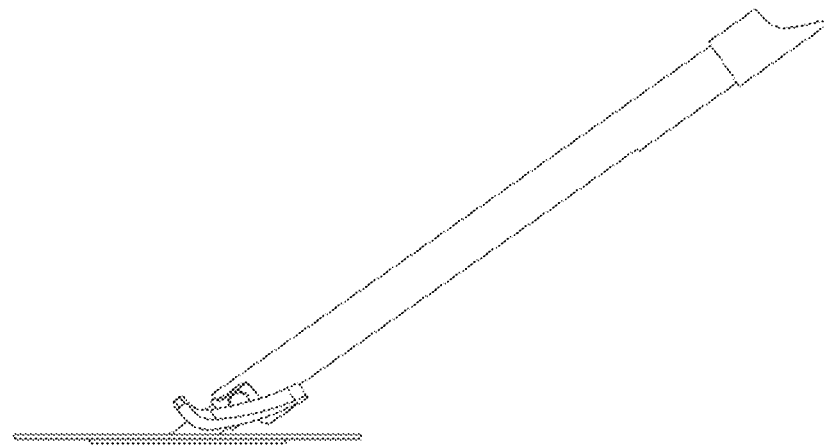
FIG. 33E illustrates a view of the alternative locator of FIG. 32A, engaging with a delivery device in accordance with one or more embodiments of the invention.
Figure 33F:
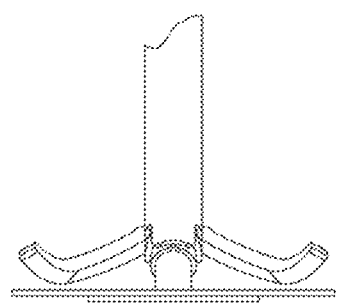
FIG. 33F illustrates a view of the alternative locator of FIG. 32A, engaging with a delivery device in accordance with one or more embodiments of the invention.
Figure 34A:
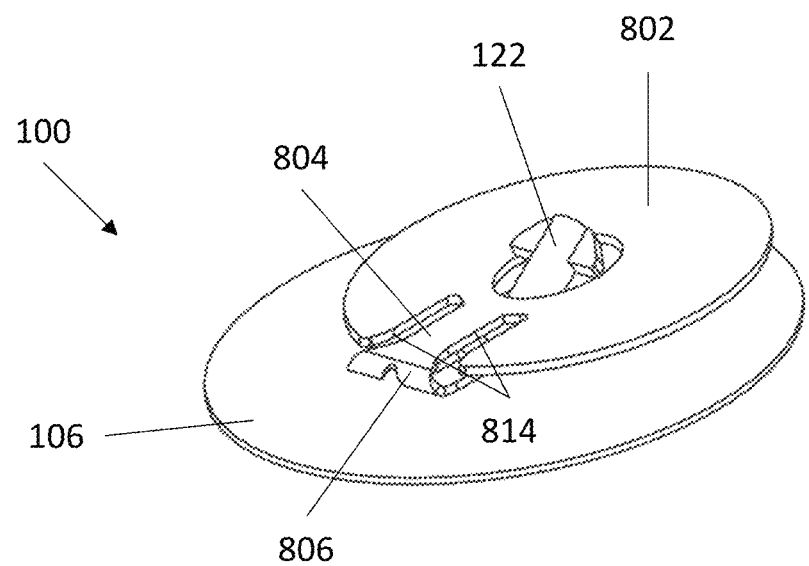
FIG. 34A is a perspective view of another alternative locator in accordance with one or more embodiments of the invention.
Figure 34B:
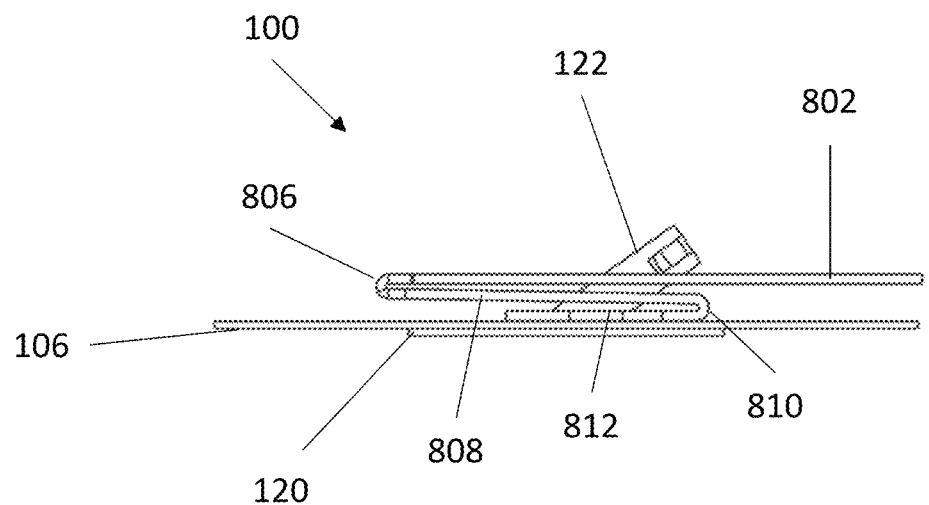
FIG. 34B is a side view of the alternative locator of FIG. 32A.

In some embodiments, the locator comprises open prongs 722, 724, as shown in FIGS. 32A-32C. In some embodiments, the locator comprises a back portion 720 that connects the open prongs 722, 724 together. When the implantable device 100 is in a sealing position, the open prongs 722, 724 are positioned at the external surface of the tissue nearby the aperture. In some embodiments, the open prongs 722, 724 of the locator provide counter tension on the flexible sealable member against the inner lumen wall by engaging with the tissue tract and/or external vessel wall during and/or after the deployment of the implantable device. In some embodiments, the locator comprises more than one open prong.

In some embodiments, the open prongs 722, 724 comprise two angled faces 726, 728. The purpose of the angled faces 726, 728 is to ensure that the locator passes over the vessel wall during deployment and is not deployed inside the wall. In some embodiments, the front angled face 726 is shorter than the back angled face 728. In some embodiments, the angle between the front angled face 726 and the back angled face 728 is within a range of about 90 degrees to 175 degrees. In some embodiments, the angle between the front angled face 726 and the flexible sealable member 106 (e.g., when the implantable device 100 is in a sealing position) is within a range of about 5 degrees to 45 degrees. In some embodiments, the angle between the back angled face 728 and the flexible sealable member 106 (e.g., when the implantable device 100 is in a sealing position) is within a range of about 5 degrees to 45 degrees.

In some embodiments, the sizes of the open prongs 722, 724 may be varied e.g., depending on the size of the flexible sealable member 106 and/or the aperture. In some embodiments, the length of each of the open prongs 722, 724 (e.g., when projected to the surface of the flexible sealable member) is about 30 to 80% of the longitudinal dimension of the flexible sealable member 106. In some embodiments, the thickness of the open prongs 722, 724 is uniform. In some embodiments, the thickness of the open prongs 722, 724 is about 300% to 1000% of the thickness of the flexible sealable member 106.

In some embodiments, two open prongs 722, 724 have the same shape, so that they are symmetric from the perspective of the centerline of the column 122 (e.g., see FIG. 32C). In some embodiments, the angel between two open prongs 722 (e.g., when projected to a center plane of the column 122 in FIG. 32C) is within a range of 90 degrees to about 175 degrees.

Still referring to FIGS. 32A-32C, in some embodiments, the locator comprises a locker 730. The locker 730 extends from the back portion 720 toward the center of the locator. When the implantable device 100 is in a sealing position, the locker 730 positions under the support shaft 718, but above the external surface of the tissues near the aperture, the flexible sealable member 106, and the base 120. In some embodiments, the locker 730 is shaped to click on the support shaft 718 and/or the column 122.

FIGS. 33A-33F show the delivery process of the implantable device 100 comprising the locator having open prongs 722, 724. In some embodiments, the open prongs 722, 724 are in their open position when the implantable device 100 is in its package (e.g., before deployment). During deployment, the open prongs 722, 724 are folded into a loading catheter while the flexible sealable member 106 is also rolled to a size less that the size of the vessel hole to be treated. When the implantable device 100 within its delivery catheter is located to the vessel lumen proximal to the hole, the flexible sealable member 106 and the base 120 are unsheathed and opens up in the vessel. The flexible sealable member 106 and the base 120 are then positioned against the inner lumen at the hole. Next, the open prongs 722, 724 open out as they are delivered distally along the delivery catheter to the outside of the vessel hole. As the open prongs 722, 724 are pushed distally, they engage with the distal tissue tract and/or the external vessel wall. Then, the open prongs 722, 724 are locked into the column 122. This locking step results in the locking of the locator relative to the intra-vessel parts of the implantable device 100 (e.g., the flexible sealable member 106, and the base 120). If required, closing of the guidewire hole which passes through the implant scaffold can be performed.

In some embodiments, the locator 16 is designed to have some flexibility so it can flex and bend to allow it to pass over the vessel wall without deforming or causing damage to the vessel tissue during the deployment.

In some embodiments, the locator comprises a flat disc 802 as shown in FIGS. 34A-34F. In some embodiments, the locator comprises a folding connector (e.g., comprising top portion 804, first folding position 806, middle portion 808, second folding position 810, bottom portion 812). The flat disc 802 is connected to the top portion 804 of the folding connector. In some embodiments, the bottom portion 812 is attached to the top surface of the flexible sealable member 106 (e.g., when the implantable device 100 is in sealing position, when the implantable device 100 is in sealing position not in sealing position). In some embodiments, the flat disc comprises one or more gaps 814 between the flat disc 802 and the top portion 804. In some embodiments, the lateral dimension of the flat disc 802 is about 50 to 90% of the lateral dimension of the flexible sealable member 106. In some embodiments, the thickness of the flat disc 802 is about 100 to 500% of the thickness of the flexible sealable member 106.

In some embodiments, when the device is in a sealing position, the folding connector folds twice, so that the bottom portion 812 is on the flexible sealing member 106, the middle portion 808 is on the bottom portion 812, the top portion 804 and the flat disc 802 is on the middle portion 808. The top portion 804 and the middle portion 808 are connected via the first folding position 806. The middle portion 808 and the bottom portion 812 are connected via the second folding position 810.

In some embodiments, the thickness of the folding connector is uniform. In some embodiments, the thickness of the folding connector is not uniform, e.g., the thickness of the folding positions is smaller than the thickness of the top portion 804, the middle portion 808 and/or the bottom portion 812. In some embodiments, the thickness of the folding connector is substantially similar to the thickness of the flat disc 802

In some embodiments, the length of the middle portion 808 is greater than the length of the top portion 804 and/or the bottom portion 812. In some embodiments, when the device is in a sealing position, the distance between the first folding position 806 and the second folding position 810 is greater than the longitudinal dimension of the base 120. In some embodiments, when the device is in a sealing position, the distance between the first folding position 806 and the second folding position 810 is substantially similar to the longitudinal dimension of the base 120. In some embodiments, when the device is in a sealing position, the distance between the first folding position 806 and the second folding position 810 is smaller than the longitudinal dimension of the flexible sealing member.

In some embodiments, the middle portion 814 comprises a longitudinal gap, so that the delivery shaft can pass through the middle portion 814. In some embodiments, the length of the middle portion 808 is substantially similar to the longitudinal dimension of the base 120. In some embodiments, the length of the middle portion 808 is about 30 to 80% of the longitudinal dimension of the base 120.

In some embodiments, the distance between the flexible sealing member and the tap in the column 122 is substantially similar to or slightly larger than the folded thickness of the folding connector (e.g., total thickness of the flat disc 802, the middle portion 808, the bottom portion 812 and the gaps therebetween), so that the locator secures the position of the implantable device.

In some embodiments, when the implantable device 100 is in a sealing position, the flat disc 802 is positioned at the external surface of the tissue nearby the aperture. In some embodiments, when the implantable device 100 is in a sealing position, a portion of the folding connector passes though the aperture. In some embodiments, when the implantable device 100 is in a sealing position, a portion of the folding connector is disposed below the aperture. In some embodiments, when the implantable device 100 is in a sealing position, a portion of the folding connector is disposed above the aperture.

In some embodiments, the locator comprises at least one material selected from the group consisting of polydioxanone, poly-L-lactide, poly-D-lactide, poly-DL-lactide, polyglycolide, ε-caprolactone, polyethylene glycol, and a copolymer thereof. In some embodiments, the material of the locator is a copolymer of polydioxanone, poly-L-lactide, poly-D-lactide, poly-DL-lactide, polyglycolide, ε-caprolactone, and polyethylene glycol. In some embodiments, the copolymer includes (a) monomers of polydioxanone, poly-L-lactide, poly-D-lactide, poly-DL-lactide, polyglycolide, ε-caprolactone, or polyethylene glycol, and (b) one or more additional monomers. In some embodiments, the (a) and (b) monomers form a polymer that is bioabsorbable. One of ordinary skill in the art will appreciate that other suitable biodegradable material may be employed.

Other examples of the locator are described in U.S. Patent Application Publication Nos. 2013/0274795, US 2014/0018847 and 2019/0021710, and PCT Application Publication No. WO2020/141122, the contents of which are incorporated by reference herein in their entirety.

Delivery Device

The methods and devices provided herein relate to delivery devices that are capable of delivering an implantable device 100 to close holes in hollow vessels. FIGS. 33-34 depict an embodiment of the delivery device. In certain embodiments, the delivery device comprises the parts listed in Table 1 below; the functionality of each part is described in further detail below.

TABLE 1

| Part Name | Detail |
|---|---|
| Introducer unit | Sheath and Dilator |
| Sheath | Sheath shaft, sheath hub, haemostasis valve and sheath retainer |
| Dilator | Dilator shaft and dilator hub |
| Loading Funnel | Protects implant in packaging and facilitates implant loading |
| Lever | Maintains attachment of loading funnel to loading cannula |
| Cannula | Cannula tube, cannula seal, cannula cap and cannula retainer |
| Cannula tube | Protects the implant during insertion through the sheath seal |
| Cannula seal | Seal in the cannula cap |
| Cannula retainer | Locks cannula tube and cannula seal inside the cannula cap |
| Cannula cap | Houses the cannula tube and cannula seal |
| Sheath carriage | Connects to cannula |
| Handle front L | Operator grip area of the delivery device |
| Handle front R | Operator grip area of the delivery device |
| Handle centre | Joins front and back of the delivery device |
| Sheath cam L | Actuates sheath carriage |
| Sheath cam R | Connected to sheath cam L |
| Handle end L | Houses hubs |
| Handle end R | Houses hubs |
| Cam lock | Locks back cam |
| Back cam L | Actuates release sleeve and push tube hubs |
| Back cam R | Allows re-setting of the delivery device |
| Shafts | Release sleeve, retainer sleeve & push tube |
| Release sleeve | Releases implant from the retainer sleeve |
| Release sleeve hub | Moves release sleeve |
| Retainer sleeve | Holds implant in position |
| Retainer sleeve hub | Holds retainer tube |
| Push tube | Tube to push the extra-arterial pin |
| Push tube hub | Moves push tube |

Implant Loading

Figure 35C:
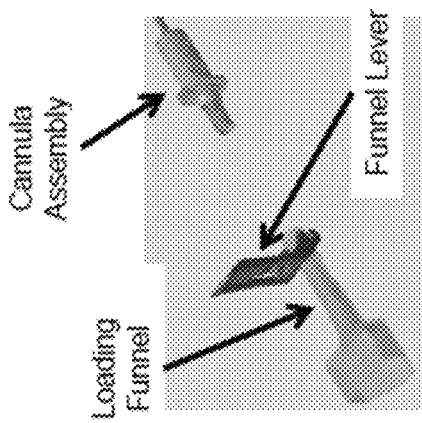
FIG. 35C depicts an image of an embodiment of a funnel-loading cannula cap arrangement with the funnel withdrawn from the loading cannula cap.
Figure 35B:
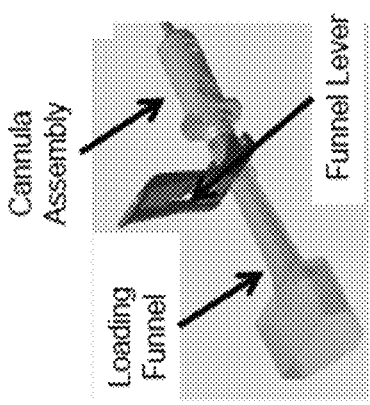
FIG. 35B depicts an image of an embodiment of a funnel-loading cannula cap arrangement with a lever detached from the loading cannula cap.
Figure 35A:
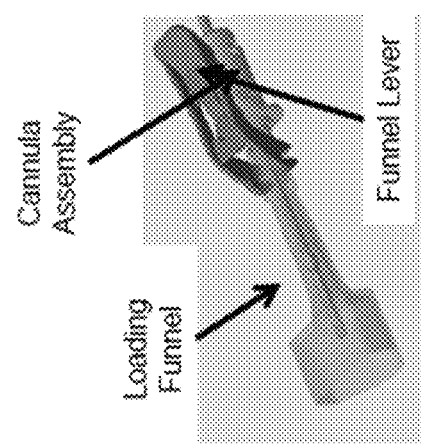
FIG. 35A depicts an image of an embodiment of a funnel-loading cannula cap arrangement with a lever latched onto the loading cannula cap.

In certain embodiments, a delivery system, e.g., as described herein, is packaged in a tray system, e.g., with the implantable device 100 located in the loading funnel. In certain embodiments, to load the implantable device, the delivery device is held by the back handle section and pulled to a physical and tactile feel stop in the tray. In certain embodiments, at this stage, the implantable device 100 is loaded into a (loading) cannula assembly (the cannula assembly and its components are described below). A funnel lever is then unlatched from the (loading) cannula cap, and the delivery device is withdrawn from the tray in a backward motion leaving the funnel and lever in the tray (see FIGS. 35A-C). In certain embodiments, the loading funnel is designed so as to ensure that the implant is folded concentrically (e.g., in an overlapping manner) as the implant is withdrawn backward into and/or through the funnel and loaded into the cannula.

Introducer Unit

The introducer unit comprises a sheath and dilator, and may have shafts of varying lengths, diameters, and/or French sizes. In certain embodiments, the introducer unit comprises a graduated scale on the sheath shaft (or sheath outer shaft) and a blood signal in the dilator shaft. In certain embodiments, when used in combination, these provide the operator with visual indicators of relative location of the introducer and the delivery device system during initial deployment of the sheath to the, e.g., arteriotomy, and again during the deployment of the implant. In certain embodiments, the graduated scale on the sheath shaft and the blood signal, used in combination, allow the operator to identify the position of the implant during deployment, and to deploy the implant in the correct or desired location. In certain embodiments, the dilator loads onto and/or travels over a guide wire (e.g., a 0.035" guide wire), which occupies the internal diameter of the dilator at the distal tip and proximal hub areas. In certain embodiments, the dilator contains a blood signaling hole in the hub which is fed from a blood signal hole located in close proximity (e.g., just distal) to the sheath tip, e.g., on the tapered portion of the dilator.

In certain embodiments, when the introducer unit (e.g., sheath and dilator) enters the, e.g., arteriotomy, (e.g., when the introducer is moved along the wire and the tip of the dilator enters an arteriotomy) blood enters the dilator at the blood signal hole (e.g., as soon as the blood signal hole on the distal tip of the dilator enters a blood vessel), and travels up the dilator's lumen, and exits the dilator at a signal hole (e.g., a blood signal detector hole) on the dilator hub. This signals to the operator that the sheath tip is just about to enter the, e.g., arteriotomy. The graduations on the sheath shaft can then provide to the operator an indication of the tissue tract depth, as this point on the graduated scale (at the skin level) indicates the depth of the tissue tract (mark X). From this point on the graduated scale (mark X), the introducer unit is advanced by a certain distance (4 cm) into the vessel to mark Y (going by the graduated scale on the sheath). The dilator is subsequently removed from the sheath, while maintaining the sheath at the 'Y' location in the vessel, and keeping the guidewire in its relative position.

Sheath Hub and Dilator

Figure 36A:
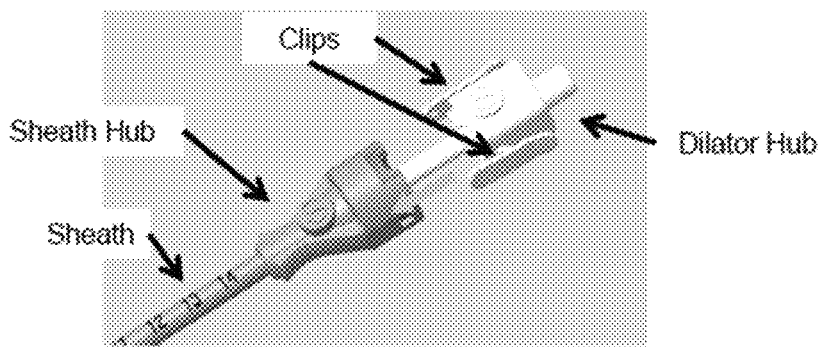
FIG. 36A depicts an image of a sheath hub and dilator hub connection, particularly the insertion of a dilator into an introducer sheath.
Figure 36B:
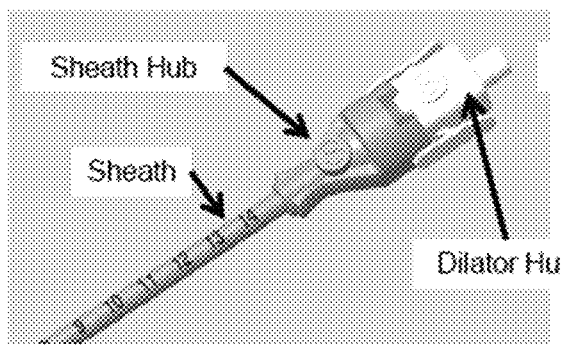
FIG. 36B depicts an image of a sheath hub and dilator hub connection with the dilator fully inserted into an introducer sheath.
Figure 36C:
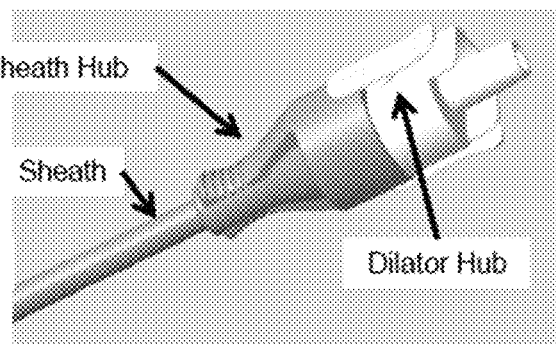
FIG. 36C depicts an image of a sheath hub and dilator hub connection, with the dilator fully inserted into an introducer sheath and with the dilator hub locked in the sheath hub.
Figure 36D:
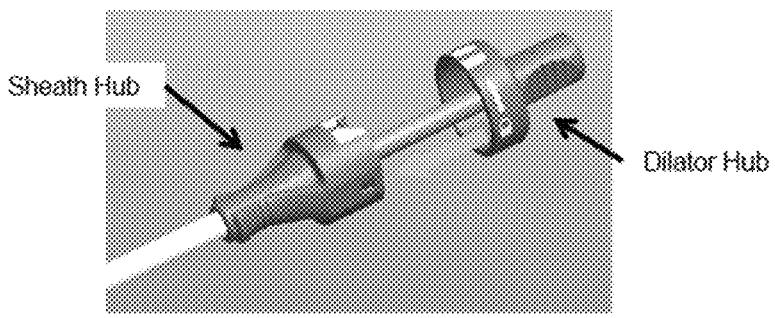
FIG. 36D depicts an image of a sheath hub and dilator hub connection, particularly the insertion of a dilator into an introducer sheath.
Figure 36E:
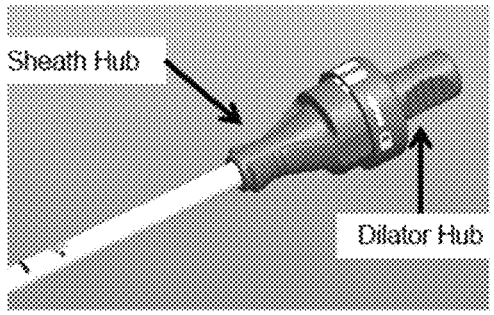
FIG. 36E depicts an image of a sheath hub and dilator hub connection with the dilator fully inserted into an introducer sheath.
Figure 36F:
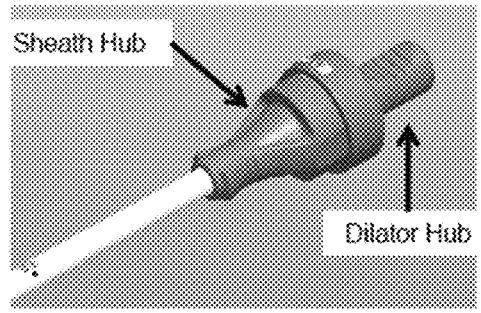
FIG. 36F depicts an image of a sheath hub and dilator hub connection, with the dilator fully inserted into an introducer sheath and with the dilator hub locked in the sheath hub.

In certain embodiments, the sheath hub is designed to connect with the dilator hub using, e.g., a spring clip mechanism (see, e.g., FIGS. 36A-8C) or a bayonet mechanism (see, e.g., FIGS. 36D-36F), wherein the dilator hub is pushed into the sheath hub and, e.g., engaged (e.g., clicked) and/or twisted to lock in position (FIG. 36F). In certain embodiments, e.g., in embodiments comprising a spring clip mechanism, tabs on the distal end of a spring clip mechanism latch onto, e.g., pockets on the sheath hub, holding both hubs firmly together. In certain embodiments, to separate the hubs, one or more proximal end or ends of a clip or clips is/are compressed, causing on or more tabs to exit their corresponding pocket on the sheath hub, allowing the dilator to be withdrawn from the sheath (see, e.g., FIGS. 36A-36C). In certain embodiments, the sheath hub is also designed to connect with the cannula. In certain embodiments, the haemostasis valve is secured into the sheath hub by the sheath retainer. In certain embodiments, the sheath retainer has snap features which align with snap features on the cannula cap to facilitate connection and locking into position.

Cannula

Figure 37A:
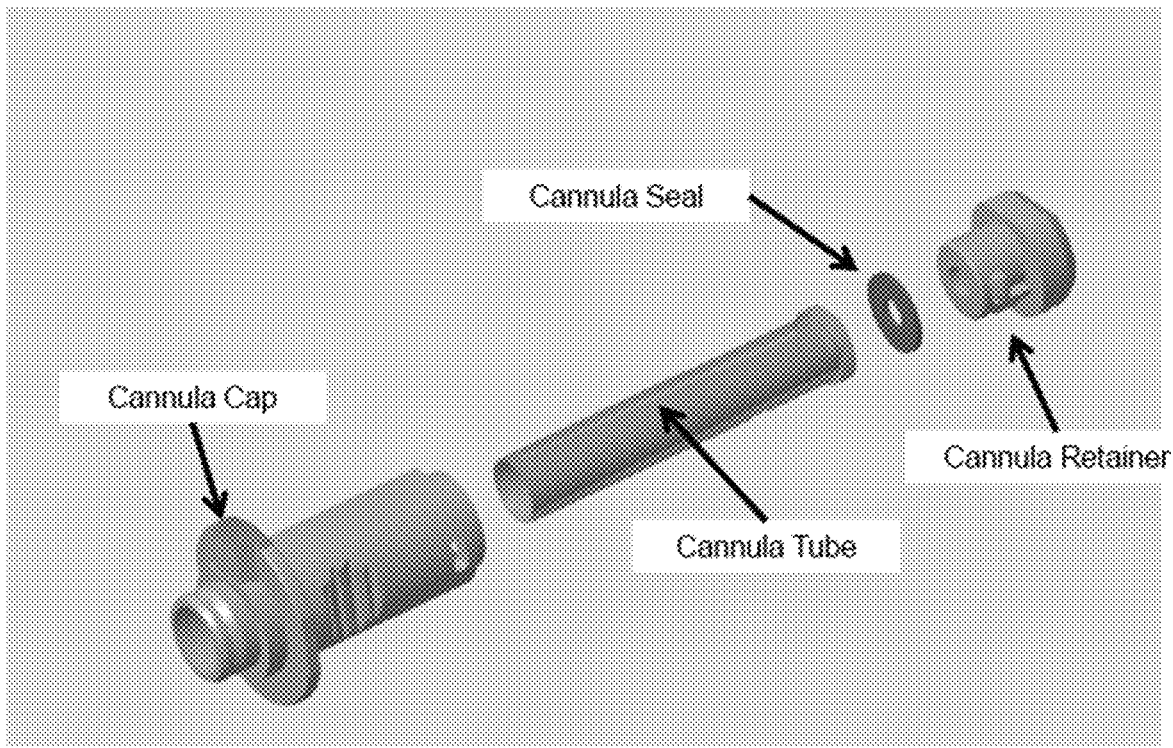
FIG. 37A depicts an image of an exploded view of a cannula assembly including a cannula cap, a tube, a seal, and a retainer.
Figure 37B:
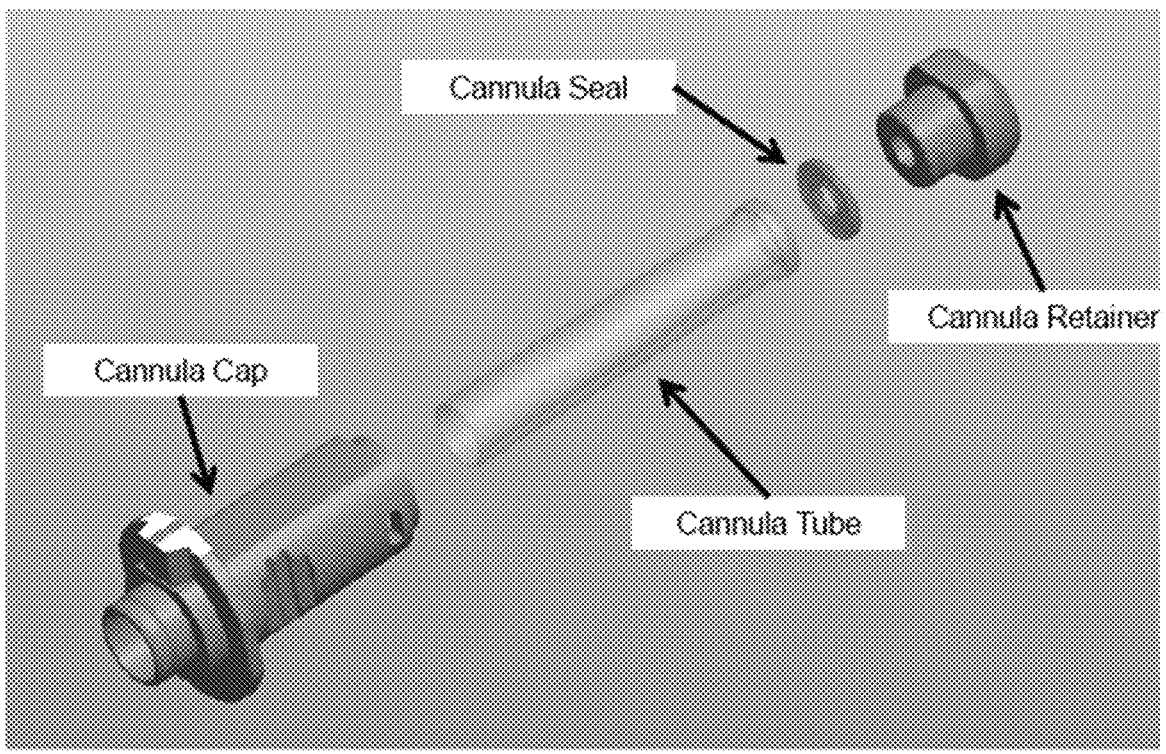
FIG. 37B depicts an image of an exploded view of a cannula assembly including a cannula cap, a tube, a seal, and a retainer.

In certain embodiments, the cannula or cannula assembly includes a cannula cap, cannula tube, cannula seal, and cannula retainer. The components can be seen, e.g., in FIGS. 37A and 38B. In certain embodiments, the cannula is part of the distal tip of the delivery device. In certain embodiments, the cannula is not part of the distal tip of the delivery device. In certain embodiments, the implant is loaded into the cannula from its resting position in the delivery device tray packaging. In certain embodiments, during the first steps of implant deployment, the cannula is connected to the hub of the introducer sheath. Next, the delivery device is advanced towards the introducer sheath hub and the implant is delivered down to a position just proximal to the distal tip of the introducer sheath. The cannula engages and locks into the introducer sheath hub to form a single unit. In certain embodiments, the implant is loaded into the cannula, which is assembled onto a tip of a shaft of the delivery device. When the cannula is connected to the sheath, the shafts of the delivery device are advanced to push the implant out of the cannula to the end of the sheath. The (cannula) seal functions to stop the blood from flowing out the back of the cannula along the shaft during deployment of the delivery device.

Sheath Withdrawal (Handle Front, Sheath Carriage, Cannula and Sheath)

Figure 38:
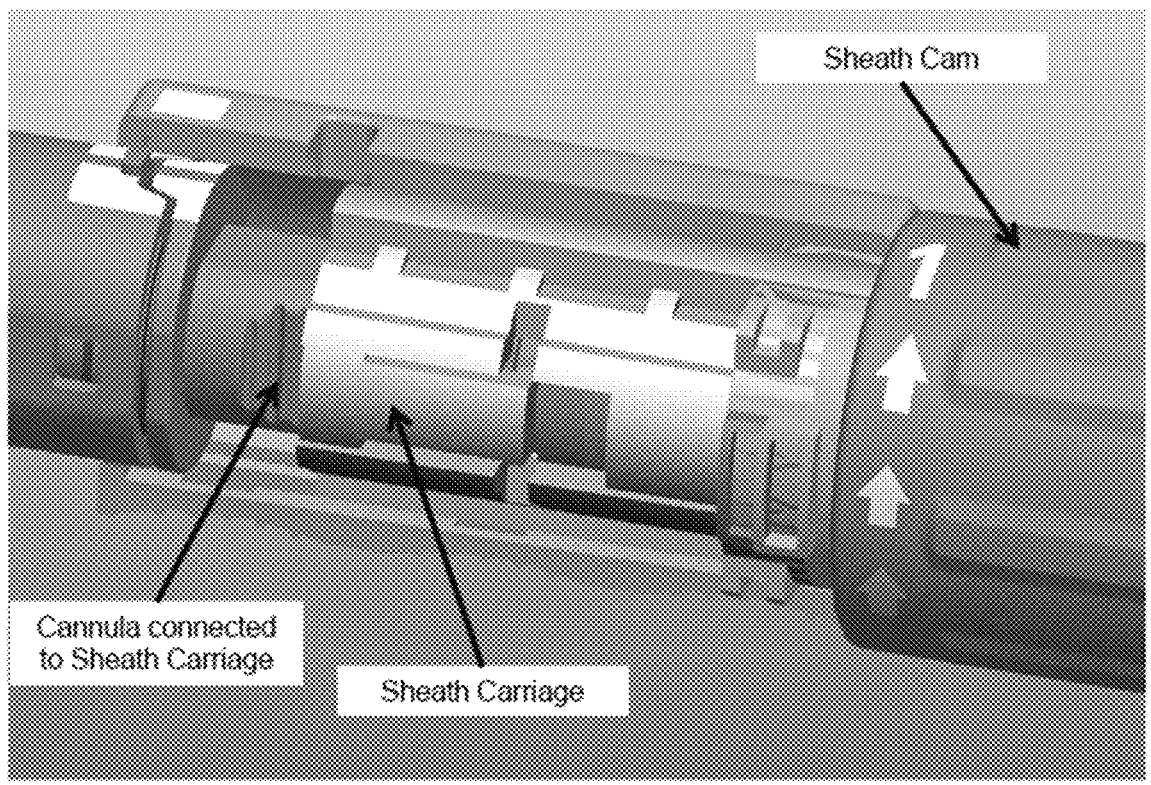
FIG. 38 depicts an image of a cannula and a sheath hub, wherein the cannula and sheath hub are connected into a sheath carriage.
Figure 39:
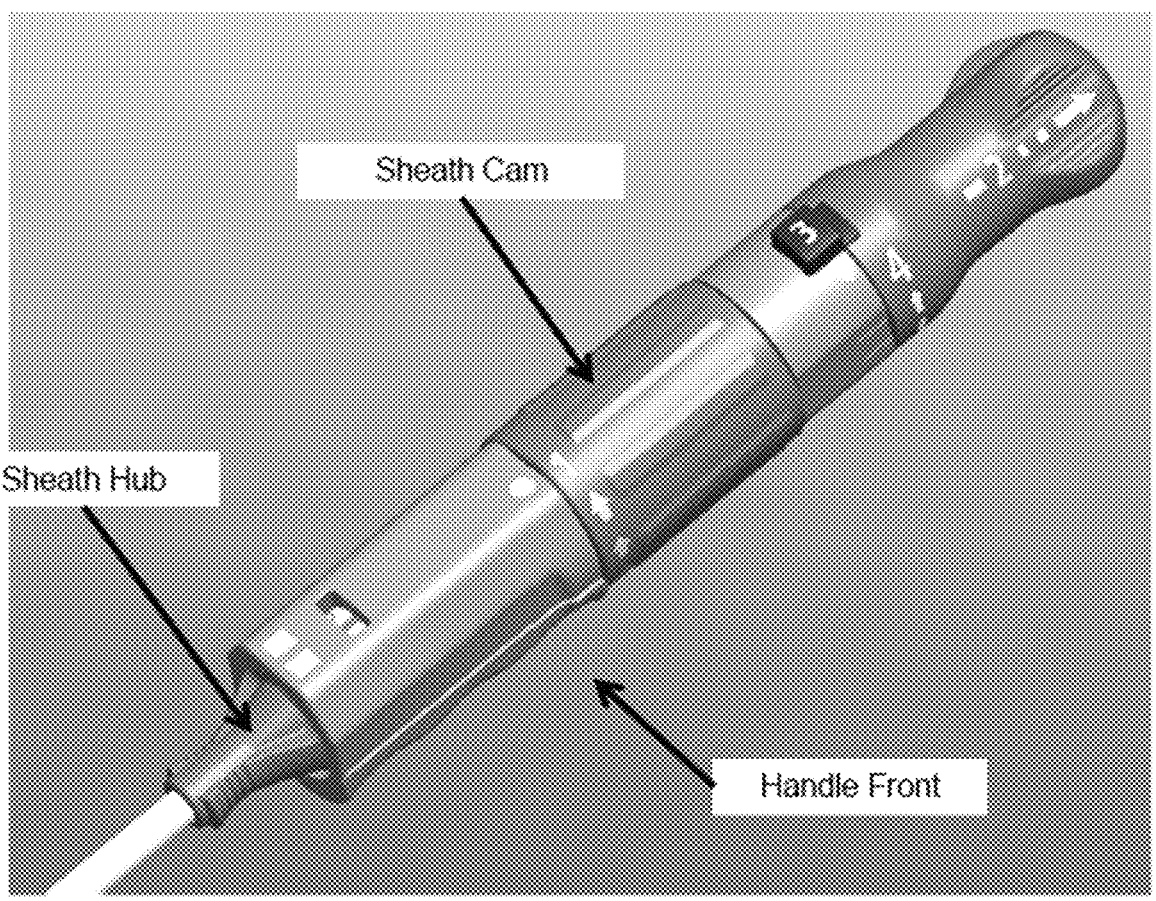
FIG. 39 depicts an image of a cannula and a sheath hub, wherein the cannula and sheath hub are connected into a sheath carriage inside the handle front.
Figure 40:
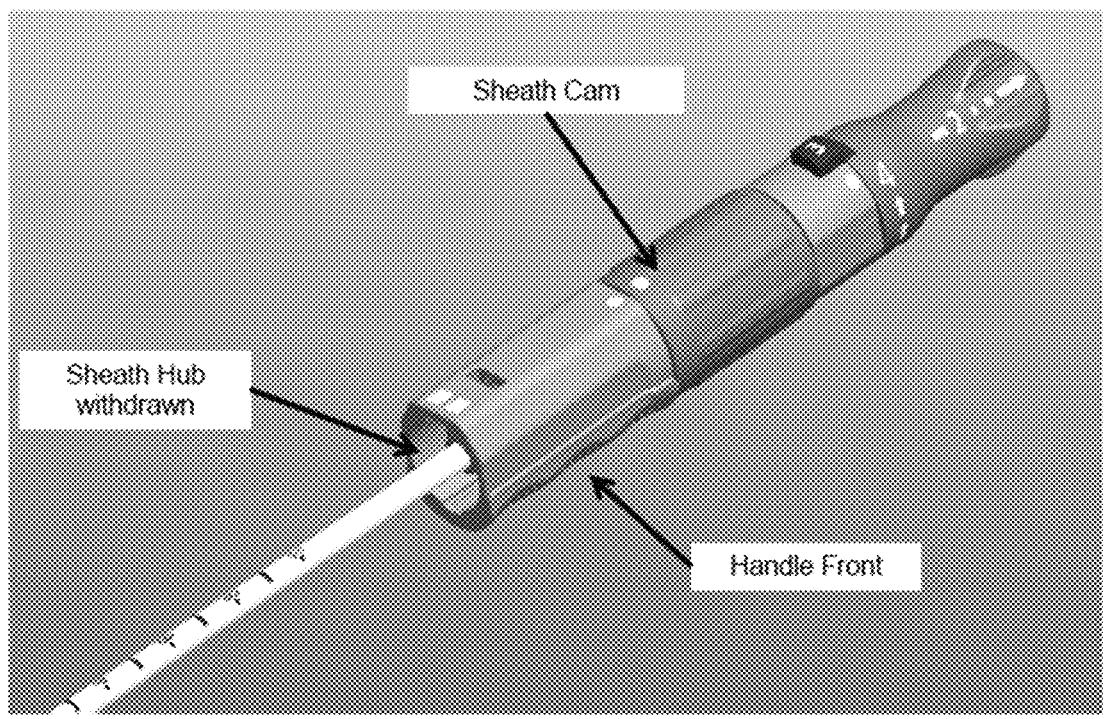
FIG. 40 depicts an image of a device assembly, wherein the sheath hub is withdrawn into the handle front.

In certain embodiments, the delivery handle is moved into close proximity to the introducer sheath hub. In certain embodiments, the cannula is designed to enter and lock and/or fit securely into the handle of the delivery device. The cannula (connected to the sheath) is moved back and connected into the sheath carriage inside the handle front as shown in FIG. 38 and FIG. 39. In certain embodiments, a sheath cam is engaged with the sheath carriage and is then rotated from a first position (FIG. 39) to a second position, e.g., clockwise 180° which in turn actuates the sheath carriage and pulls back the sheath into the handle front (see FIG. 40). In certain embodiments, the result of this action is, for example, to expose the implant in the vessel in an atraumatic way by pulling the introducer sheath assembly in the proximal direction relative to the delivery handle. In certain embodiments, the user then (e.g., gradually) withdraws the delivery device and sheath (assembly) (e.g., fully or partially) together from the artery (or other vessel, such as a vein), watching the graduations on the sheath until the mark X is reached. In certain embodiments, when the mark X on the graduated scale is reached, the user can feel the sheath tip exit the arteriotomy (or other vessel incision or access point) and within a certain distance (e.g., 1.5 cm) further withdrawal, can feel a back pressure as a result of the implant anchoring itself against the inside of, for example, a lumen of an artery wall (or other vessel, such as a vein) (this is the tamponade position).

Release of the Bioabsorbable Implant (Handle End, Cam Lock, and Back Cam)

Figure 41:
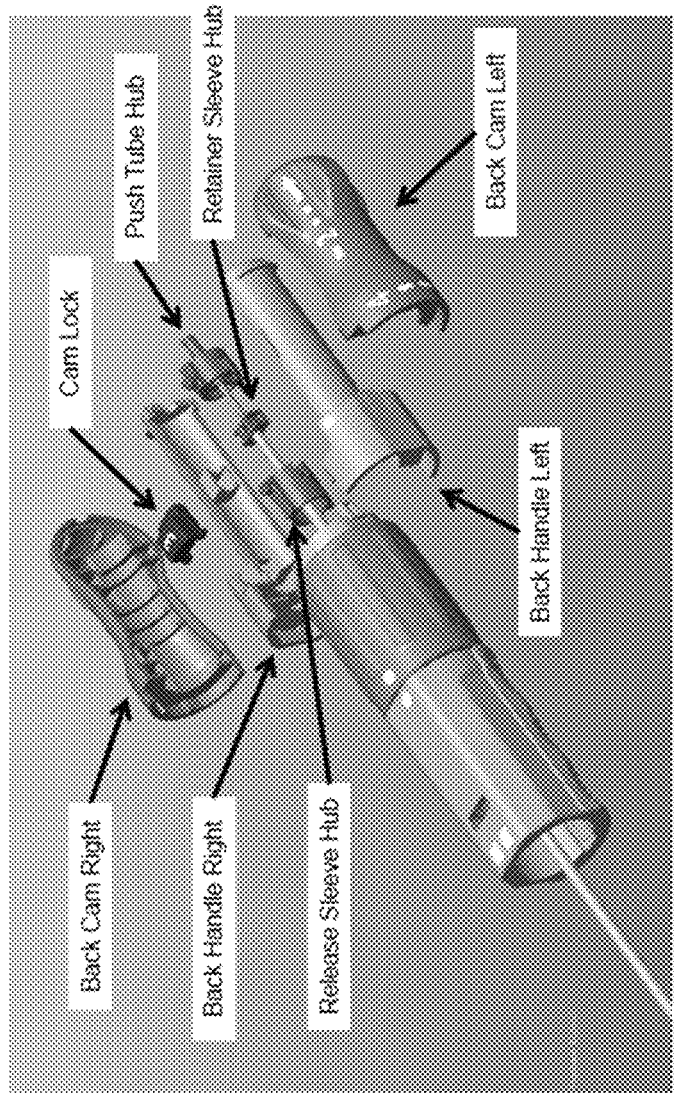
FIG. 41 depicts an image of an exploded view of shaft hubs, handle ends, a cam lock, and a back cam.
Figure 42:
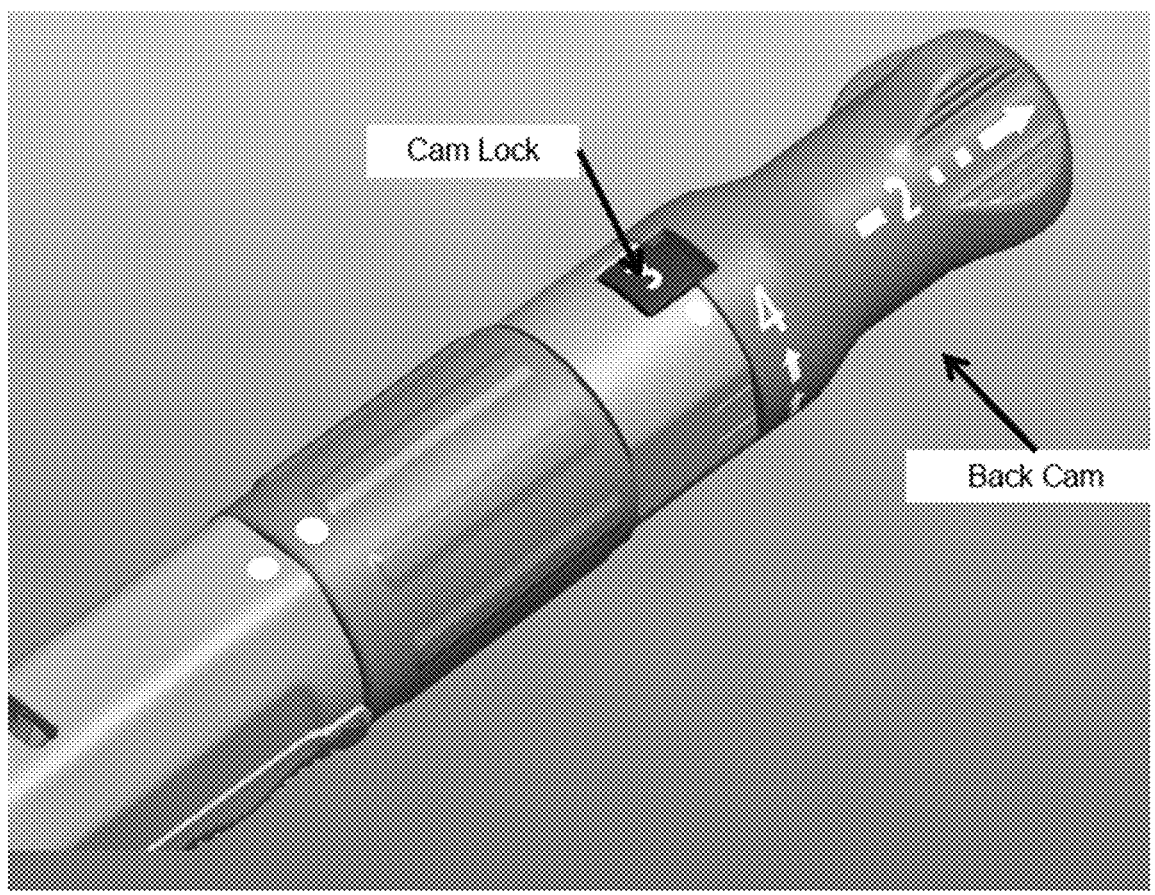
FIG. 42 depicts an image of a device assembly, wherein the cam lock is depressed.

In certain embodiments, the handle end houses the release sleeve hub, the retainer sleeve hub, and the push tube hub (see FIG. 41). In certain embodiments, the retainer sleeve hub remains stationary while (a) the push tube hub moves forward, which deploys a retention member (e.g., a pin), and (b) the release sleeve hub moves back to release the implant. In certain embodiments, these hub movements are actuated by depressing the cam lock (3) and rotating the back cam (4) clockwise 180° from a first position (see FIG. 42) to a second position (see FIG. 43). In certain embodiments, the hub movements, e.g., depressing the cam lock (3) and rotating the back cam (4), can be actuated only after the guidewire is fully retracted from the delivery device. In certain embodiments, the hub movements, e.g., depressing the cam lock (3) and rotating the back cam (4), can be actuated without the guidewire fully retracted from the delivery device. In certain embodiments, the delivery shaft and/or handle comprise a plurality of graphical markings and/or engravings (e.g., alphanumeric markings) indicative of an actuating sequence for use of the delivery device (e.g., numbering to guide the user in the use of the delivery device).

Guidewire Lumen Closure

Figure 46:
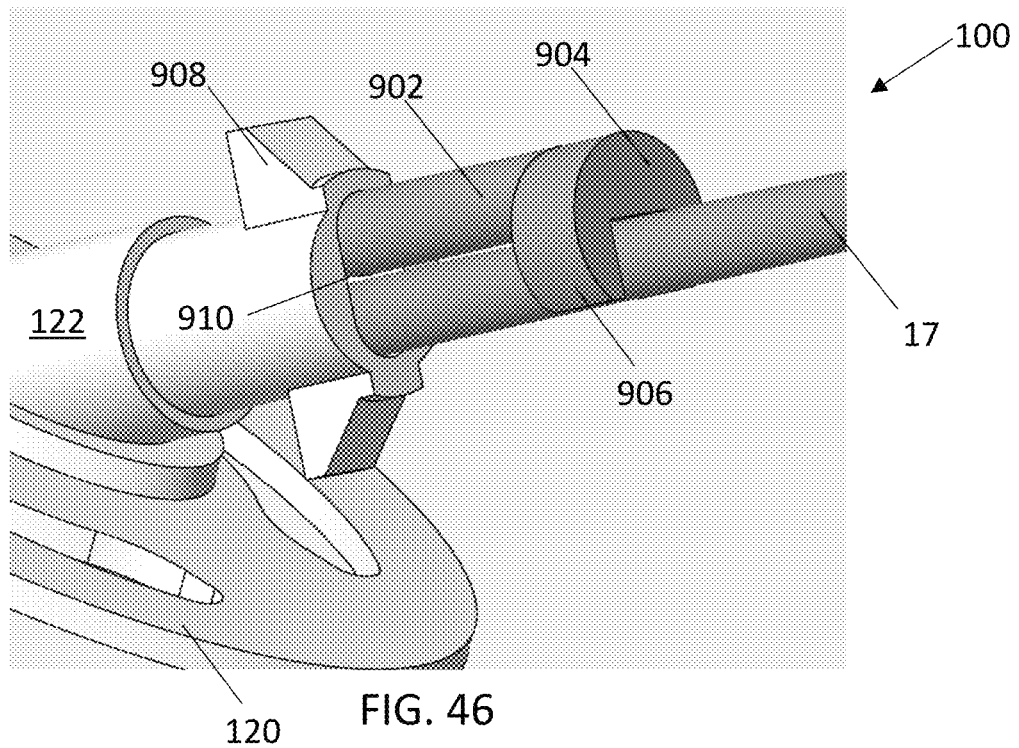
FIG. 46 illustrates an image of a closure device with a guidewire lumen closure pin, according to aspects of the present embodiments.
Figure 47:
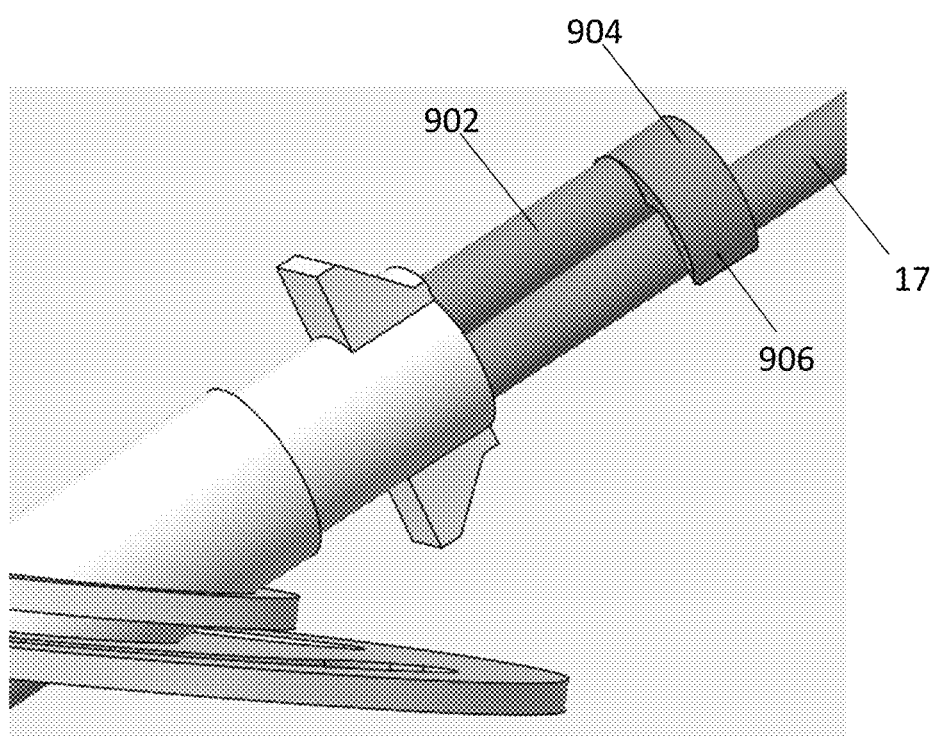
FIG. 47 illustrates an image of a closure device with a guidewire lumen closure pin, according to aspects of the present embodiments.
Figure 48:
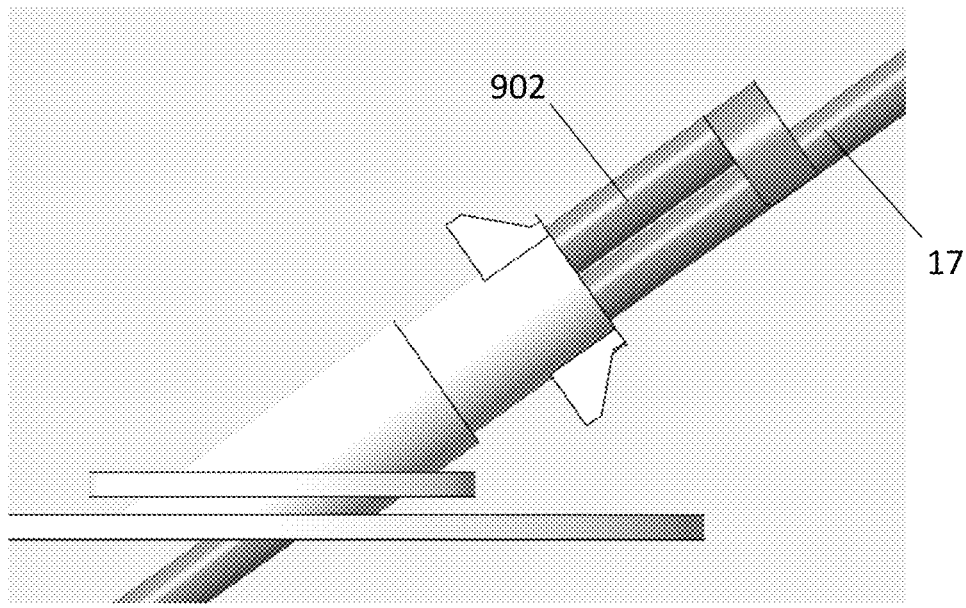
FIG. 48 illustrates an image of a closure device with a guidewire lumen closure pin, according to aspects of the present embodiments.
Figure 49:
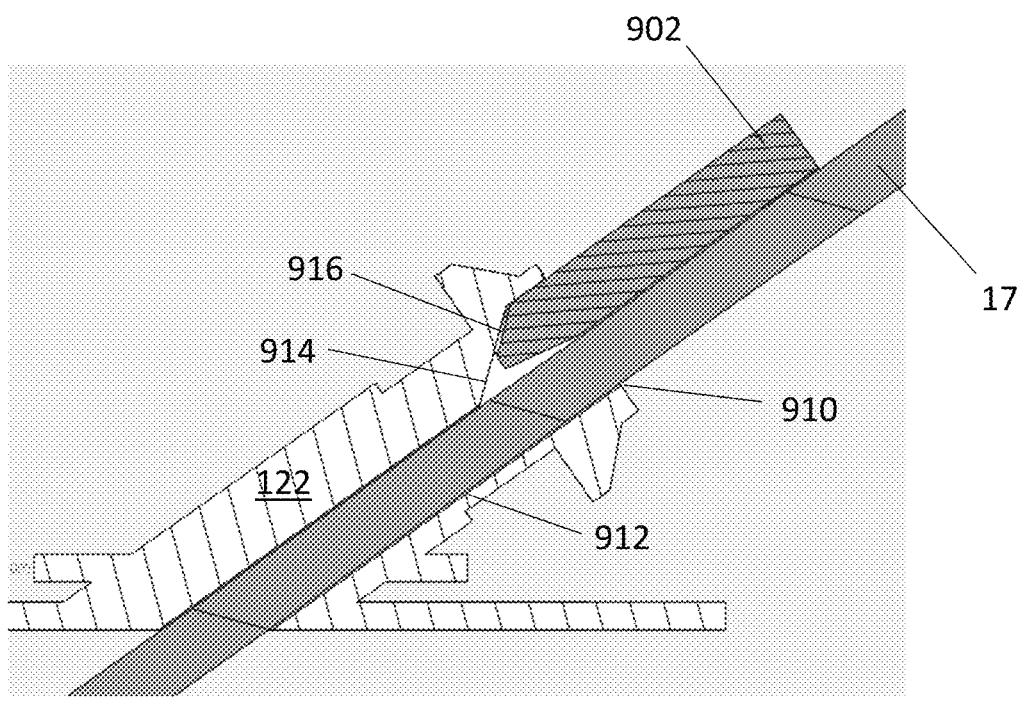
FIG. 49 illustrates an image of a closure device with a guidewire lumen closure pin, according to aspects of the present embodiments.
Figure 50:
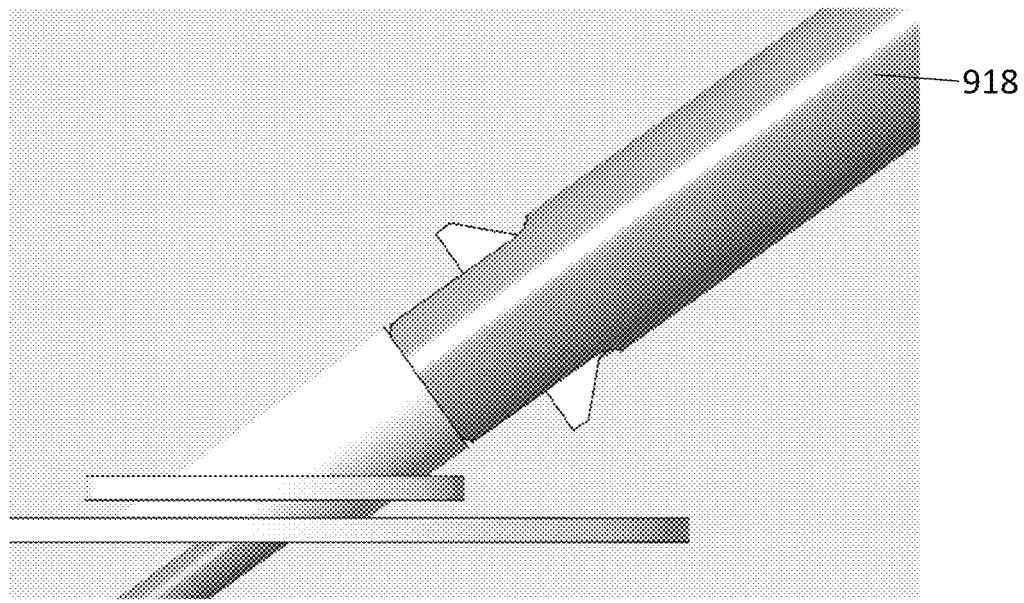
FIG. 50 illustrates an image of a closure device with a guidewire lumen closure pin, according to aspects of the present embodiments.
Figure 51:
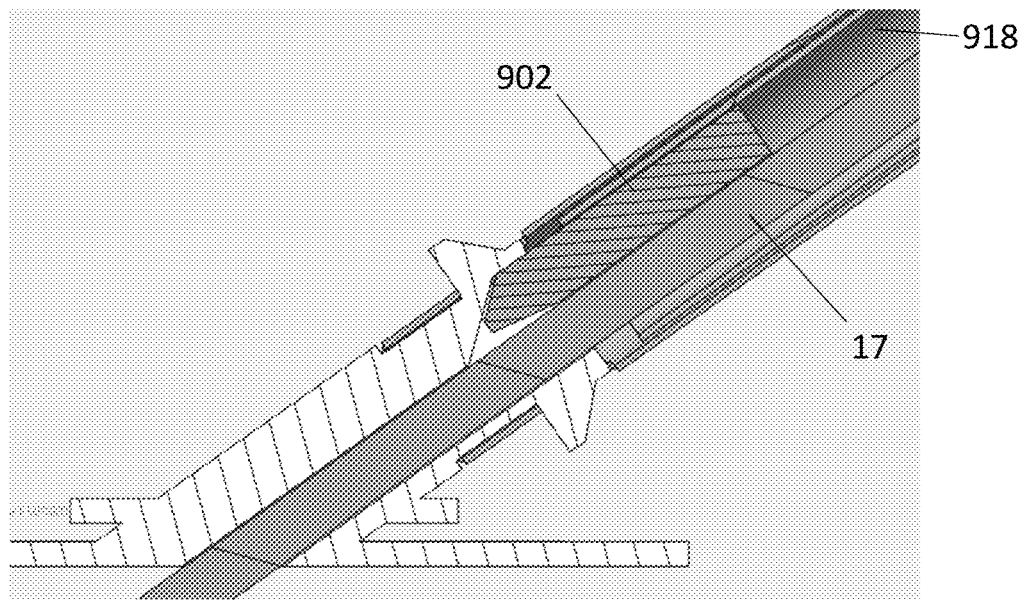
FIG. 51 illustrates an image of a closure device with a guidewire lumen closure pin, according to aspects of the present embodiments.

FIGS. 46-57 illustrate images of a first embodiment of a closure device 100 with a guidewire lumen closure pin 902, according to aspects of the present embodiments. As shown in FIG. 46, the device 100 includes a closure pin 902 disposed adjacent to, and in contact with, the guidewire 17. The closure pin 902 may include a generally circular or cylindrical pin head 904, as well as two curved arms 906 that are part of the pin head 904 and wrap around the guidewire 17. In use, the closure pin 902 and/or the guidewire 17 may be slidably disposed within a mouth 910 disposed within the column 122, which extends at an angle from the base 120. The column 122 may include two locking tabs 908 disposed on opposite sides of the column 122, approximately 180 degrees apart. FIGS. 47 and 48 illustrate other views of the device 100 including the closure pin 902 and guidewire 17. FIG. 49 illustrates a cross section of the guidewire 17 and closure pin 902 inserted into the mouth 910, with the guidewire 17 also disposed within a guidewire lumen 912, the guidewire lumen 912 being disposed all the way through the column 122. At a transition between the guidewire lumen 912 and the mouth 910, the column 122 may include an internal taper 914 that angles radially inward and interfaces with a corresponding angled tip 916 of the closure pin 902, such that the internal taper 914 pushes the closure pin 902 toward (and into) the guidewire lumen 912 when the closure pin 902 is pushed distally into the mouth 910 (i.e., after the guidewire 17 is removed from the guidewire lumen 912). In some embodiments, the angle of the internal taper 914 and the angled tip 916 may be complementary (for example 30 degrees and 60 degrees, 45 degrees and 45 degrees, or 60 degrees and 30 degrees, respectively, relative o a longitudinal axis of the column 122 and/or guidewire lumen 912).

Figure 52:
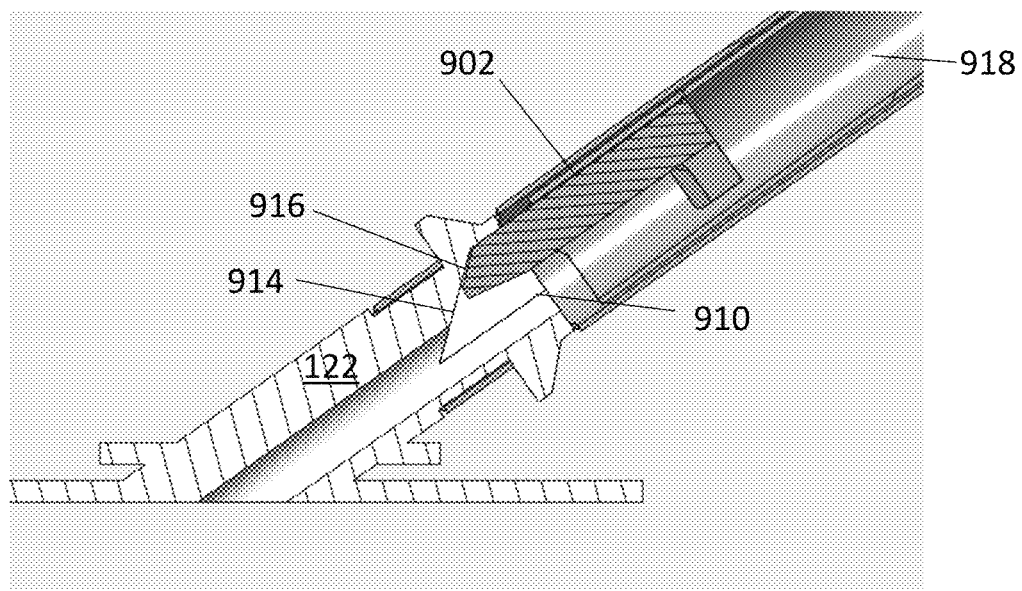
FIG. 52 illustrates an image of a closure device with a guidewire lumen closure pin, according to aspects of the present embodiments.
Figure 53:
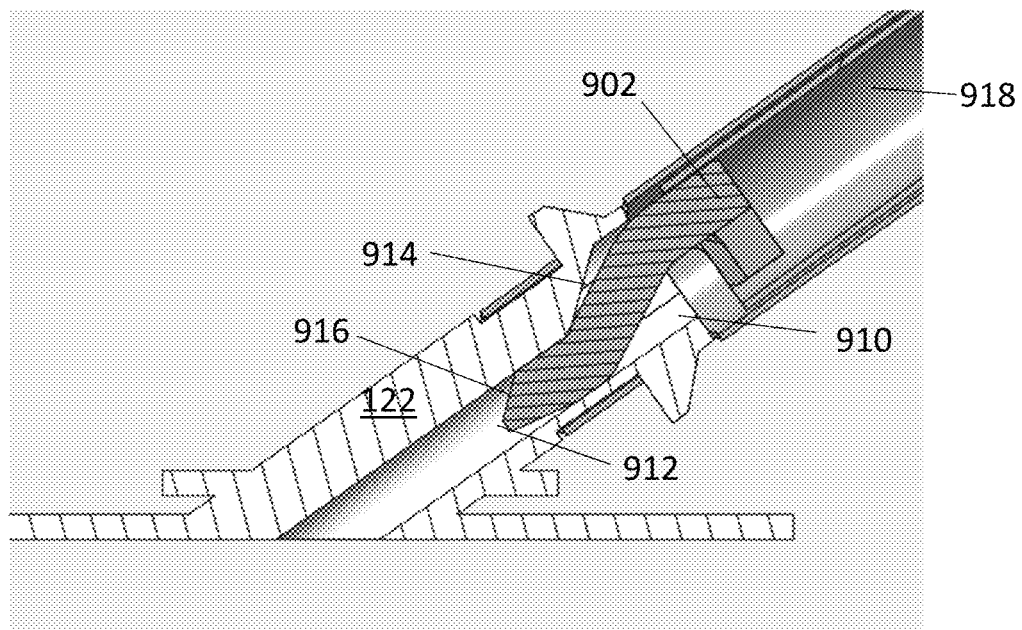
FIG. 53 illustrates an image of a closure device with a guidewire lumen closure pin, according to aspects of the present embodiments.

FIGS. 50-54 illustrate images of the first embodiment of a closure device 100 with a guidewire lumen closure pin 902 including external and/or cross-sectional views of the delivery shaft 918, according to aspects of the present embodiments. FIG. 52 illustrates the closure pin 902 with the angled tip 918 disposed within the mouth 910 after the guidewire 17 has been removed from the column 122. As the closure pin 902 is pushed farther into the column 122, the internal taper 914 pushes the angled tip 916 of the closure pin 902 into the guidewire lumen 912, as shown in FIG. 53, thereby closing the guidewire lumen 912 and sealing the closure site. The closure pin 902 and guidewire 17 may be approximately the same diameter (for example 0.035 inches (35 mils) (or from about 0.025 inches to about 0.04 inches, or from about 0.015 inches to about 0.05 inches) such that each may move within the guidewire lumen 912 with a slight clearance that does not allow blood to flow past (i.e., in the very small annulus between the outer surface of the closure pin 902 and/or guidewire 17 and the inner surface of the guidewire lumen 912).

Figure 54:
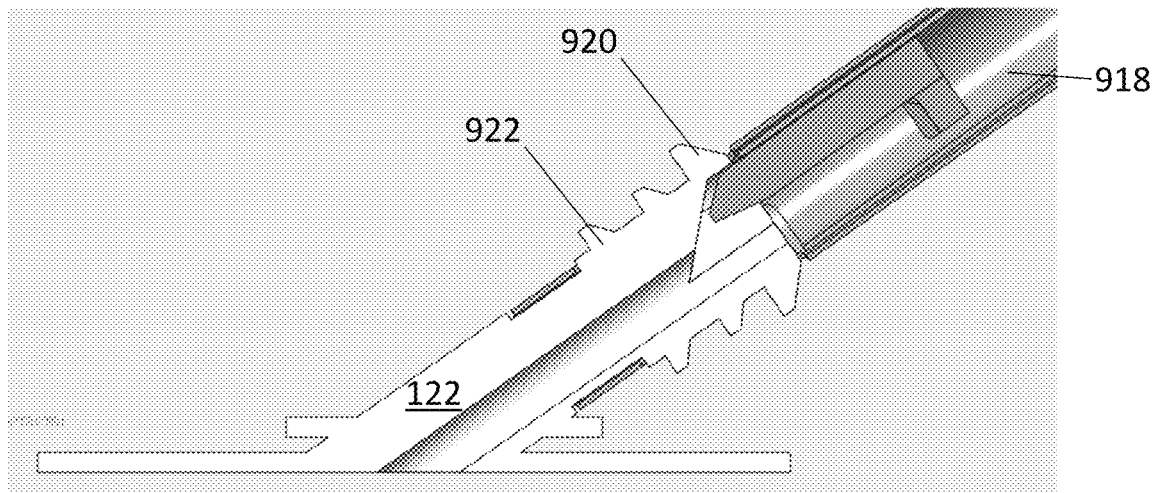
FIG. 54 illustrates an image of a closure device with a guidewire lumen closure pin, according to aspects of the present embodiments.
Figure 55:
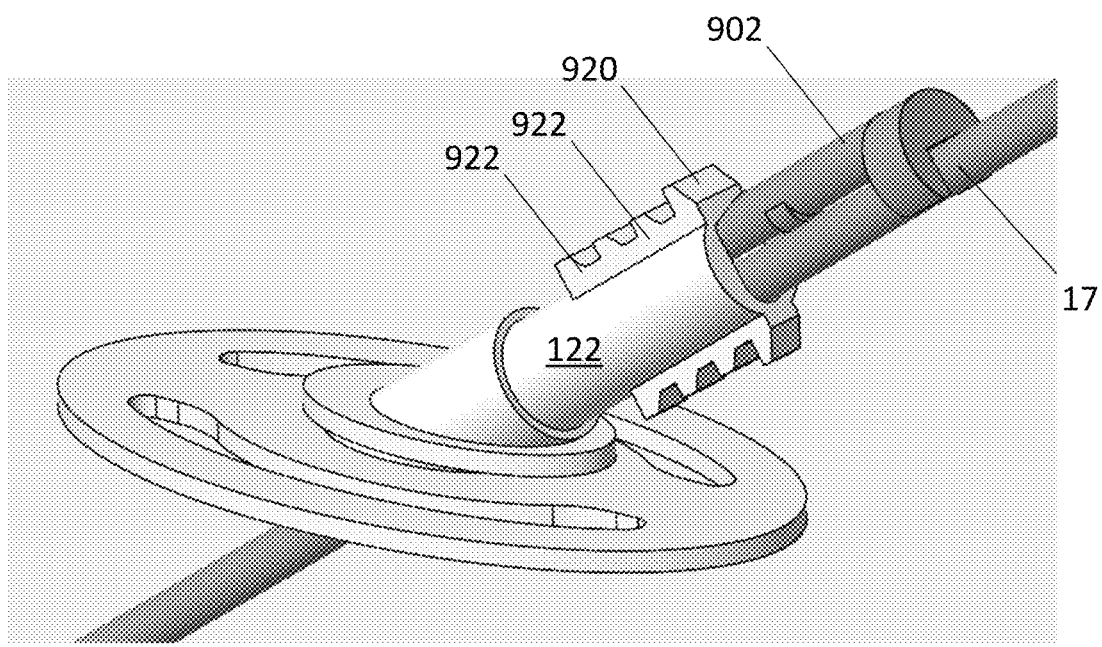
FIG. 55 illustrates an image of a closure device with a guidewire lumen closure pin, according to aspects of the present embodiments.
Figure 56:
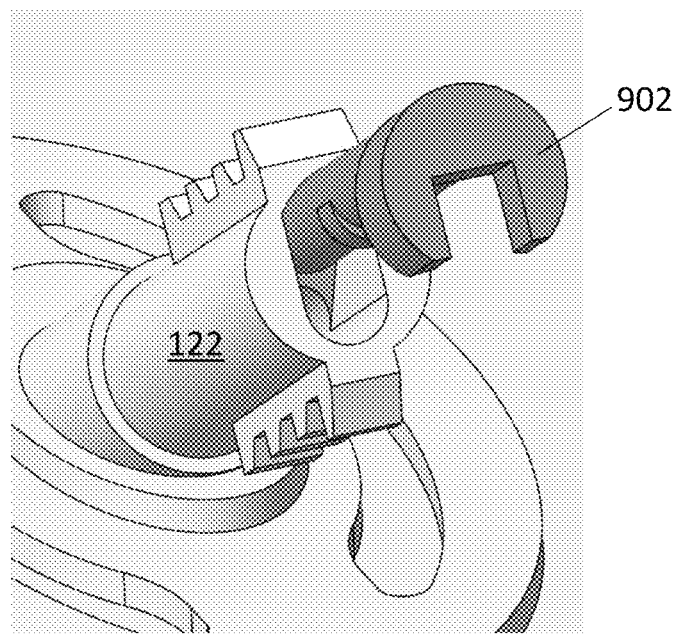
FIG. 56 illustrates an image of a closure device with a guidewire lumen closure pin, according to aspects of the present embodiments.
Figure 57:
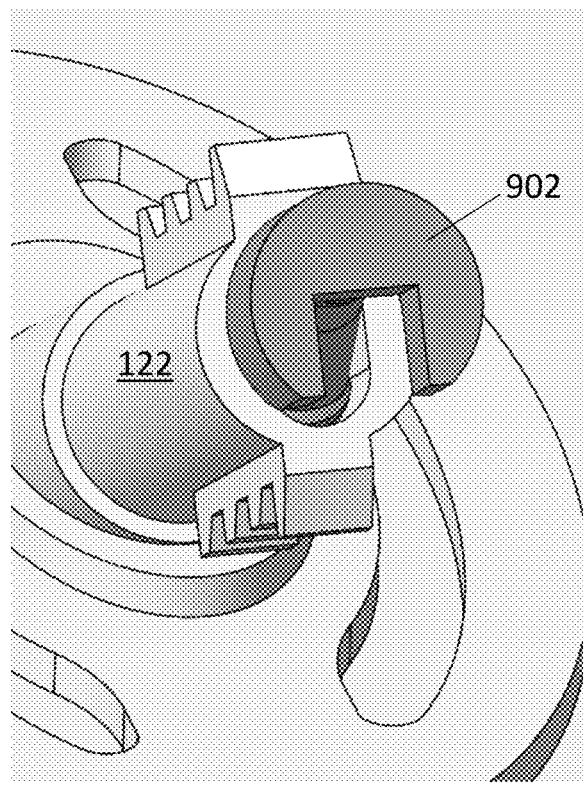
FIG. 57 illustrates an image of a closure device with a guidewire lumen closure pin, according to aspects of the present embodiments.
Figure 58:
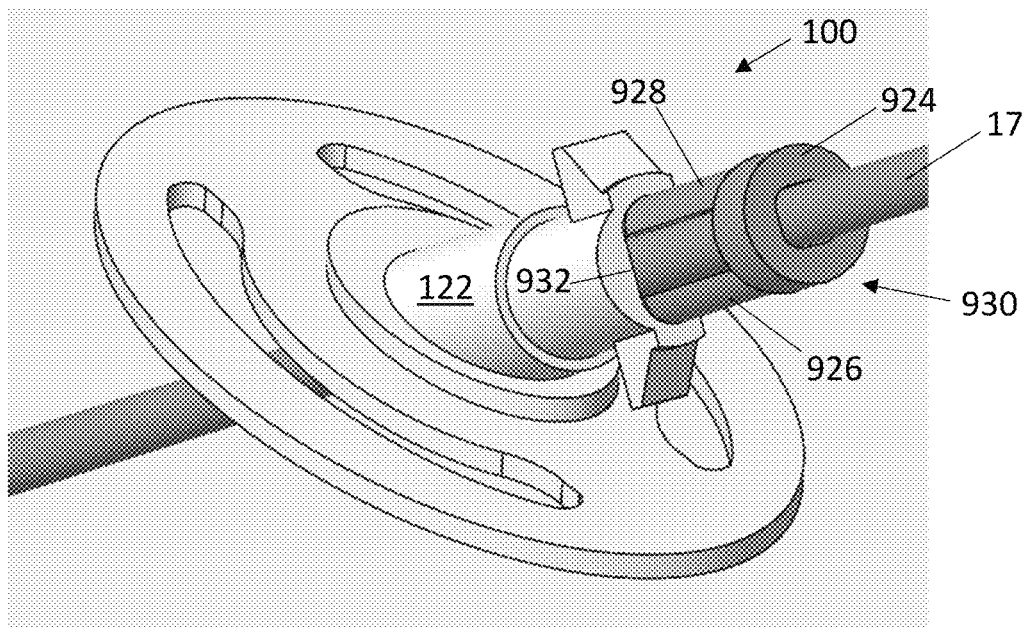
FIG. 58 illustrates an image of a closure device with a guidewire lumen closure pin, according to aspects of the present embodiments.

FIGS. 54 and 55 illustrate images of the closure device 100 with the first embodiment of the guidewire lumen closure pin 902, according to aspects of the present embodiments. In the embodiments illustrated in FIGS. 54 and 55, the device 100 includes 3 sets and 4 sets of locking tabs 920, 922, respectively. In FIG. 54, the device includes a first set of locking tabs 920 located at a proximal-most end of the column, as well as two additional sets (i.e., pairs) of locking tabs 922 located distally from the first pair of locking tabs 920. In some embodiments, the first pair of locking tabs 920 may be larger than each of the second, third, and fourth pairs (in the embodiment of FIG. 55) of locking tabs 922. Each pair or set of locking tabs 920, 922 may include two locking tabs protruding from opposite sides of the column 122, spaced approximately 180 degrees apart. The additional locking tabs allow for more closure positions to help accommodate various tissue thicknesses (for example, as illustrated in connection with the different closure positions shown in FIGS. 89-92). FIGS. 56 and 57 illustrate the closure pin 902 in open and closed positions respectively, within the column 122.

Figure 59:
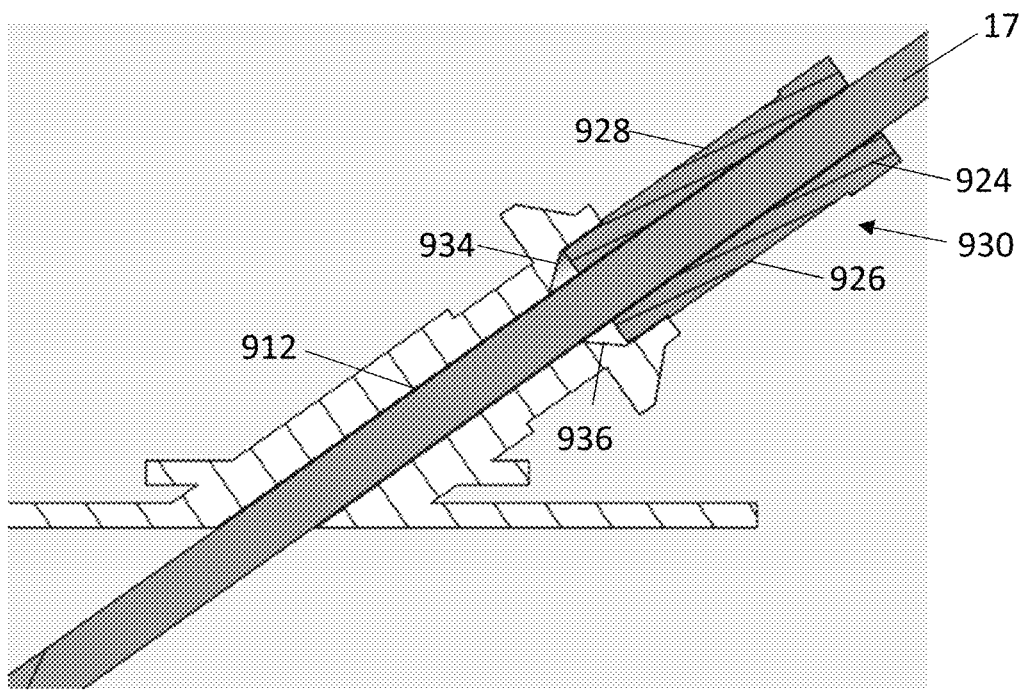
FIG. 59 illustrates an image of a closure device with a guidewire lumen closure pin, according to aspects of the present embodiments.
Figure 60:
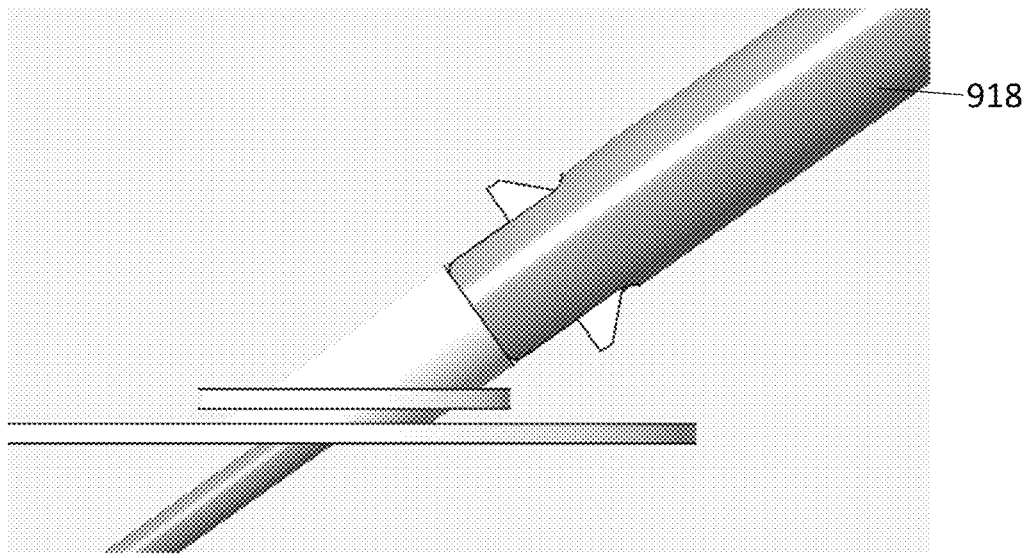
FIG. 60 illustrates an image of a closure device with a guidewire lumen closure pin, according to aspects of the present embodiments.
Figure 61:
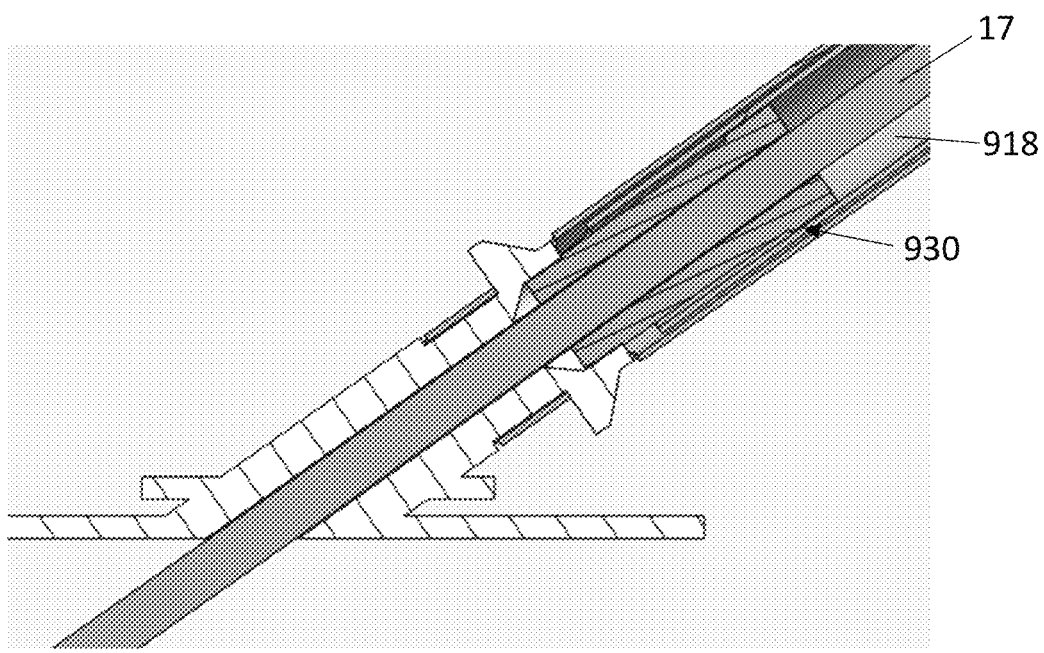
FIG. 61 illustrates an image of a closure device with a guidewire lumen closure pin, according to aspects of the present embodiments.
Figure 62:
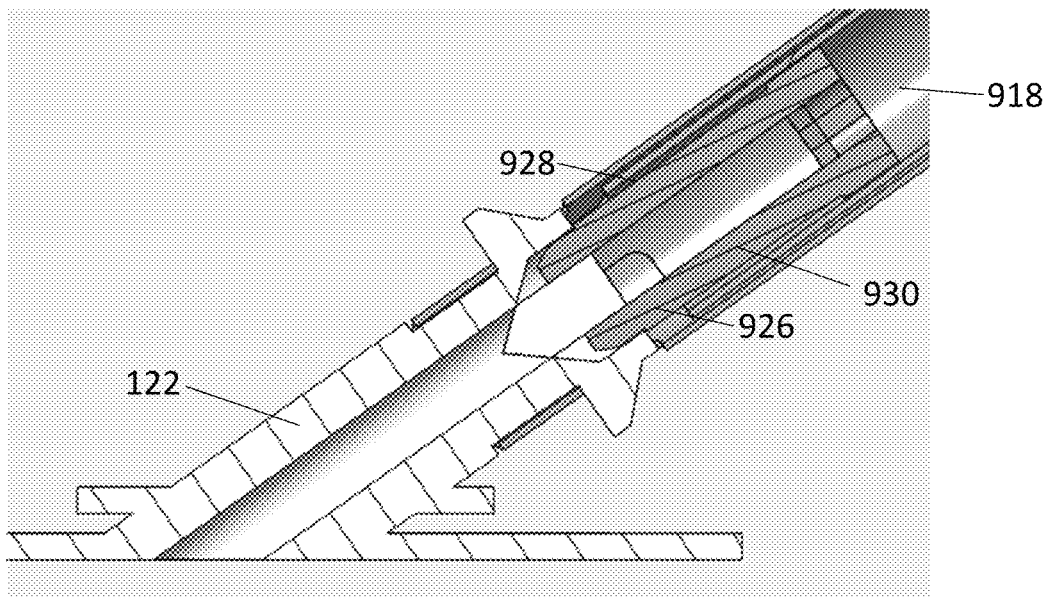
FIG. 62 illustrates an image of a closure device with a guidewire lumen closure pin, according to aspects of the present embodiments.
Figure 63:
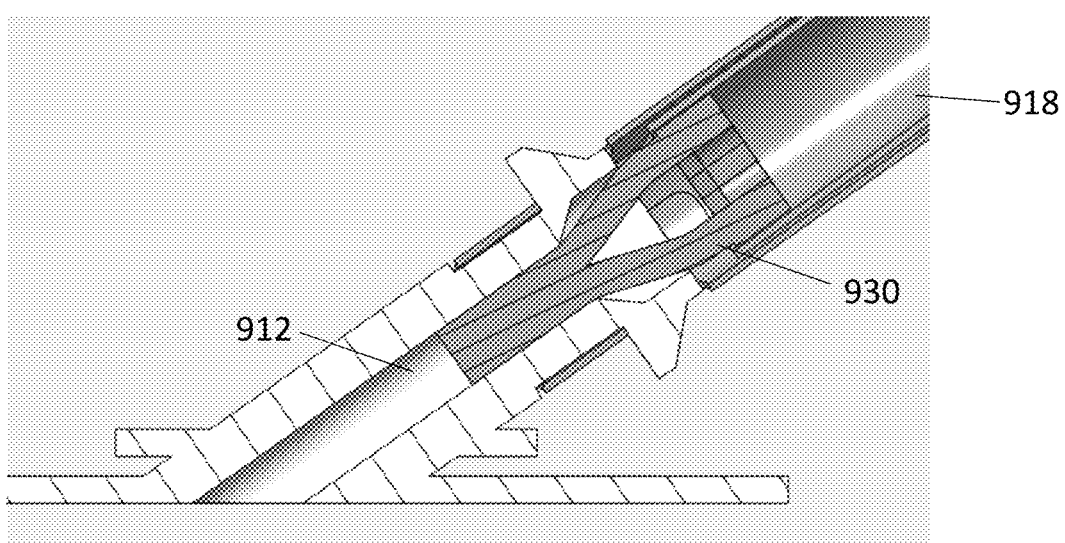
FIG. 63 illustrates an image of a closure device with a guidewire lumen closure pin, according to aspects of the present embodiments.

FIGS. 58-63 illustrate images of the closure device 100 with a second embodiment of the guidewire lumen closure pin 930, according to aspects of the present embodiments. The second embodiment of the closure pin 930 may include a circular or cylindrical pin head 924 configured to be concentrically disposed about the guidewire 17 when the guidewire is within the column 122. The closure pin 930 may include first and second arms 926 and 928 configured to be disposed on opposite sides of the guidewire 17, and slidable within an elongated mouth 932 disposed within the column 122. The column 122 may include first and second internal tapers 934, 936, as shown in FIG. 59, to push the first and second arms 926, 928 into the guidewire lumen 912 as the closure pin 930 is pushed into the column 122 after the guidewire 17 is removed. FIGS. 60-63 illustrate the delivery shaft 918 (in addition to the closure device 100) with the second embodiment of the closure pin 930. FIGS. 62 and 63 illustrate the closure pin 930 after the guidewire 17 has been removed. FIG. 62 illustrates the position and shape of the closure pin 930 prior to being pushed further into the column 122, while FIG. 63 shows the closure pin 930 after being pushed into the guidewire lumen 912, thereby sealing the guidewire lumen 912. Because the first and second arms 926, 928 together fill the guidewire lumen 912 when in the sealed position of FIG. 63, each of the first and second arms 926, 928 may include a cross-sectional area that is roughly half of the cross-sectional area of the guidewire lumen 912.

Figure 64:
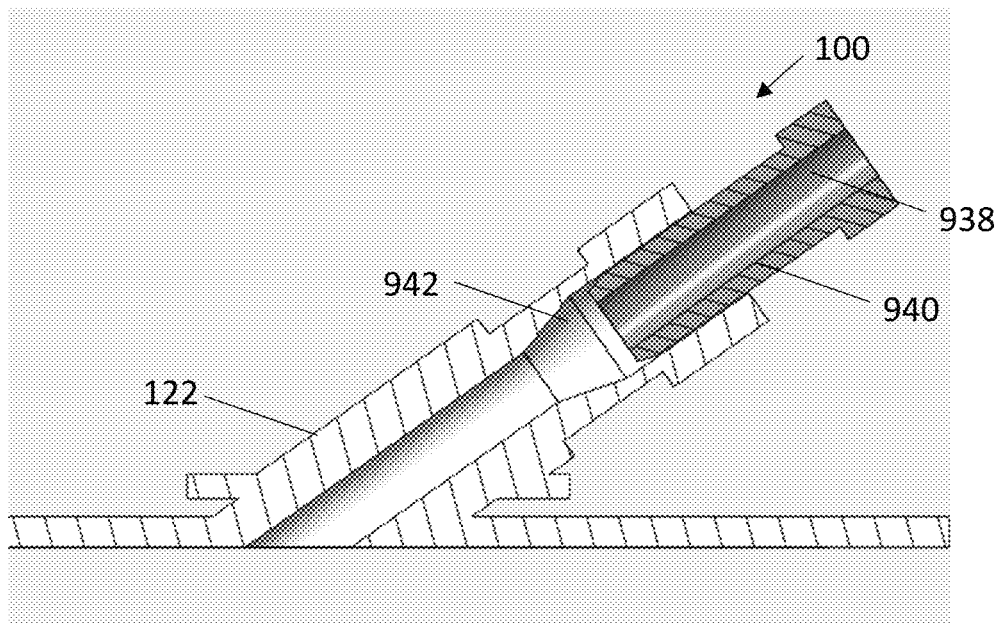
FIG. 64 illustrates an image of a closure device with a guidewire lumen closure pin, according to aspects of the present embodiments.
Figure 65:
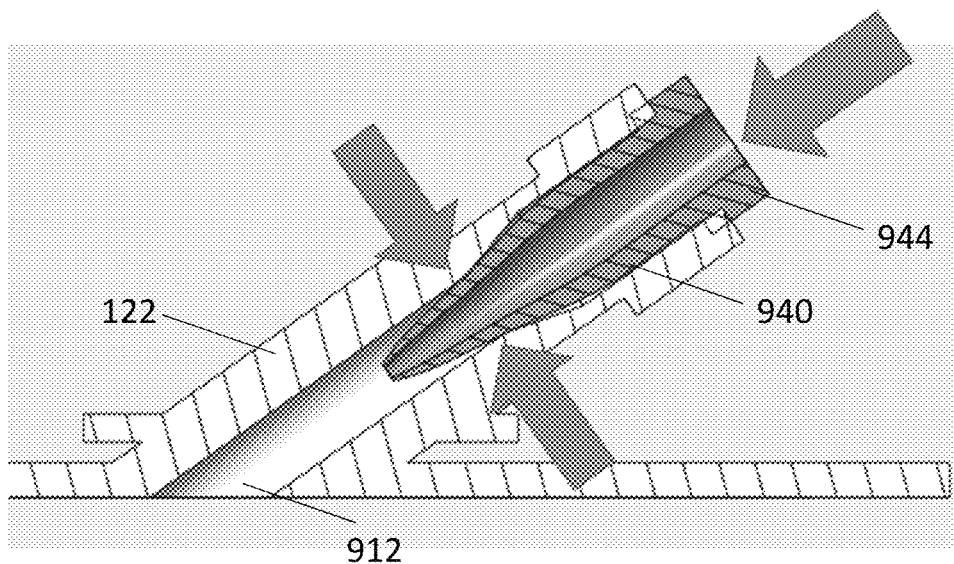
FIG. 65 illustrates an image of a closure device with a guidewire lumen closure pin, according to aspects of the present embodiments.

FIGS. 64 and 65 illustrate images of the closure device 100 with a third embodiment of the guidewire lumen closure pin 940, according to aspects of the present embodiments. The third embodiment of the closure pin 940 may include a circular or cylindrical pin head 944 configured to be concentrically disposed about the guidewire 17 when the guidewire is within the column 122 (and closure pin 940). The closure pin 940 may also include a through bore 938 running through the entire length of the closure pin 940, within which the guidewire 17 is disposed when it is within the column 122. The device 100 shown in FIGS. 64 and 65 (specifically the column 122) includes a gradual tapered portion 942 with a cone-shaped interior for making the transition from a larger diameter of the closure pin 940 in the open position of FIG. 64 to the smaller diameter of the guidewire lumen 912. As a distal force is applied to the pin head 944, the inner walls of the column 122 at the gradual tapered portion 942 exert radially inward pressure on the closure pin 940 causing the closure pin 940 to be pinched or crimped inwardly, thereby filling the entire space of the smaller diameter guidewire lumen 912 and sealing the guidewire lumen 912 in the process.

Figure 66:
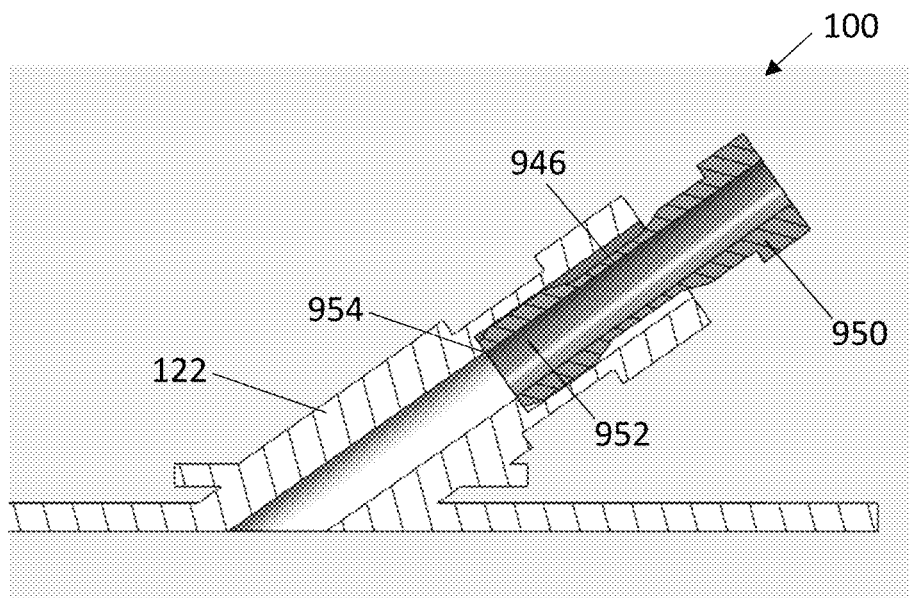
FIG. 66 illustrates an image of a closure device with a guidewire lumen closure pin, according to aspects of the present embodiments.
Figure 67:
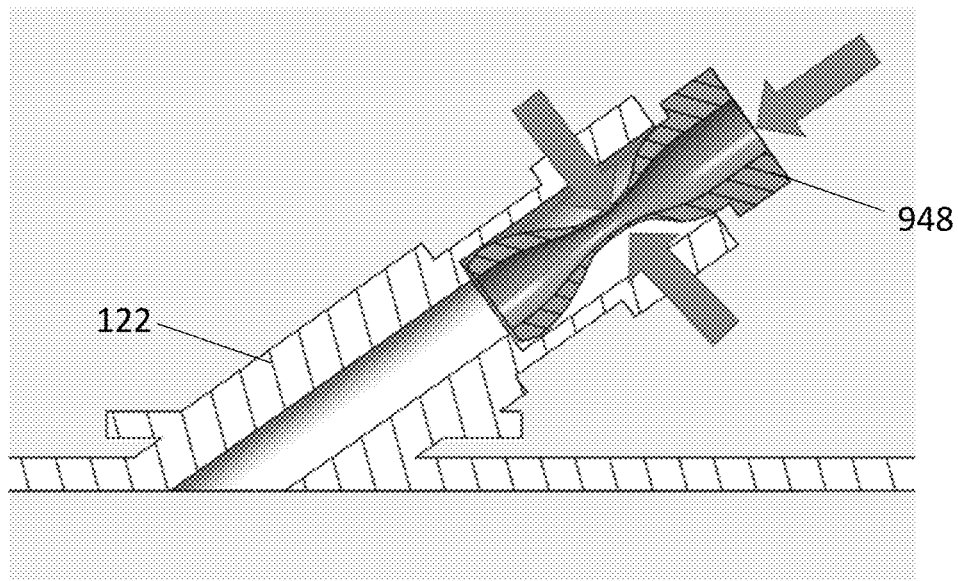
FIG. 67 illustrates an image of a closure device with a guidewire lumen closure pin, according to aspects of the present embodiments.
Figure 68:
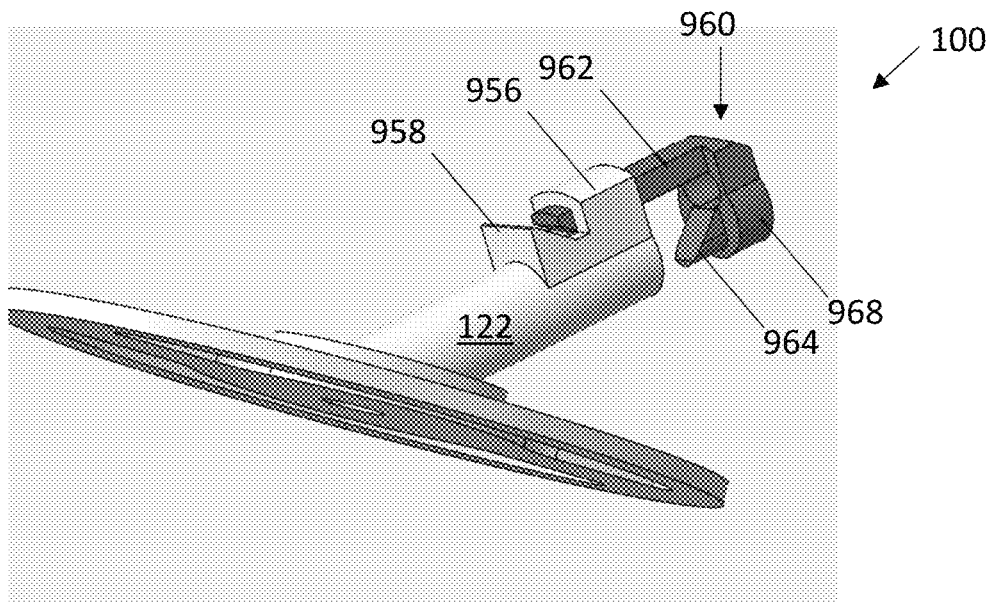
FIG. 68 illustrates an image of a closure device with a guidewire lumen closure pin, according to aspects of the present embodiments.
Figure 69:
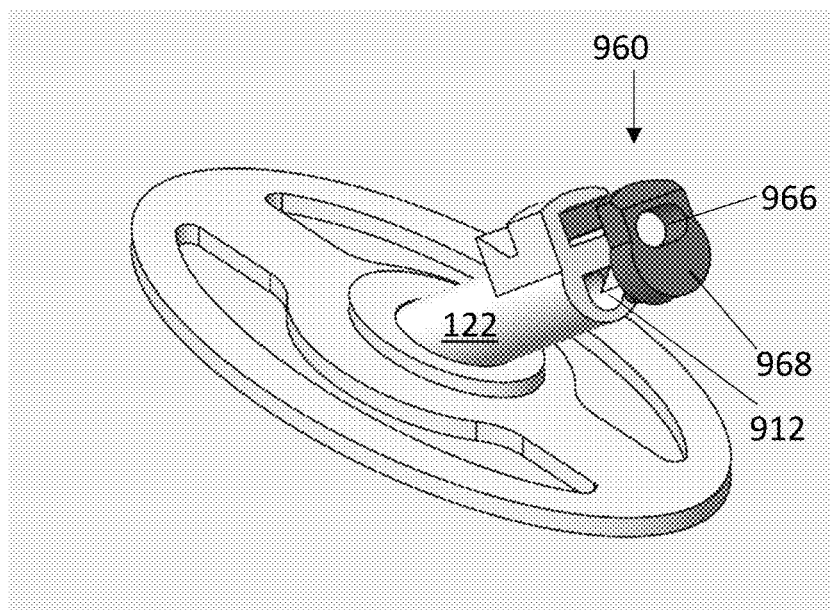
FIG. 69 illustrates an image of a closure device with a guidewire lumen closure pin, according to aspects of the present embodiments.
Figure 70:
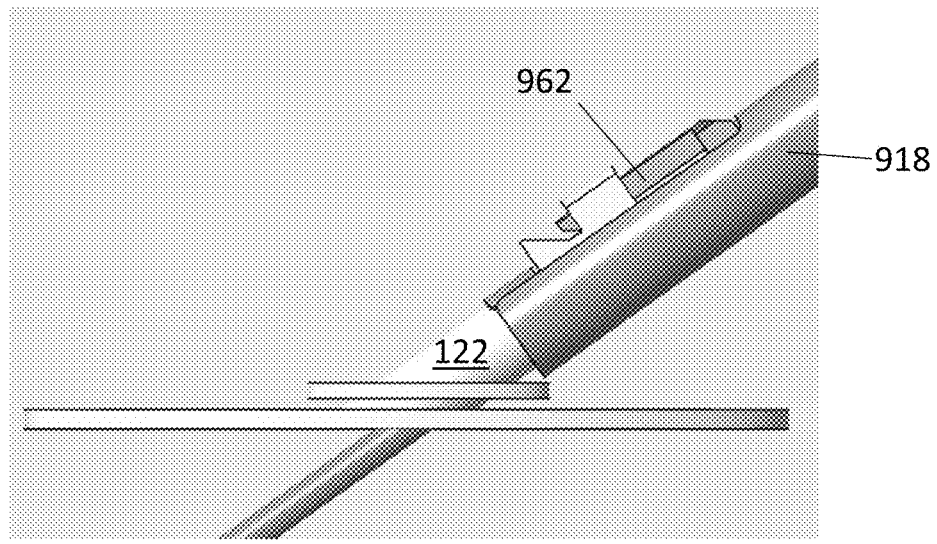
FIG. 70 illustrates an image of a closure device with a guidewire lumen closure pin, according to aspects of the present embodiments.

FIGS. 66 and 67 illustrate images of the closure device 100 with a fourth embodiment of the guidewire lumen closure pin 950, according to aspects of the present embodiments. The fourth embodiment of the closure pin 950 may include a circular or cylindrical pin head 948 configured to be concentrically disposed around the guidewire 17 when the guidewire is within the column 122 (and closure pin 950). The closure pin 950 may also include a through bore 952 running through the entire length of the closure pin 950, within which the guidewire 17 is disposed when it is within the column 122. The closure pin 950 shown in FIGS. 66 and 67 includes a rupture portion 952 with thin walls disposed within a longitudinal mid-section of the closure pin 950. The column 122 of FIGS. 66 and 67 may include an internal orthogonal stop 954. As a distal force is applied to the pin head 948, the distal end of the closure pin 950 contacts the internal orthogonal stop 954 causing the rupture portion 952 to rupture or crimp inwardly (due to the thinner walls of the rupture portion 946), thereby filling the entire space of the guidewire lumen 912 and sealing the guidewire lumen 912 in the process.

Figure 71:
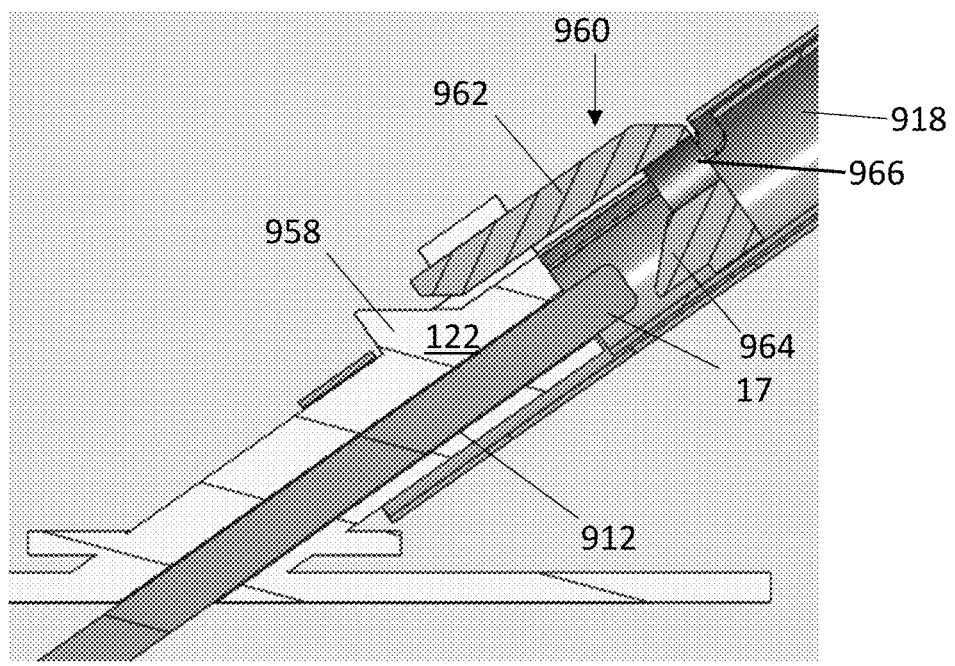
FIG. 71 illustrates an image of a closure device with a guidewire lumen closure pin, according to aspects of the present embodiments.
Figure 72:
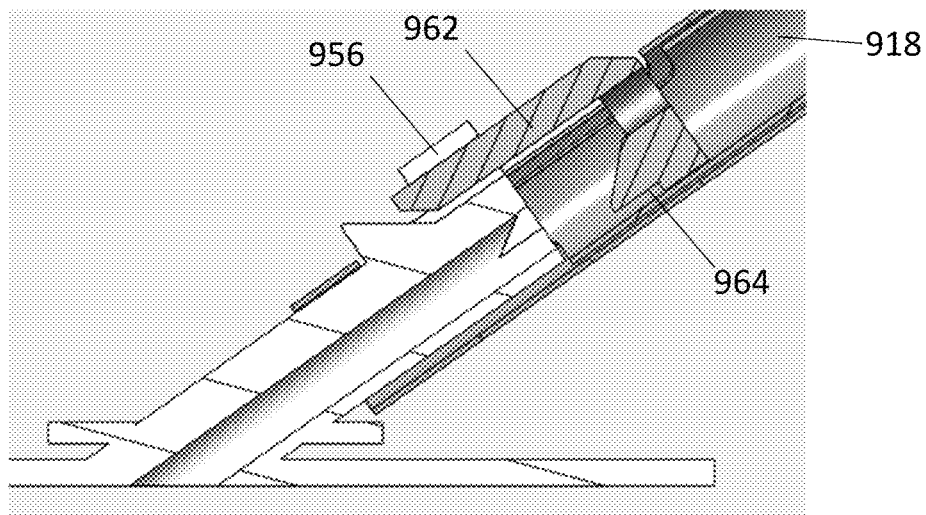
FIG. 72 illustrates an image of a closure device with a guidewire lumen closure pin, according to aspects of the present embodiments.
Figure 73:
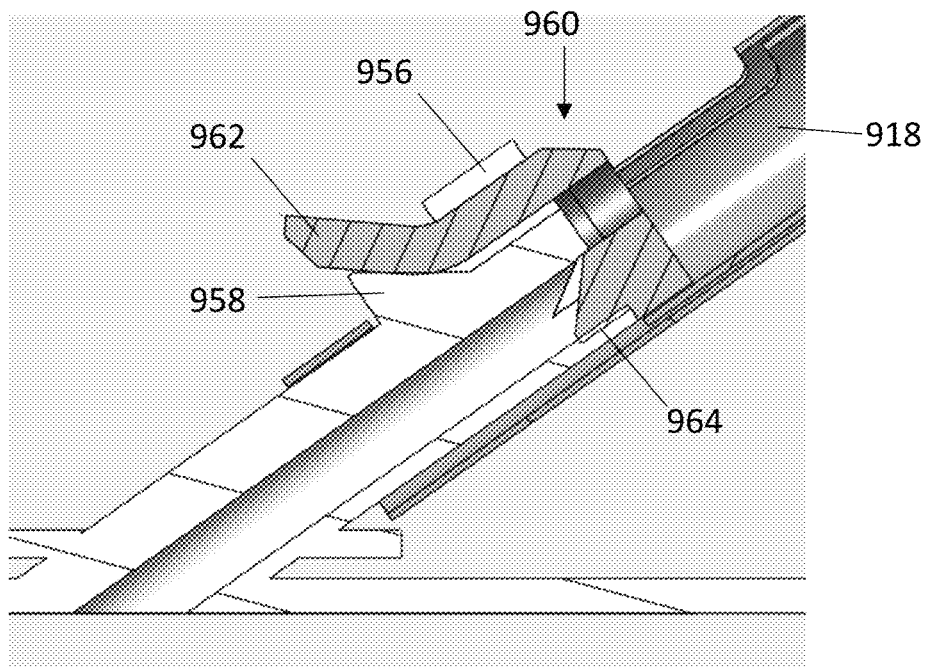
FIG. 73 illustrates an image of a closure device with a guidewire lumen closure pin, according to aspects of the present embodiments.
Figure 74:
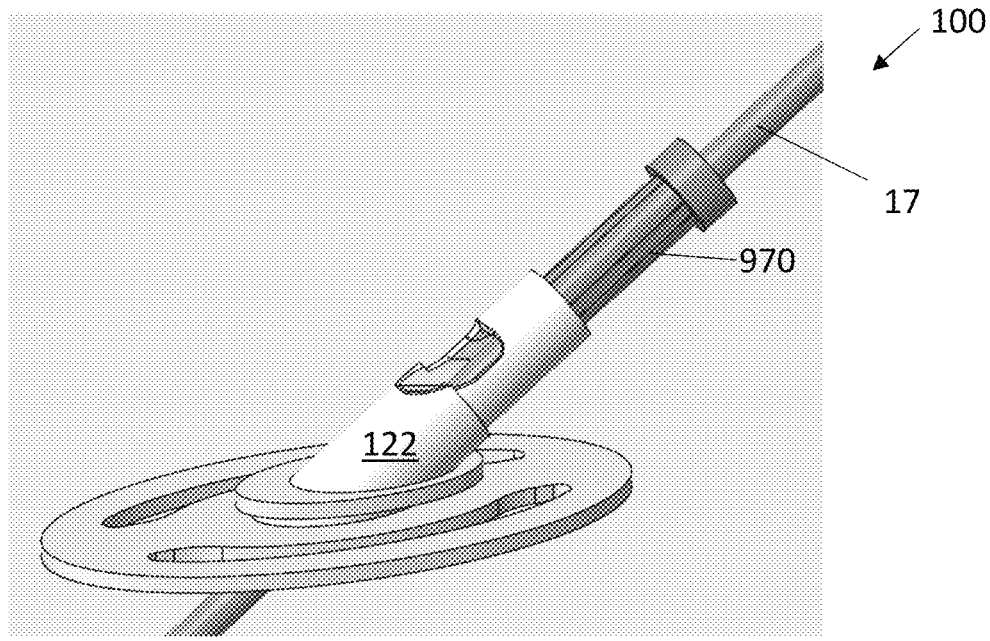
FIG. 74 illustrates an image of a closure device with a guidewire lumen closure pin, according to aspects of the present embodiments.
Figure 75:
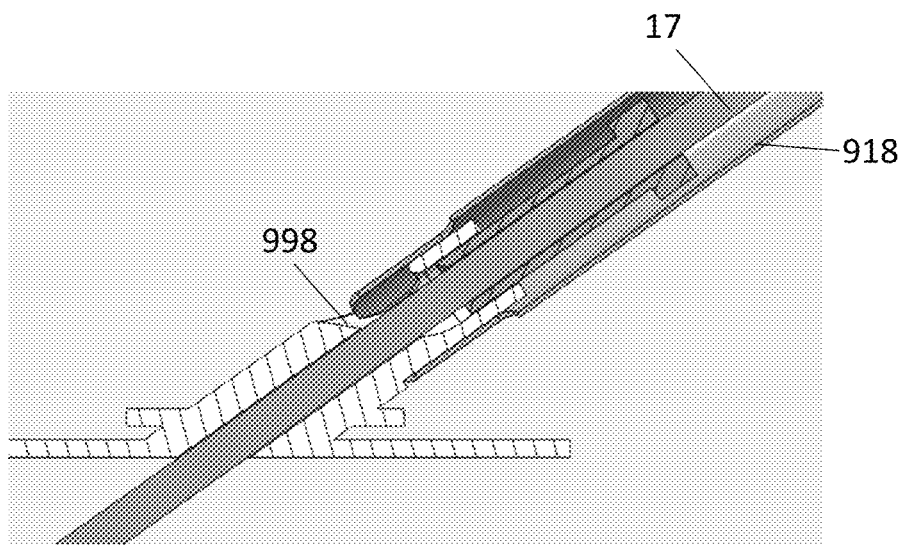
FIG. 75 illustrates an image of a closure device with a guidewire lumen closure pin, according to aspects of the present embodiments.
Figure 76:
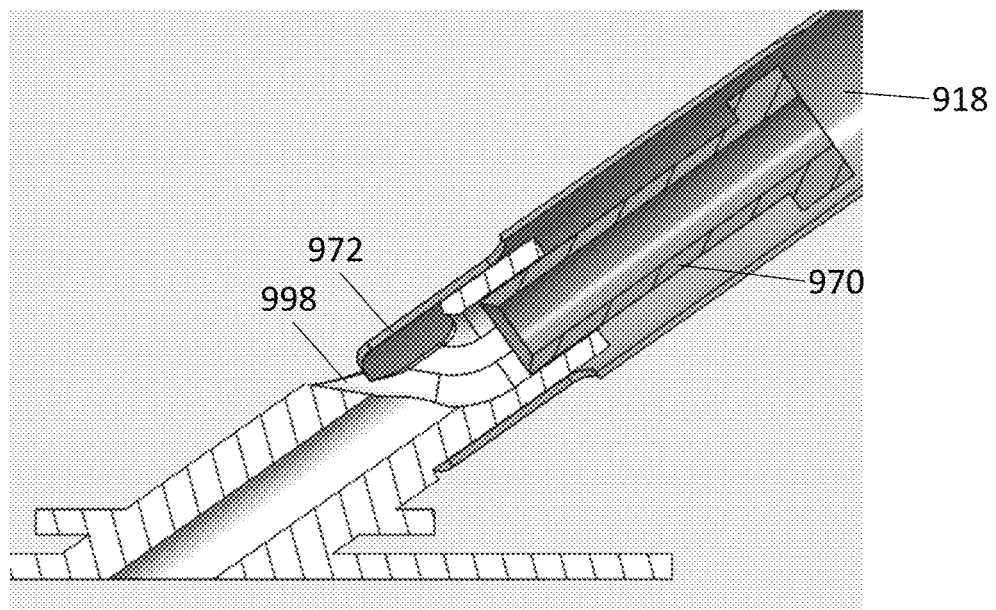
FIG. 76 illustrates an image of a closure device with a guidewire lumen closure pin, according to aspects of the present embodiments.
Figure 77:
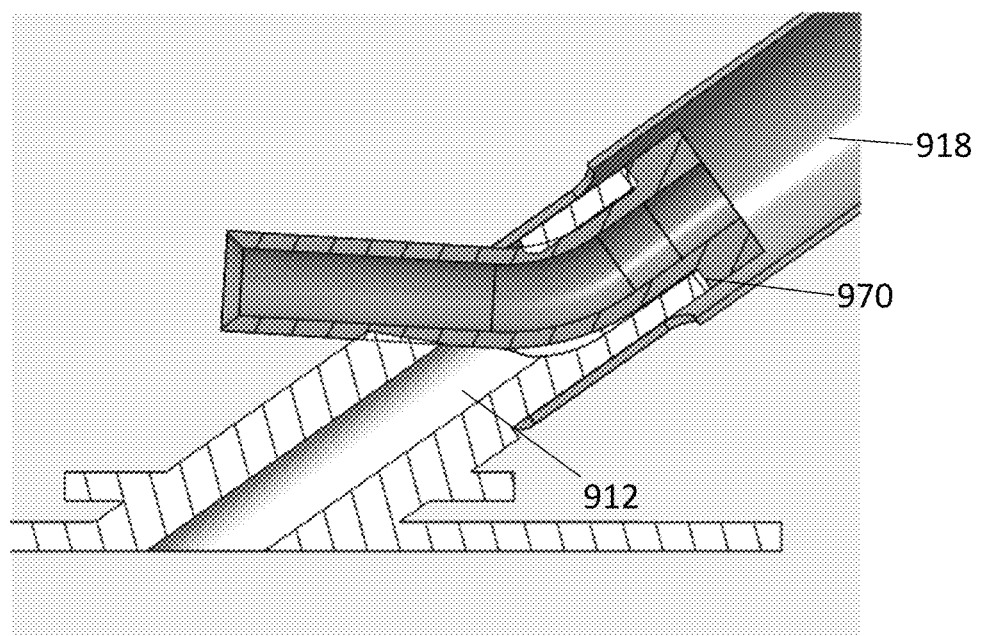
FIG. 77 illustrates an image of a closure device with a guidewire lumen closure pin, according to aspects of the present embodiments.
Figure 78:
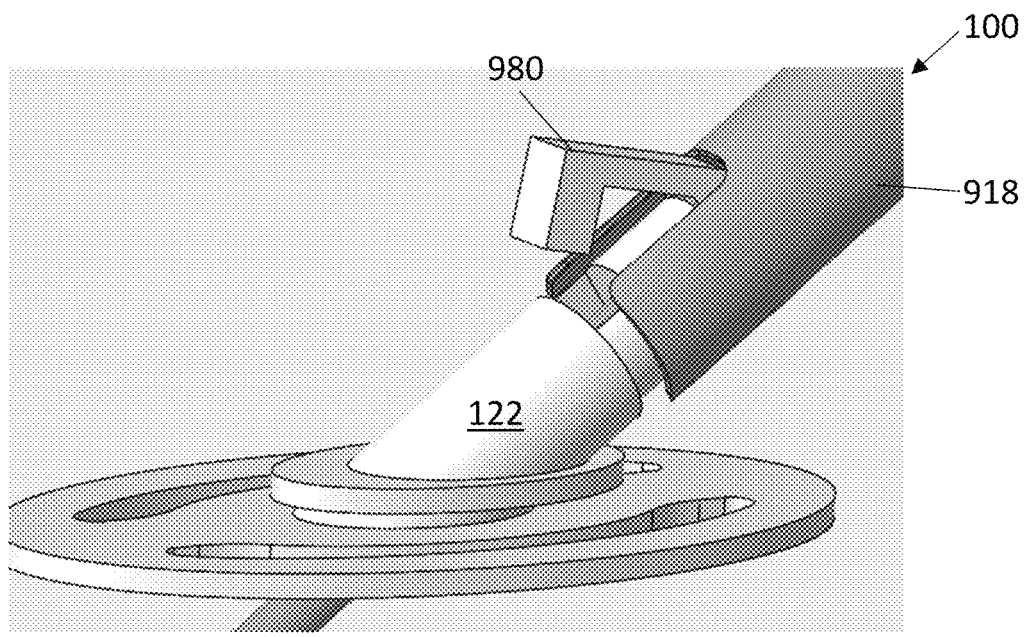
FIG. 78 illustrates an image of a closure device with a guidewire lumen closure pin, according to aspects of the present embodiments.
Figure 79:
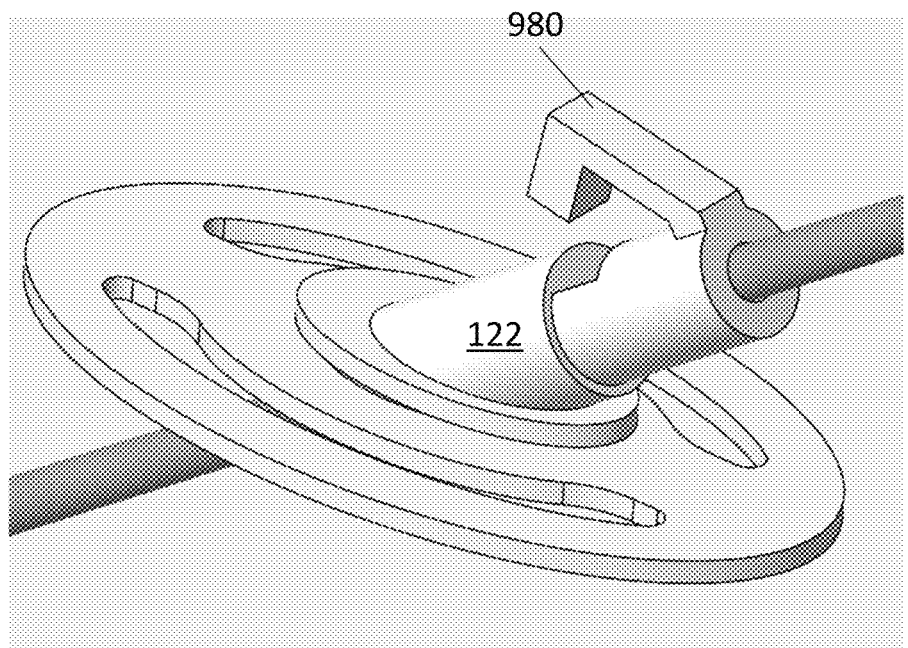
FIG. 79 illustrates an image of a closure device with a guidewire lumen closure pin, according to aspects of the present embodiments.
Figure 80:
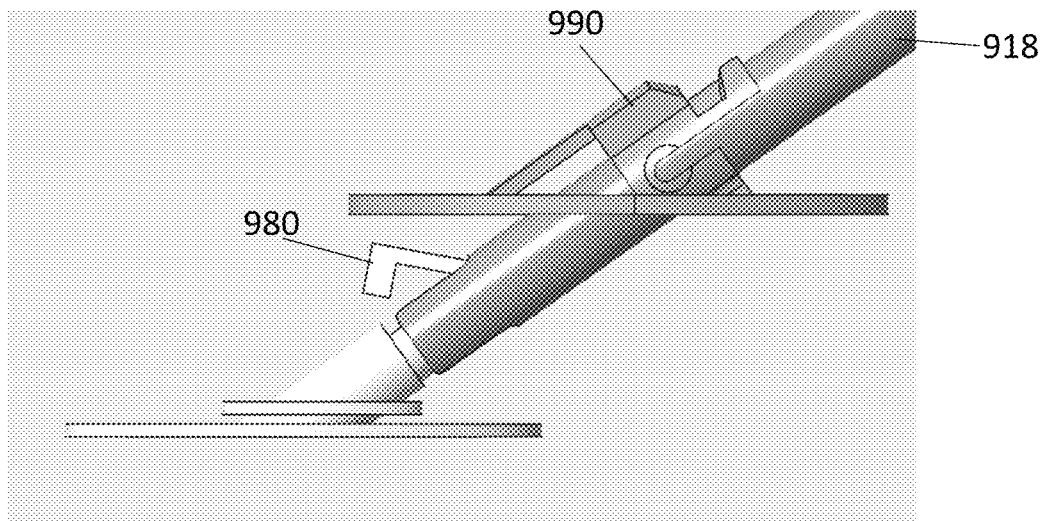
FIG. 80 illustrates an image of a closure device with a guidewire lumen closure pin, according to aspects of the present embodiments.
Figure 81:
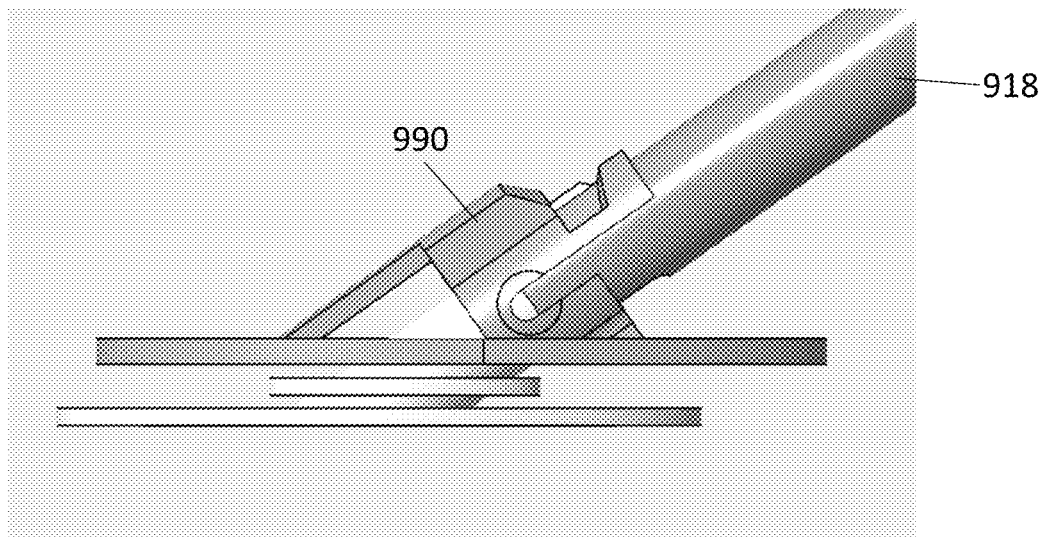
FIG. 81 illustrates an image of a closure device with a guidewire lumen closure pin, according to aspects of the present embodiments.
Figure 82:
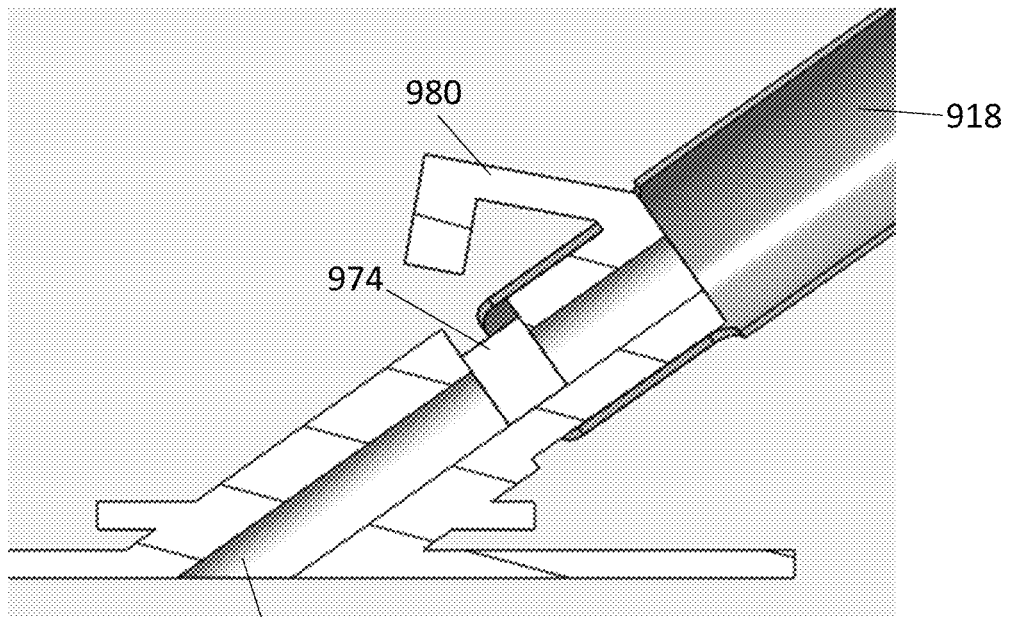
FIG. 82 illustrates an image of a closure device with a guidewire lumen closure pin, according to aspects of the present embodiments.

FIGS. 68-73 illustrate images of the closure device 100 with a fifth embodiment of the guidewire lumen closure pin 960, according to aspects of the present embodiments. The fifth embodiment of the closure pin 960 may include a slidable rod 962, an offset bore 966, an angled pin portion 964, and pin head 968. In some embodiments, both the angled pin portion 964 and the slidable rod 962 protrude distally form the pin head 968 while the offset bore 966 includes a hole disposed through the pin head 968 that is offset from the guidewire lumen 912. Stated otherwise, a centerline of the offset bore 966 is not collinear with a centerline of the guidewire lumen 912. The slidable rod 962 is configured to slide within a sleeve 956 disposed in column 122. At a distal end of the sleeve 956, the column 122 may include a ramp portion 958 for deflecting the slidable rod at an angle as it protrudes through the sleeve 956, as show in FIGS. 71-73. FIGS. 70-73 illustrate the delivery shaft 918. As illustrated in FIG. 71, the guidewire 17 and guidewire lumen 912 are linearly offset form the offset bore 966, through which the guidewire is installed when it is in the column 122. Accordingly, the guidewire 17 must bend in order to go through both the offset bore 966 and the guidewire lumen 912, which are not collinear with each other. Once the guidewire 17 is removed and the closure pin 960 is pushed distally toward the column 122, the angled pin portion 964 (which is collinear with the guidewire lumen 912) is pushed into the guidewire lumen 912, thereby closing the guidewire lumen 912, as shown in FIG. 73. The slidable rod 962 bends at it deflects off the ramp portion 958. The inherent stiffness and partial elasticity of the slidable rod 963, in connection with the sheath 956, helps to hold the closure pin 960 into place once it is in the closed position.

FIGS. 74-77 illustrate images of the closure device 100 with a sixth embodiment of the guidewire lumen closure pin 970, according to aspects of the present embodiments. The sixth embodiment of the closure pin 970 is concentrically disposed 360 degrees around the guidewire 17 and deflects off an angled surface 998 and through an aperture 972 in the column 122 and/or delivery shaft 918 such that a distal end of the closure pin 970 protrudes across the guidewire lumen 912 and out of the aperture 972, thereby sealing the guidewire lumen 912, as show in FIG. 77.

Figure 83:
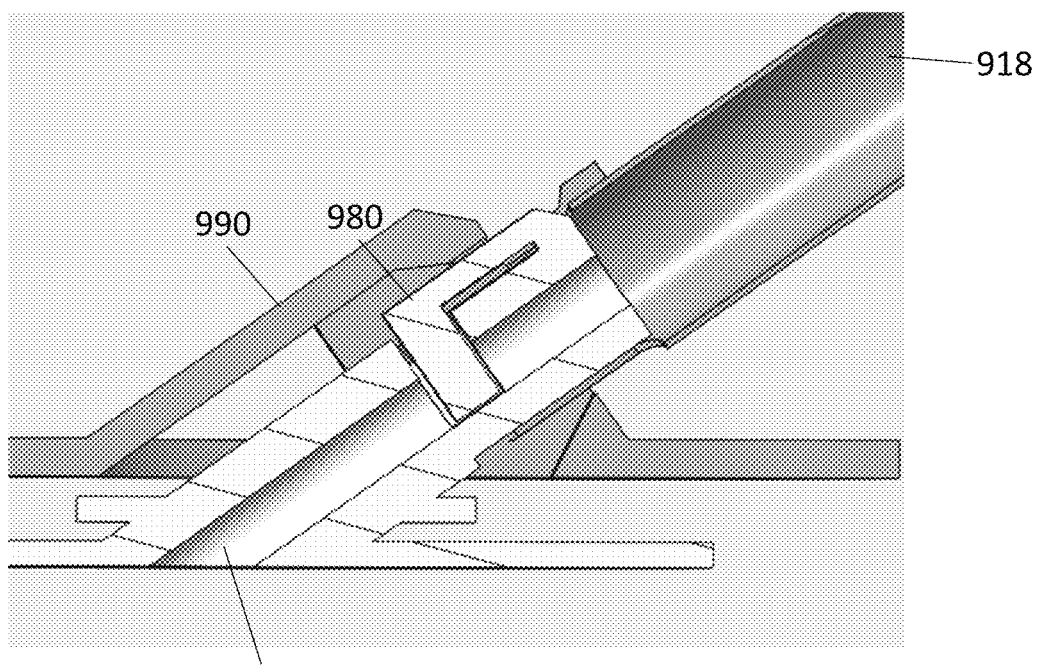
FIG. 83 illustrates an image of a closure device with a guidewire lumen closure pin, according to aspects of the present embodiments.

FIGS. 78-83 illustrate images of the closure device 100 with a seventh embodiment of the guidewire lumen closure pin 980, according to aspects of the present embodiments. The seventh embodiment of the closure pin 980 includes an L-shaped closure pin 980 that is integrated into (and monolithic with) the column 122. As a scaffold 990 slides down the delivery shaft and over the L-shaped closure pin 980 (FIGS. 80 and 81), the scaffold 990 forces the orthogonal tip of the L-shaped closure pin 980 into a partial bore 974 in only one sidewall of the column 122 (i.e., rather than all the way through both side walls; shown in FIG. 82). The orthogonal tip of the L-shaped closure pin 980 traverses the guidewire lumen 912, thereby sealing the guidewire lumen 912, as shown in FIG. 83. In the embodiments of each of FIGS. 46-77, the closure device may include a push tube disposed concentrically within the delivery shaft 918, the push tube being used for distally pushing the closure pins 902, 930, 940, 950, 960, and 970 into the column 122 and/or guidewire lumen 912 after the guidewire 17 has been withdrawn from the guidewire lumen 912. In each of the second, third, fourth, sixth, and seventh embodiments of the closure pin 930, 940, 950, 970, 980, the column 122 is configured such that the guidewire 17 and guidewire lumen 912 are centered (i.e., concentric) within the column 122. In each of the first and fifth embodiments of the closure pin 902, 960, the column 122 is configured such that the guidewire 17 and guidewire lumen 912 are offset (i.e., eccentric) within the column 122.

Scaffold Design

Figure 84:
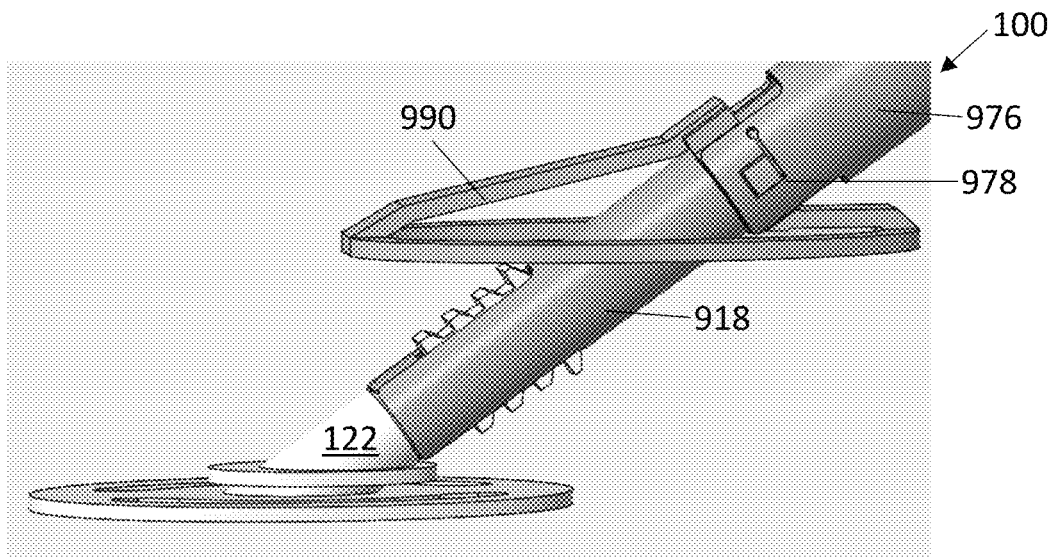
FIG. 84 illustrates an image of a closure device, according to aspects of the present embodiments.
Figure 85:
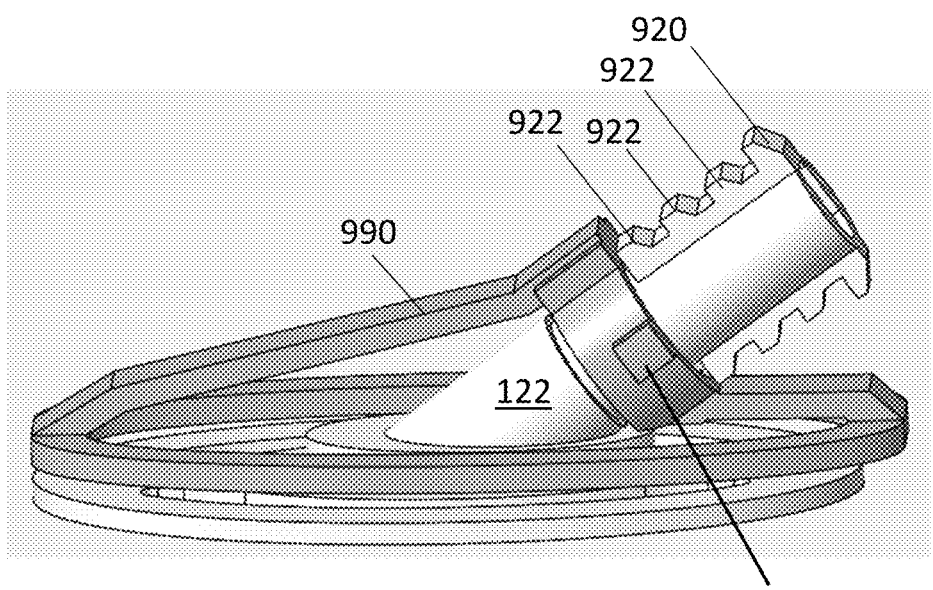
FIG. 85 illustrates an image of a closure device, according to aspects of the present embodiments.
Figure 86:
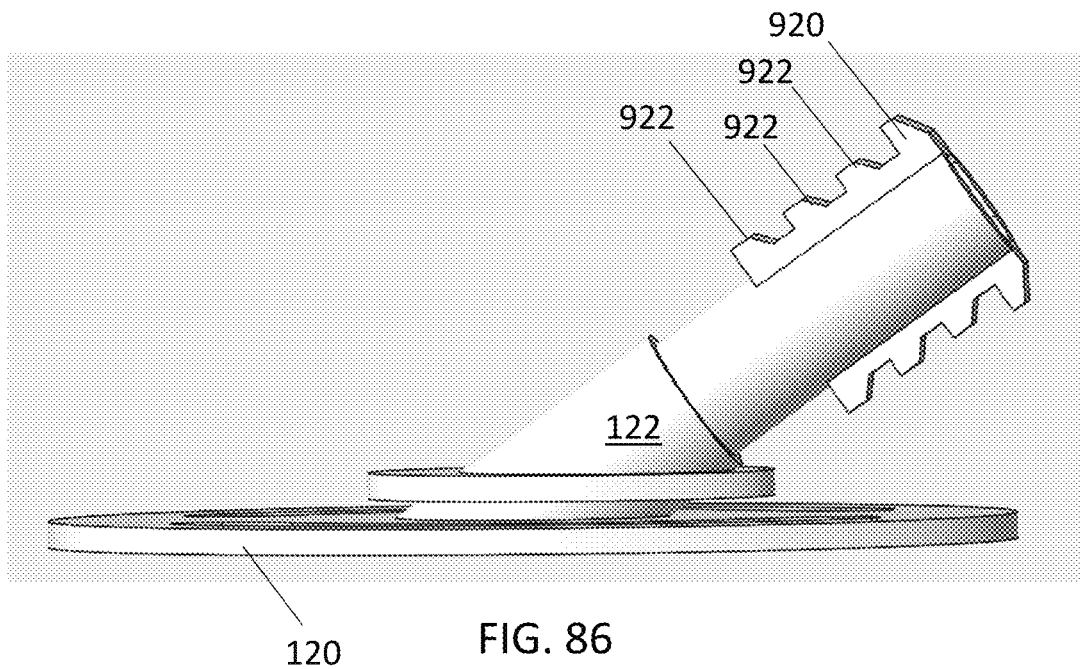
Figure 87:
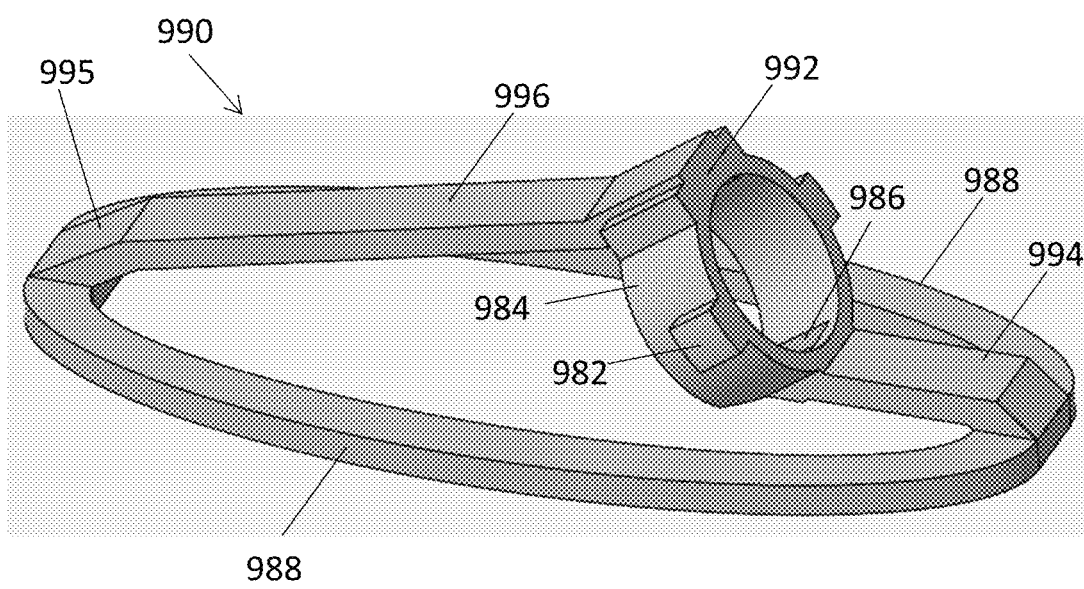
Figure 88:
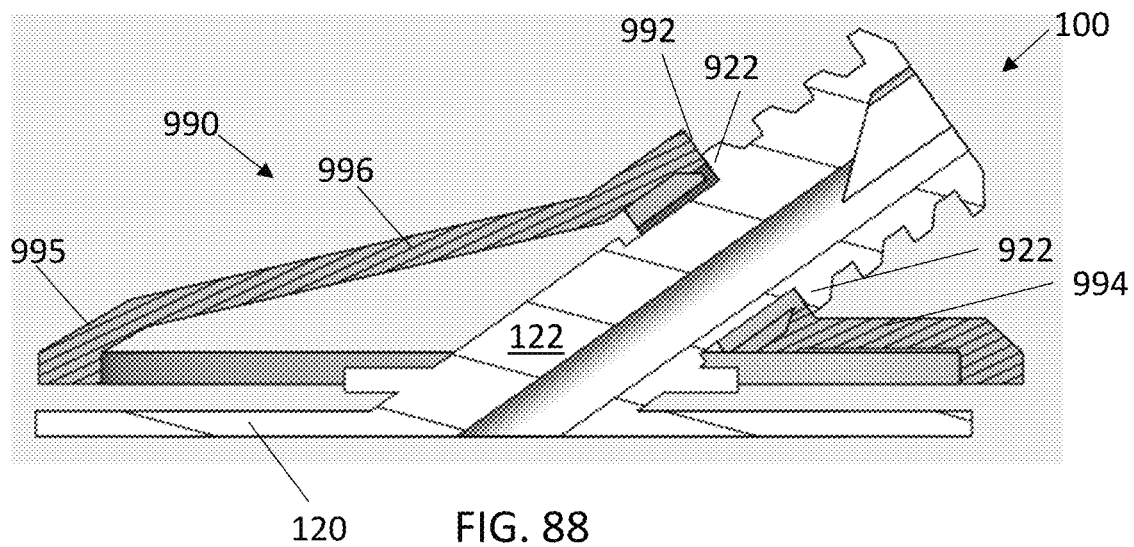

FIGS. 84-88 illustrate images of the closure device 100 including the scaffold 990 and base 120 with column 122 protruding therefrom, according to aspects of the present embodiments. As shown in FIG. 84, the delivery tube 976 concentrically slides around the delivery shaft 918 to deliver the scaffold 990 to the closure site. The delivery tube 976 may include square-shaped recesses 978 on opposing sides for interfacing with lateral notches 982 on the scaffold 990 during delivery of the scaffold 990 to the closure site. The column 122 may include four pairs of locking tabs, with a proximal pair of locking tabs 920 being larger than each of the second, third, and fourth pairs of locking tabs 922, similar to the embodiments of FIGS. 55-57. The locking tabs interface with a top surface 992 of a collar 984 of the scaffold 990, as shown in FIGS. 85, 87, and 88. The collar 984 becomes disposed around the column 122 as the scaffold 990 moves distally toward the closure site. Referring to FIG. 87, the scaffold 990 may include an anterior member 996 and a posterior member 994, both coupled to opposing sides of the collar 984. In some embodiments, the anterior and posterior members 996, 994 are each coupled to lateral members 988 on opposing lateral sides of the scaffold 990, a configuration which provides enhanced flexibility of the scaffold. The collar 984 may also include an internal recess 986 that interfaces with the locking tabs 920, 922 allowing and/or encouraging movement of the scaffold 122 in a distal direction around the column 122. The collar 984 (or neck 984) may include a larger diameter compared to previous designs to accommodate a larger-diameter column 122, which in turn may be larger to accommodate a thicker (for example, 0.035 inch) guidewire 17. The 0.035 inch guidewire 17 (or, for example 0.02 to 0.05 inch guidewire 17) allows procedures to be performed without the need to do a wire exchange during the closure process, thereby saving time and eliminating steps. The top surface 992 of the collar 984 prevents movement in the proximal direction of the scaffold along the delivery shaft 918 after the collar 984 has engaged the locking tabs 920, 922.

FIG. 88 shows the scaffold 990 engaged with the base 120 and column 122, according to aspects of the present embodiments. In the configuration of FIG. 88, the fourth pair of locking tabs 922 (that is, on opposing sides of the column 122) interface with corresponding portions of the top surface 992 of the collar 984 to prevent proximal movement of the scaffold 990 relative to the base 120. For clarity purposes, the flexible sealable member is omitted from FIGS. 83, 84, and 88-92, but would be present in operation. Referring to FIGS. 87 and 88, the scaffold 990 may include an anterior member that includes two segments: a short steep first segment 995, and a longer less steep second segment 996, with the short steep first segment 995 being located distal of, and connecting to, the longer less steep second segment 996. The short steep first segment 995 may be oriented at an angle of about 30 degrees (or from about 28 degrees to about 32 degrees, or from about 25 degrees to about 35 degrees) from the horizontal plane (i.e., the plane of base 120). The longer less steep second segment 996 may be oriented at an angle of about 13 degrees (or from about 11 degrees to about 15 degrees, or from about 8 degrees to about 18 degrees) from the horizontal plane (i.e., the plane of base 120). The posterior member 994 may be oriented such that it is substantially parallel to (for example, angled within about 1 degree and/or within about 2 degrees of) the horizontal plane (i.e., the plane of base 120). In some embodiments, the posterior member 994 may be less than half the length of the longer less steep second segment of the anterior member 996. The centerline of column 122 (for example, the centerline of guidewire lumen 912) may be oriented at an angle of about 35 degrees (or from about 33 degrees to about 37 degrees, or from about 30 degrees to about 40 degrees) from the horizontal plane (i.e., the plane of base 120). In some embodiments, each of the anterior member 996, the posterior member 994, and the lateral members 998 may include a cross section with a width that is greater than the height while the collar 984 may include a cross section in which the height is greater than the width. The configuration and design of scaffold 990 (for example, the orientations and relative dimension of each of the anterior member 996, the posterior member 994, the lateral members 998, the collar 984, and other features of the scaffold 990) allow the scaffold 990 to accommodate the various loads (distal, proximal, lateral loads, etc.) experienced when in use, while simultaneously allowing the necessary flexibility required for closure of the target site. As a result, the present embodiments allow closure device 100 to accommodate the variety of tissue types and anatomy/disease states of patient's tissue tracts.

Figure 89:
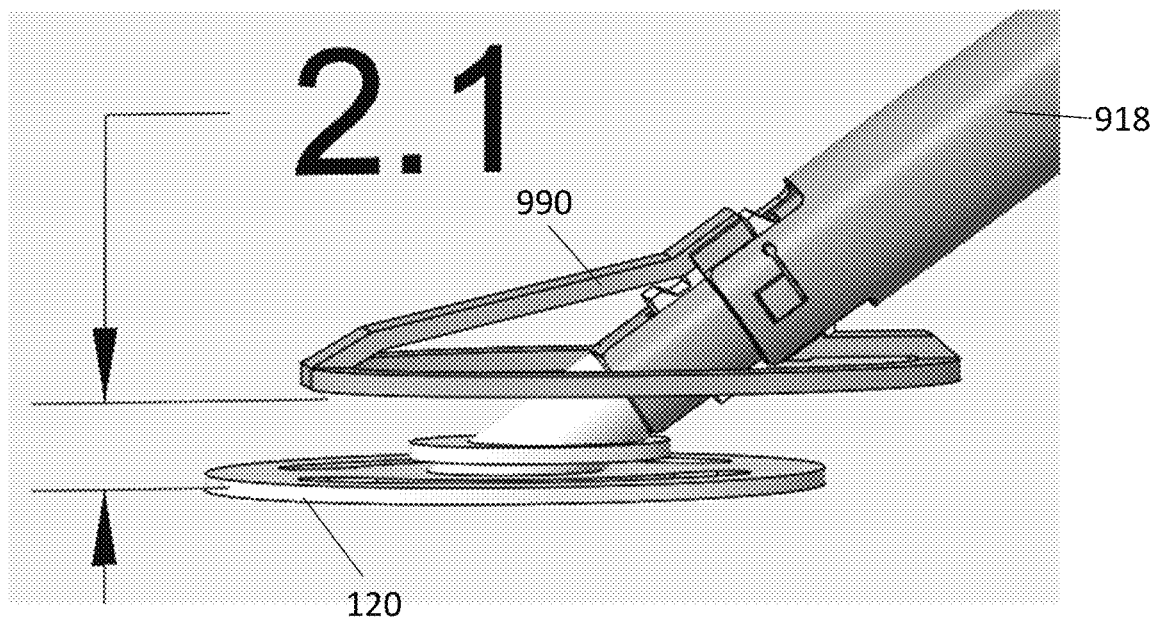
Figure 90:
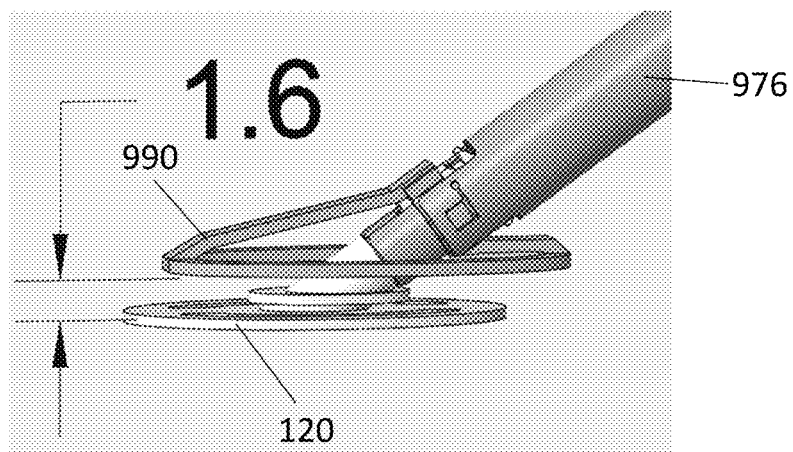
Figure 91:
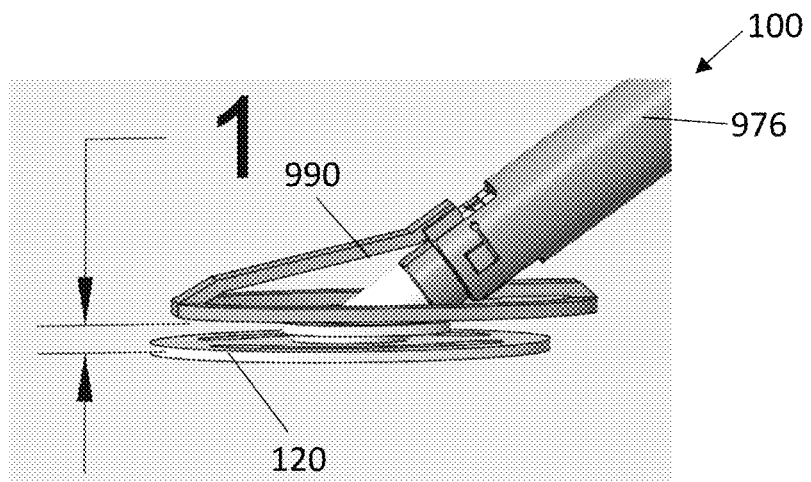
Figure 92:
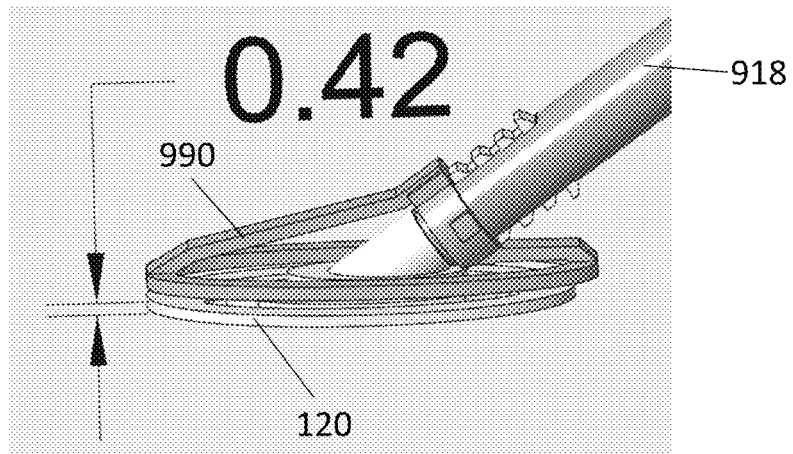

FIGS. 89-92 illustrate four different closure positions of the closure device 100 corresponding to each of the four sets of locking tabs 920, 922. The various closure positions allow the closure device 100 to accommodate a range of anatomies of patients who require endovascular treatments which may require closures of arteriotomies and/or venomoties. In FIG. 89, which corresponds to the scaffold being engaged with the first set of locking tabs 920, the device is configured such that there is a 2.1 mm gap between the scaffold 990 and the base 120. In FIG. 90, which corresponds to the scaffold being engaged with the second set of locking tabs 922, the device is configured such that there is a 1.6 mm gap between the scaffold 990 and the base 120. In FIG. 91, which corresponds to the scaffold being engaged with the third set of locking tabs 922, the device is configured such that there is a 1.0 mm gap between the scaffold 990 and the base 120. In FIG. 92, which corresponds to the scaffold being engaged with the fourth set of locking tabs 922, the device is configured such that there is a 0.42 mm gap between the scaffold 990 and the base 120.

Other examples and methods of the delivery device are described in U.S. Patent Application Publication Nos. 2013/0274795, 2017-0333014, and 2019/0021710, the contents of which are incorporated by reference herein in their entirety.

Exemplification

This Example describes an exemplary implantable device in accordance with the present disclosure. In particular, the implantable devices were made for sealing a puncture having a size of 26 F (i.e., 8.7 mm). An implantable device with a circular shaped flexible sealing member (PerQseal®), and an implantable device with an oval shaped flexible sealing member were prepared (PerQseal®+). The dimensions of the flexible sealable members are summarized in Table 2.

TABLE 2

|  | PerQseal ® | PerQseal ®+ |
| --- | --- | --- |
| Shape | Round (16 mm) | Oval (20 mm × 15 mm) |
| Thickness | 0.120 mm | 0.230 mm |

The devices were tested via two different models: bump and transverse dissection model; and longitudinal dissection model.

Bump and Transverse Dissection Model

To test the performance of the two devices under this model, 37° C. water was continuously supplied under physiological conditions of pulse (60 Hz) and pressure 120/80 mm Hg. The vessel model was a cast silicone replica of a diseased common femoral artery from a patient (plaques and calcification are the source of the 'bumps') and with built in simulated transverse dissections. The rig had a simulated tissue tract so the operator is deploying the device without seeing the implant during or post deployment in the vessel. The leakage was measured by capturing and weighing all the water which escapes from the vessel over a five minute period post deployment.

Longitudinal Dissection Model

37° C. water was continuously supplied under physiological conditions of pulse (60 Hz) and pressure 120/80 mm Hg. The vessel model was a silicone case with simulated 10.5 mm (32 F) longitudinal dissection in the proximal aspect of the vessel relative to the direction of the fluid flow. The same 5 minute collection time was used post deployment to assess the rate of leakage per minute from the hole, with the implant in place. The leakage was measured by capturing and weighing all the water which escapes from the vessel over a five minute period post deployment.

Results

The experimental results are summarized in Table 3. As can be seen, the leakages of the PerQseal®+ were only 3.53 and 0.14 ml/min for the bump model and longitudinal model, respectively. For the bump model, the leakage of PerQseal®+ was only 12% of PerQseal®. For the 10.5 mm model, the leakage of PerQseal®+ was less than 0.1% of PerQseal®. While the surface area of the PerQseal®+ was only 17% larger than PerQseal®, the significant improvement was achieved via PerQseal®.

TABLE 3

| Feature/Test | PerQseal ® | PerQseal ®+ | PerQseal ®+ vs PerQseal ® |
| --- | --- | --- | --- |
| Leakage in 'bump" and transverse dissection model (ml/min) | 29.5 | 3.53 | 12% |
| Leakage in 10.5 mm longitudinal dissection model (ml/min) | 175 | 0.14 | <0.1% |

What is claimed is:

1. A system for sealing an aperture in a tissue of a body lumen of a subject, the system comprising:
   an implantable device comprising a flexible sealable member,
      wherein the flexible sealable member is positionable against an internal surface of the tissue adjacent the aperture in the tissue when the implantable device is in a sealing position, wherein the flexible sealable member comprises a flexible substrate and a mesh layer disposed on the flexible substrate, and wherein the flexible sealable member has an elongated shape so that a longitudinal dimension of the flexible sealable member is greater than a lateral dimension of the flexible sealable member; and a delivery device for delivering the implantable device into the subject for positioning of the flexible sealable member against the internal surface of the tissue adjacent the aperture, wherein the implantable device further comprises a support member, wherein the support member comprises a base and a column, wherein the column is disposed in and through the aperture, and the base is disposed in the body lumen to retain the sealable member against the interior surface of the tissue of the body lumen when the device is in the sealing position, each of the base and column comprising a guidewire lumen through which a guidewire is disposed during delivery of the implantable device to the body lumen of the subject, the system further comprising a closure pin disposed within the column for sealing the guidewire lumen after the guidewire is removed from the guidewire lumen, wherein the closure pin comprises at least one of an angled tip and a substantially circular pin head.

2. The system of claim 1, wherein an average thickness of the flexible sealable member is greater than 100 µm.

3. The system of claim 1, wherein the aperture is located in a blood vessel, and a longitudinal axis of the flexible sealable member is aligned with a longitudinal axis of the blood vessel.

4. The system of claim 1, wherein the longitudinal dimension of the flexible sealable member is within a range of about 6 to about 29 mm and the lateral dimension of the flexible sealable member is within a range of about 4 mm to about 22 mm.

5. The system of claim 1, wherein an average thickness of the flexible substrate is within a range of 100 µm to 500 µm, 150 µm to 300 µm, 150 µm to 250 µm, or 190 µm to 220 µm.

6. The system of claim 1, the mesh layer is in contact with the aperture when in the sealing position.

7. The system of claim 1, wherein the delivery system contains the implantable device, and the flexible sealable member is in a rolled conformation therein, wherein the mesh layer comprises a plurality of electrospun fibers, each of the plurality of electrospun fibers having a diameter in a range from 0.3 µm to 8 µm, wherein the plurality of electrospun fibers makes up from 1 volume % to 35 volume % or 5 volume % to 25 volume % of the mesh layer, and wherein the implantable device comprises at least one material selected from the group consisting of polydioxanone, poly-L-lactide, poly-D-lactide, poly-DL-lactide, polyglycolide, ε-caprolactone, polyethylene glycol, and copolymers thereof.

8. The system of claim 1, wherein the implantable device comprises a locator positionable near an exterior surface of the tissue adjacent to the aperture when the device is in the sealing position, wherein the locator is moveable to be positioned near the exterior surface of the tissue adjacent to the aperture such that a portion of the tissue is disposed between the locator and the sealable member when the device is in the sealing position.

9. The system of claim 1, wherein the column comprises at least one of an internal taper, a gradual tapered portion, and a ramp portion.

10. The system of claim 1, wherein the column comprises at least one of a sleeve portion, an angled surface, and a partial bore.

11. A system for sealing an aperture in a tissue of a body lumen of a subject, the system comprising:

an implantable device comprising a flexible sealable member, wherein the flexible sealable member is positionable against an internal surface of the tissue adjacent the aperture in the tissue when the implantable device is in a sealing position, wherein the flexible sealable member comprises a flexible substrate and a mesh layer disposed on the flexible substrate, and wherein the flexible sealable member has an elongated shape so that a longitudinal dimension of the flexible sealable member is greater than a lateral dimension of the flexible sealable member; and a delivery device for delivering the implantable device into the subject for positioning of the flexible sealable member against the internal surface of the tissue adjacent the aperture, wherein the implantable device further comprises a support member, wherein the support member comprises a base and a column, wherein the column is disposed in and through the aperture, and the base is disposed in the body lumen to retain the sealable member against the interior surface of the tissue of the body lumen when the device is in the sealing position, each of the base and column comprising a guidewire lumen through which a guidewire is disposed during delivery of the implantable device to the body lumen of the subject, further comprising a closure pin disposed within the column for sealing the guidewire lumen after the guidewire is removed from the guidewire lumen, wherein the closure pin comprises at least one of: a pair of first and second distally extending arms, a rupture portion, an offset bore, an angled pin, a slidable rod, and an L-shaped closure pin.

12. A system for sealing an aperture in a tissue of a body lumen of a subject, the system comprising:

an implantable device comprising a flexible sealable member, wherein the flexible sealable member is positionable against an internal surface of the tissue adjacent the aperture in the tissue when the implantable device is in a sealing position, wherein the flexible sealable member comprises a flexible substrate and a mesh layer disposed on the flexible substrate, wherein the flexible sealable member has an elongated shape so that a longitudinal dimension of the flexible sealable member is greater than a lateral dimension of the flexible sealable member;

a delivery device for delivering the implantable device into the subject for positioning of the flexible sealable member against the internal surface of the tissue adjacent the aperture, wherein the implantable device further comprises a support member, wherein the support member comprises a base and a column, wherein the column is disposed in and through the aperture, and the base is disposed in the body lumen to retain the sealable member against the interior surface of the tissue of the body lumen when the device is in the sealing position, each of the base and column comprising a guidewire lumen through which a guidewire is disposed during delivery of the implantable device to the body lumen of the subject, further comprising a closure pin disposed within the column for sealing the guidewire lumen after the guidewire is removed from the guidewire lumen, wherein distally pushing the closure pin into the column causes the closure pin to seal the guidewire lumen.

* * * * *